US012778649B2

(12) United States Patent
Beale et al.

(10) Patent No.: US 12,778,649 B2
(45) Date of Patent: Nov. 3, 2026

(54) MULTIPLE SPINAL SURGICAL PATHWAYS SYSTEMS AND METHODS

(71) Applicant: WARSAW ORTHOPEDIC, INC., Warsaw, IN (US)

(72) Inventors: Jeffrey W. Beale, Bartlett, TN (US); Thomas A. Carls, Memphis, TN (US); Richard A. Hynes, Melbourne, FL (US); Matthew M. Morrison, Cordova, TN (US)

(73) Assignee: WARSAW ORTHOPEDIC, INC., Warsaw, IN (US)

(*) Notice: Subject to any disclaimer, the term of this patent is extended or adjusted under 35 U.S.C. 154(b) by 0 days.

(21) Appl. No.: 19/019,331

(22) Filed: Jan. 13, 2025

(65) Prior Publication Data

US 2025/0152220 A1 May 15, 2025

Related U.S. Application Data

(63) Continuation of application No. 18/618,512, filed on Mar. 27, 2024, now Pat. No. 12,279,798, which is a (Continued)

(51) Int. Cl.
*A61B 17/88* (2006.01)
*A61B 17/00* (2006.01)
(Continued)

(52) U.S. Cl.
CPC ........ *A61B 17/88* (2013.01); *A61B 17/00234* (2013.01); *A61B 17/0218* (2013.01);
(Continued)

(58) Field of Classification Search
CPC .......... A61B 17/00234; A61B 17/3468; A61B 17/56; A61B 2017/564; A61B 17/70;
(Continued)

(56) References Cited

U.S. PATENT DOCUMENTS 5,242,444 A 9/1993 MacMillan
5,334,205 A 8/1994 Cain
(Continued)

FOREIGN PATENT DOCUMENTS

JP 2003-532459 11/2003
JP 2012-504464 2/2012
(Continued)

OTHER PUBLICATIONS

International Search Report and Written Opinion dated Oct. 1, 2015 from International Application No. PCT/US2015/037180.
(Continued)

*Primary Examiner* — Larry E Waggle, Jr.
(74) *Attorney, Agent, or Firm* — FOX ROTHSCHILD LLP

(57) ABSTRACT

A method facilitates the treatment of the spine of a patient by providing simultaneous access through at least a first opening and a second opening formed in the patient. For example, the method can include the acts of positioning the patient on a surgical table, providing the first opening into a posterior portion of the patient, providing the second opening into a lateral portion of the patient, inserting a first device through the first opening into the patient to contact the spine in a first direction that is transverse to the coronal plane of the patient, and inserting a second device through the second opening into the patient to contact the spine in a second direction that is transverse to the sagittal plane of the patient, where the first and second openings are accessible simultaneously, and, when the first and second devises are inserted into the patient, the position of the patient is stationary with respect to a portion of the table.

22 Claims, 35 Drawing Sheets

Related U.S. Application Data continuation of application No. 17/979,910, filed on Nov. 3, 2022, now Pat. No. 11,974,793, which is a continuation of application No. 16/850,409, filed on Apr. 16, 2020, now Pat. No. 11,490,939, which is a continuation of application No. 16/110,246, filed on Aug. 23, 2018, now Pat. No. 10,653,408, which is a continuation of application No. 15/618,302, filed on Jun. 9, 2017, now Pat. No. 10,080,559, which is a continuation of application No. 14/694,802, filed on Apr. 23, 2015, now Pat. No. 9,730,684.

(60) Provisional application No. 62/021,490, filed on Jul. 7, 2014.

(51) Int. Cl.

| | |
|---|---|
| ***A61B 17/02*** | (2006.01) |
| ***A61B 17/34*** | (2006.01) |
| ***A61B 17/56*** | (2006.01) |
| ***A61B 17/70*** | (2006.01) |
| ***A61F 2/44*** | (2006.01) |

(52) U.S. Cl.
CPC ........ *A61B 17/025* (2013.01); *A61B 17/3468* (2013.01); *A61B 17/56* (2013.01); *A61B 17/70* (2013.01); *A61F 2/4455* (2013.01); *A61B 2017/0256* (2013.01); *A61B 2017/564* (2013.01)

(58) Field of Classification Search
CPC . A61B 17/7062; A61B 17/7067; A61B 17/84; A61B 17/86; A61B 17/88; A61F 2/44; A61F 2/4455; A61F 2/46; A61F 2/4611
See application file for complete search history.

(56) References Cited

U.S. PATENT DOCUMENTS

| | | | |
|---|---|---|---|
| 5,439,464 | A | 8/1995 | Shapiro |
| 5,441,059 | A | 8/1995 | Dannan |
| 5,658,306 | A | 8/1997 | Kieturakis et al. |
| 5,730,756 | A | 3/1998 | Keiturakis et al. |
| 5,762,604 | A | 6/1998 | Kieturakis |
| 6,159,200 | A | 12/2000 | Verdura et al. |
| 6,165,184 | A | 12/2000 | Verdura et al. |
| 6,432,140 | B1 | 8/2002 | Lin |
| 6,530,930 | B1 | 3/2003 | Marino |
| 6,565,572 | B2 | 5/2003 | Chappuis |
| 7,087,056 | B2 | 8/2006 | Vaughan |
| 7,188,626 | B2 | 3/2007 | Foley |
| 7,234,180 | B2 | 6/2007 | Horton et al. |
| 7,396,360 | B2 | 7/2008 | Lieberman |
| 7,476,240 | B2 | 1/2009 | Raymond et al. |
| 7,527,638 | B2 | 5/2009 | Anderson et al. |
| 7,695,487 | B2 | 4/2010 | Peartree et al. |
| 7,713,290 | B2 | 5/2010 | Vaughan |
| 7,736,369 | B2 | 6/2010 | Amin et al. |
| 8,221,428 | B2 | 7/2012 | Trieu |
| 8,419,744 | B2 | 4/2013 | Petit |
| 8,532,778 | B2 | 9/2013 | Lin |
| 8,591,432 | B2 | 11/2013 | Pimenta |
| 8,840,621 | B2 | 9/2014 | Farr |
| 9,510,815 | B2 | 12/2016 | Aebi |
| 11,490,939 | B2 | 11/2022 | Beale et al. |
| 11,974,793 | B2 | 5/2024 | Beale et al. |
| 2003/0208202 | A1 | 11/2003 | Falahee |
| 2005/0065517 | A1 | 3/2005 | Chin |
| 2005/0125066 | A1 | 6/2005 | McAfee |
| 2005/0192589 | A1 | 9/2005 | Raymond et al. |
| 2005/0256578 | A1 | 11/2005 | Blatt et al. |
| 2006/0079908 | A1 | 4/2006 | Lieberman |
| 2006/0084977 | A1 | 4/2006 | Lieberman |
| 2006/0111714 | A1 | 5/2006 | Foley |
| 2008/0051851 | A1 | 2/2008 | Lin |
| 2008/0242939 | A1 | 10/2008 | Johnston |
| 2008/0243194 | A1 | 10/2008 | Lotz et al. |
| 2010/0016906 | A1 | 1/2010 | Abdou |
| 2010/0030065 | A1 | 2/2010 | Farr |
| 2010/0318134 | A1 | 12/2010 | Roche et al. |
| 2011/0009869 | A1 | 1/2011 | Marino |
| 2011/0065999 | A1 | 3/2011 | Manzanares |
| 2011/0112557 | A1 | 5/2011 | Beeley |
| 2011/0125266 | A1 | 5/2011 | Rodgers et al. |
| 2011/0184519 | A1 | 7/2011 | Trieu |
| 2011/0196429 | A1 | 8/2011 | Hua |
| 2011/0264222 | A1 | 10/2011 | Petit |
| 2012/0078255 | A1 | 3/2012 | Bleich et al. |
| 2012/0116517 | A1 | 5/2012 | Petit |
| 2012/0271424 | A1 | 10/2012 | Crawford |
| 2012/0296428 | A1 | 11/2012 | Donner |
| 2013/0085535 | A1 | 4/2013 | Greenhalgh |
| 2013/0211466 | A1 | 8/2013 | Ballard et al. |
| 2013/0225984 | A1 | 8/2013 | Cheng |
| 2013/0274818 | A1 | 10/2013 | Goshayeshgar et al. |
| 2014/0200618 | A1 | 7/2014 | Donner |
| 2014/0336763 | A1 | 11/2014 | Donner |
| 2014/0379032 | A1 | 12/2014 | Hennard |
| 2015/0094765 | A1 | 4/2015 | Donner |
| 2015/0150683 | A1 | 6/2015 | Donner |
| 2017/0119537 | A1 | 5/2017 | Tepper et al. |

FOREIGN PATENT DOCUMENTS

| | | |
|---|---|---|
| WO | WO01/76494 | 10/2001 |
| WO | WO2010/039817 | 4/2010 |
| WO | WO2012/140569 | 10/2012 |
| WO | WO2013/122765 | 8/2013 |

OTHER PUBLICATIONS

Supplementary European Search Report dated Feb. 8, 2018 from European Application No. 15818870.6.
Communication from Examining Division dated Jan. 26, 2021 for EP Application No. 15818870.
Communication from Examining Division dated Sep. 3, 2021 for EP Application No. 15818870.
Communication from Examining Division dated May 12, 2022 for EP Application No. 15818870.
Office Action and thereof dated Oct. 5, 2018 Japanese Application No. 2016-575791.

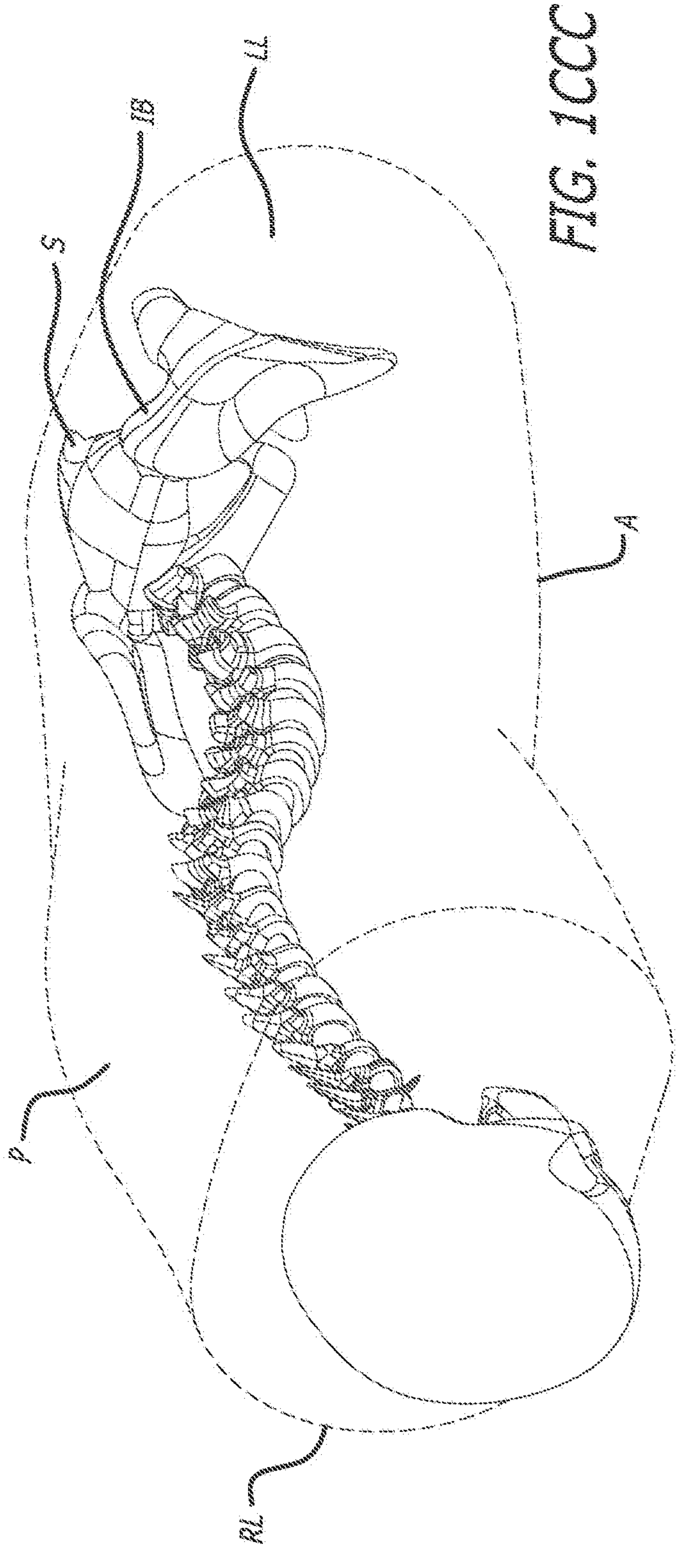
FIG. 1CCC

FIG. 1L
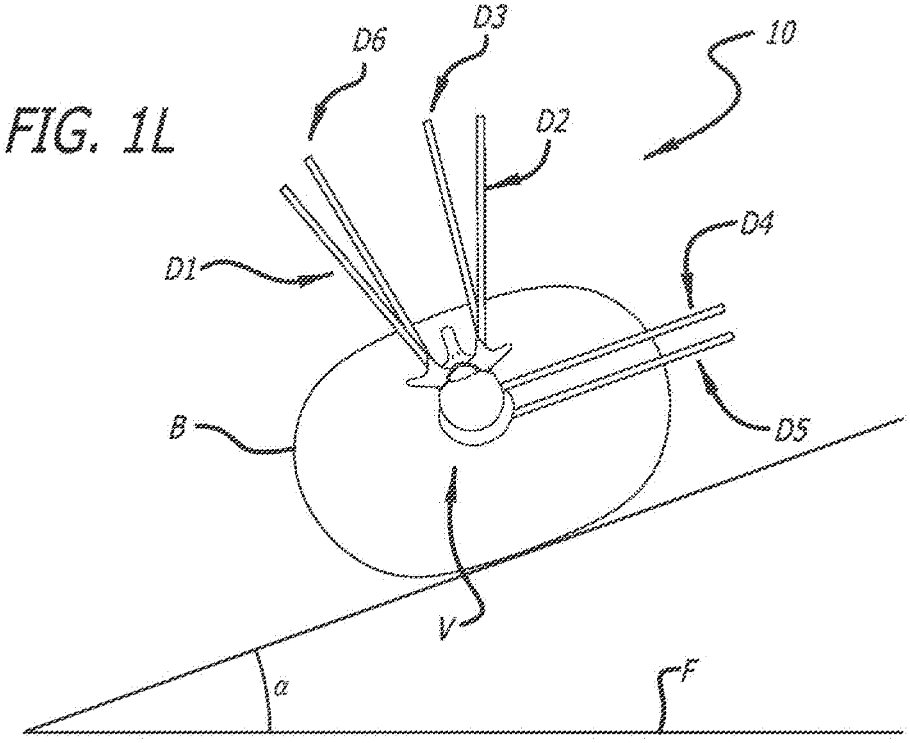
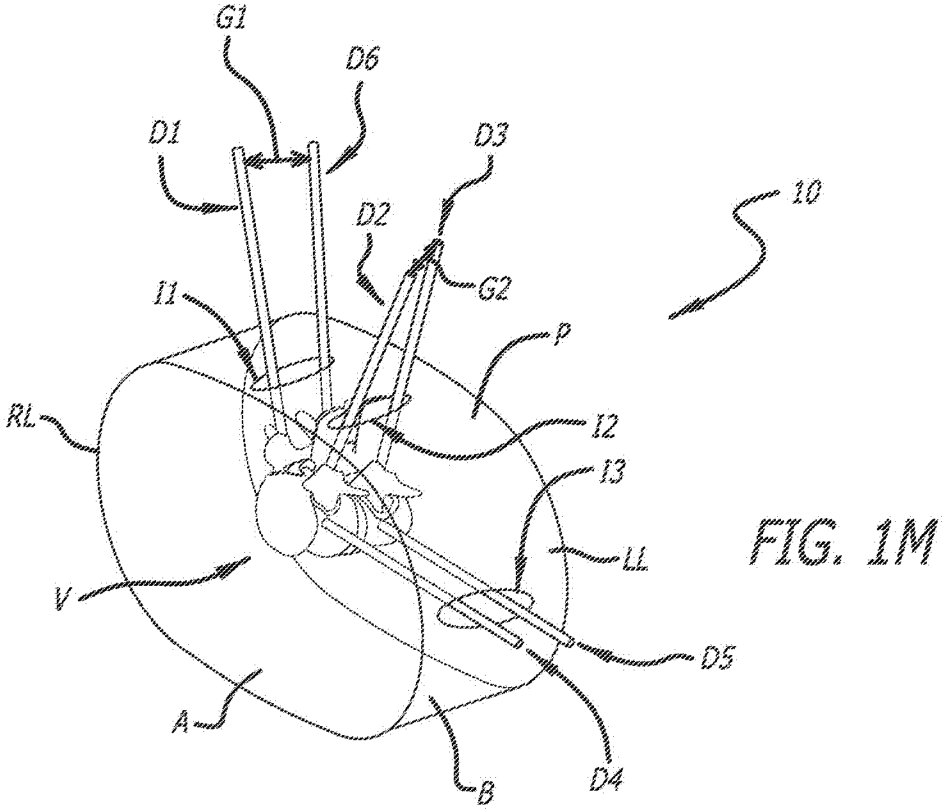
FIG. 1M

FIG. 2G
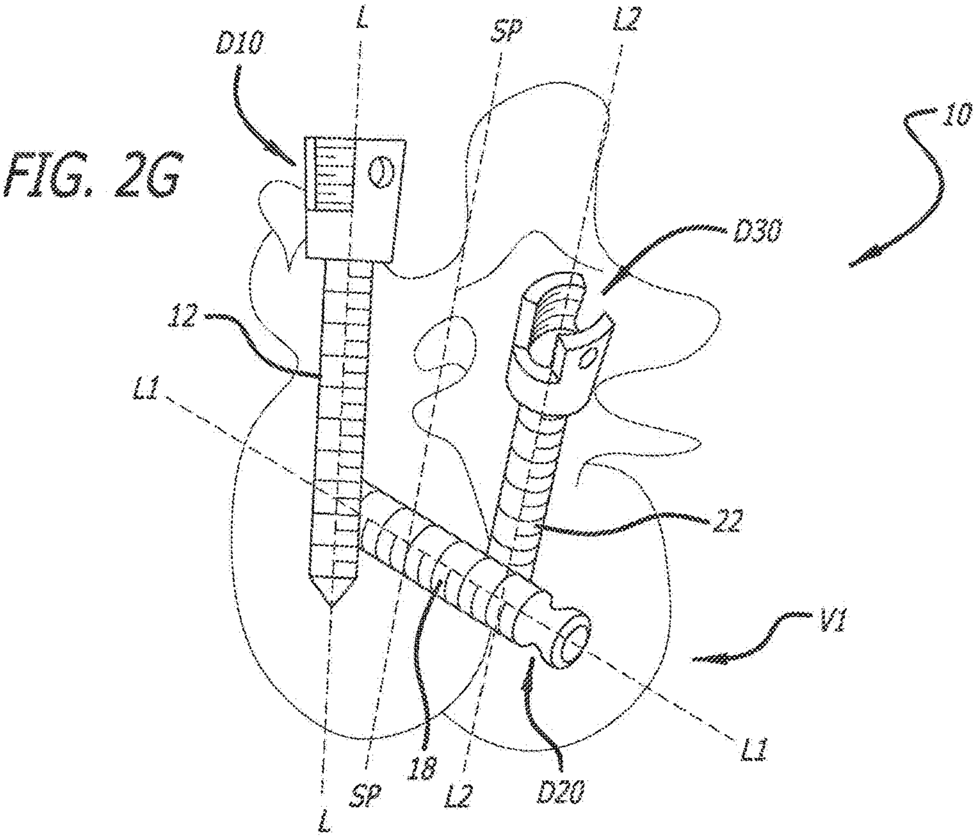
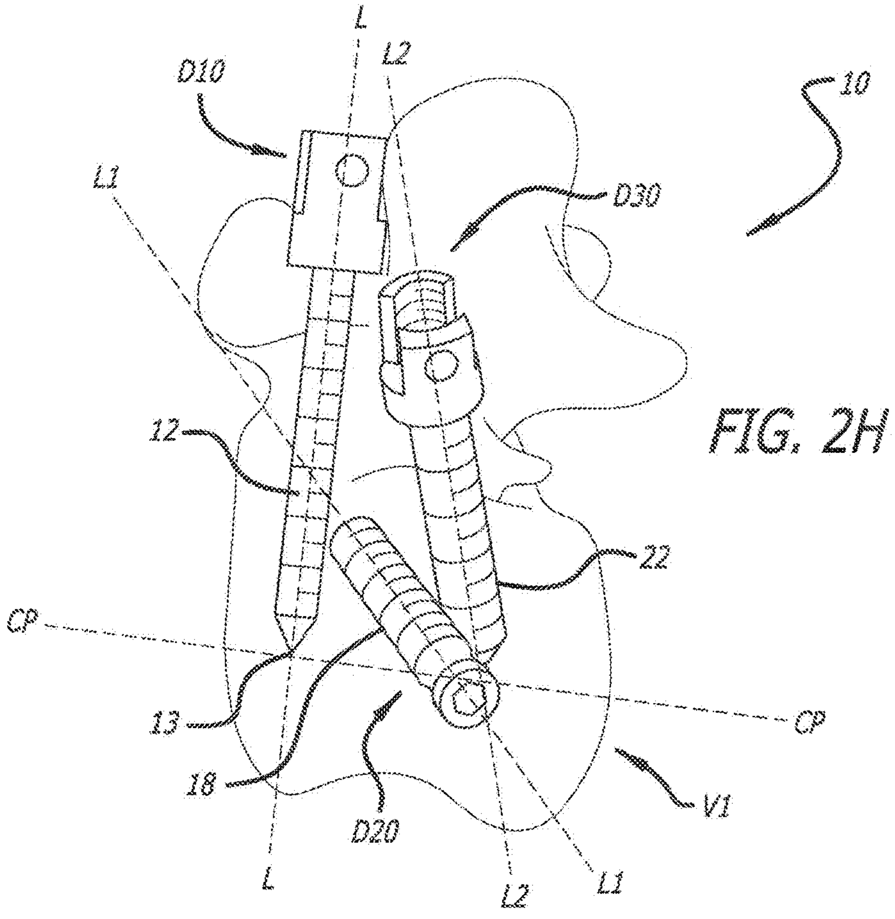
FIG. 2H

FIG. 3D
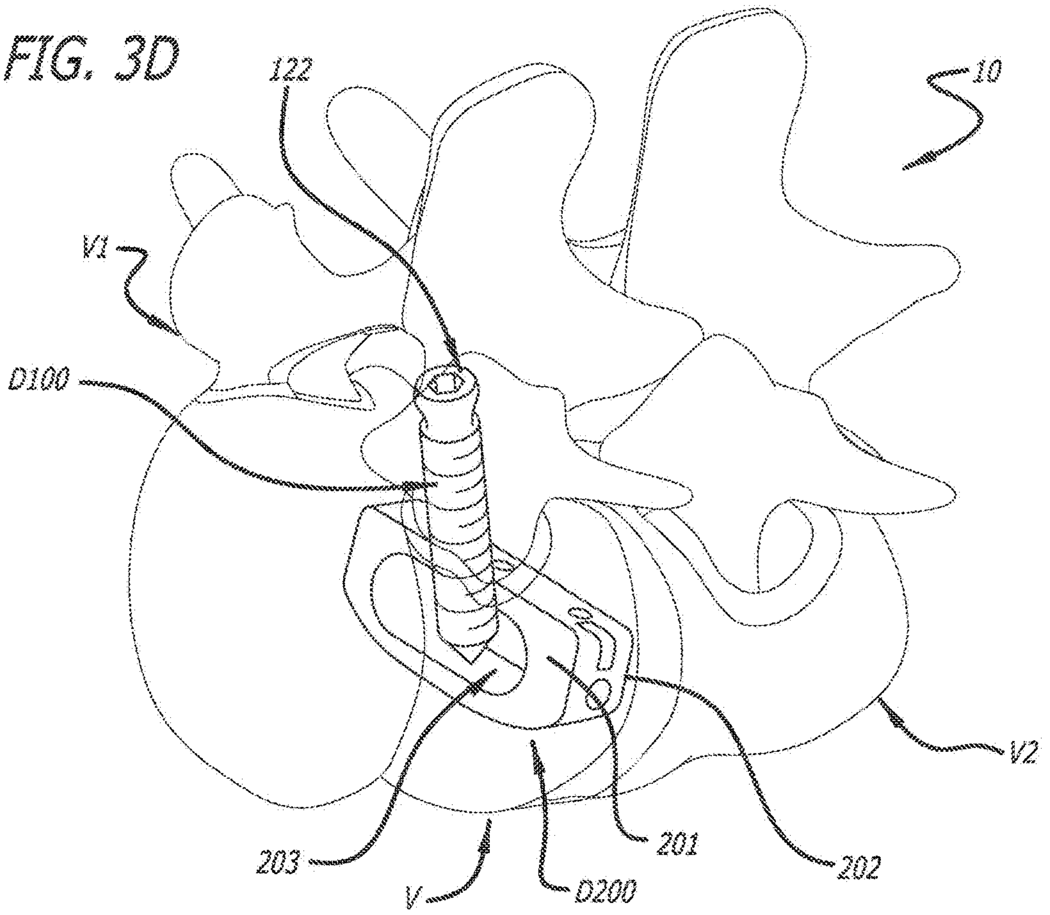
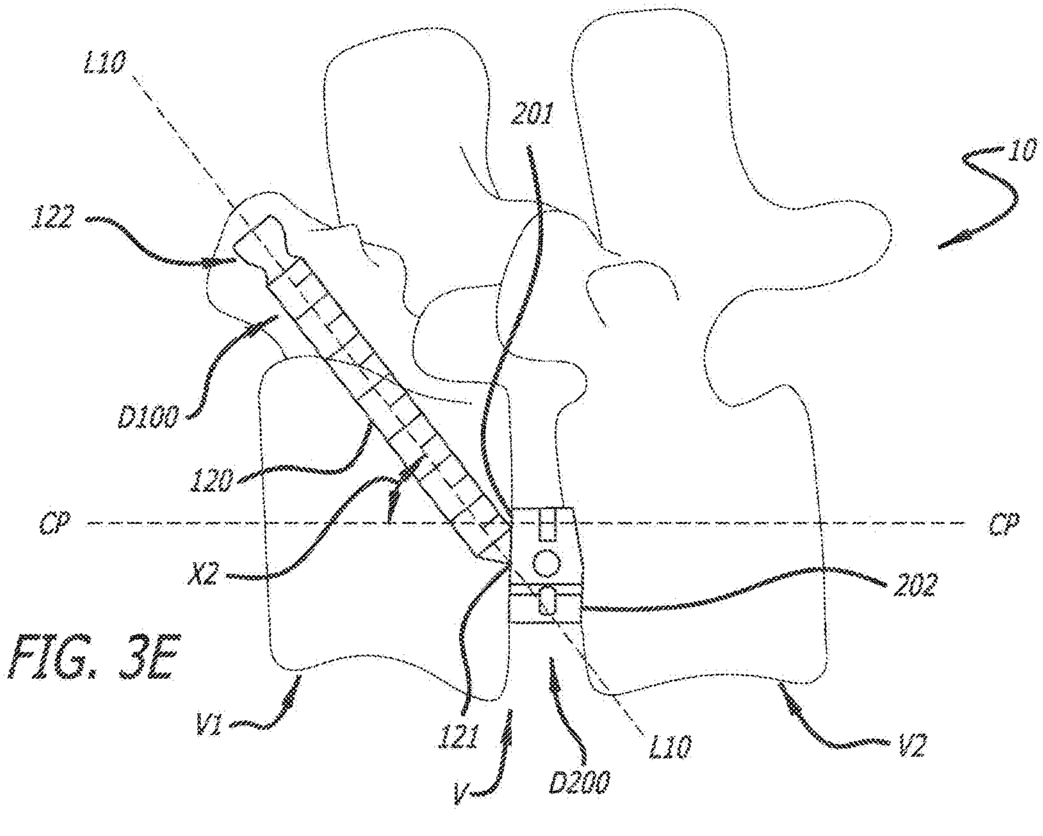
FIG. 3E

FIG. 3F
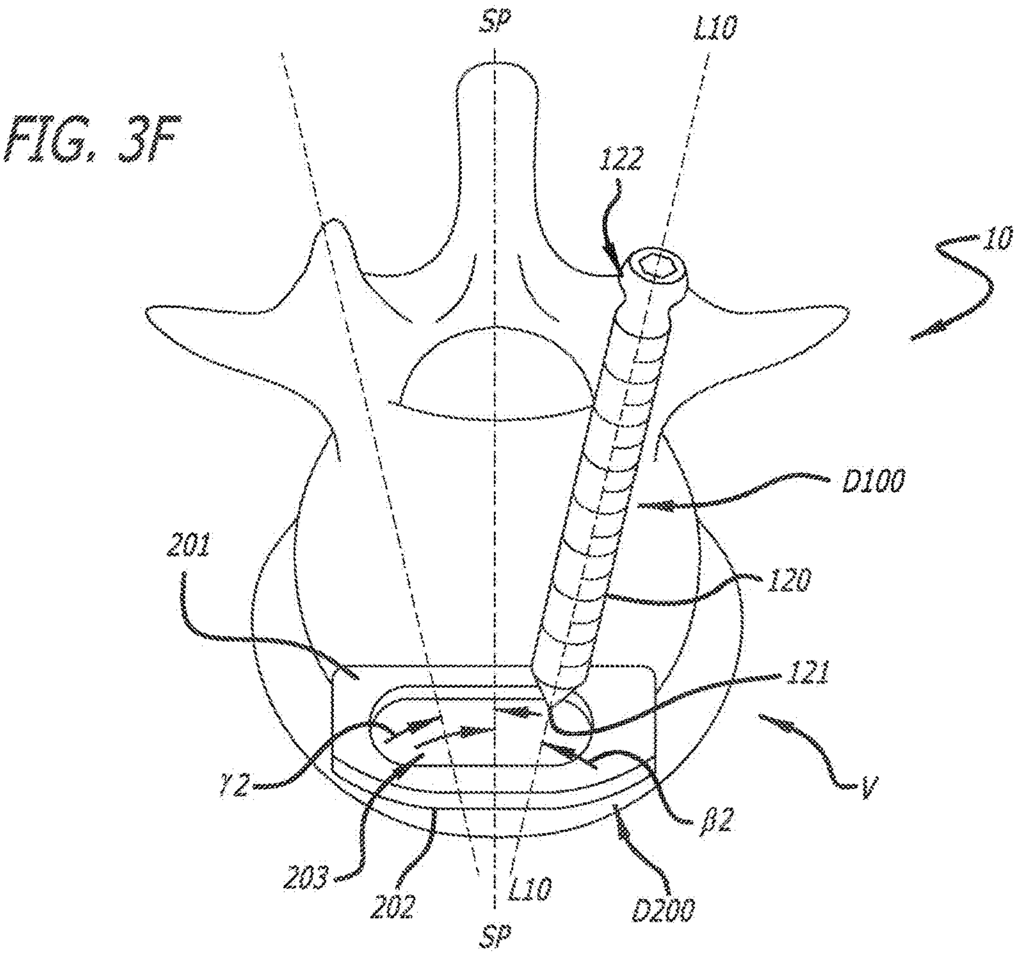
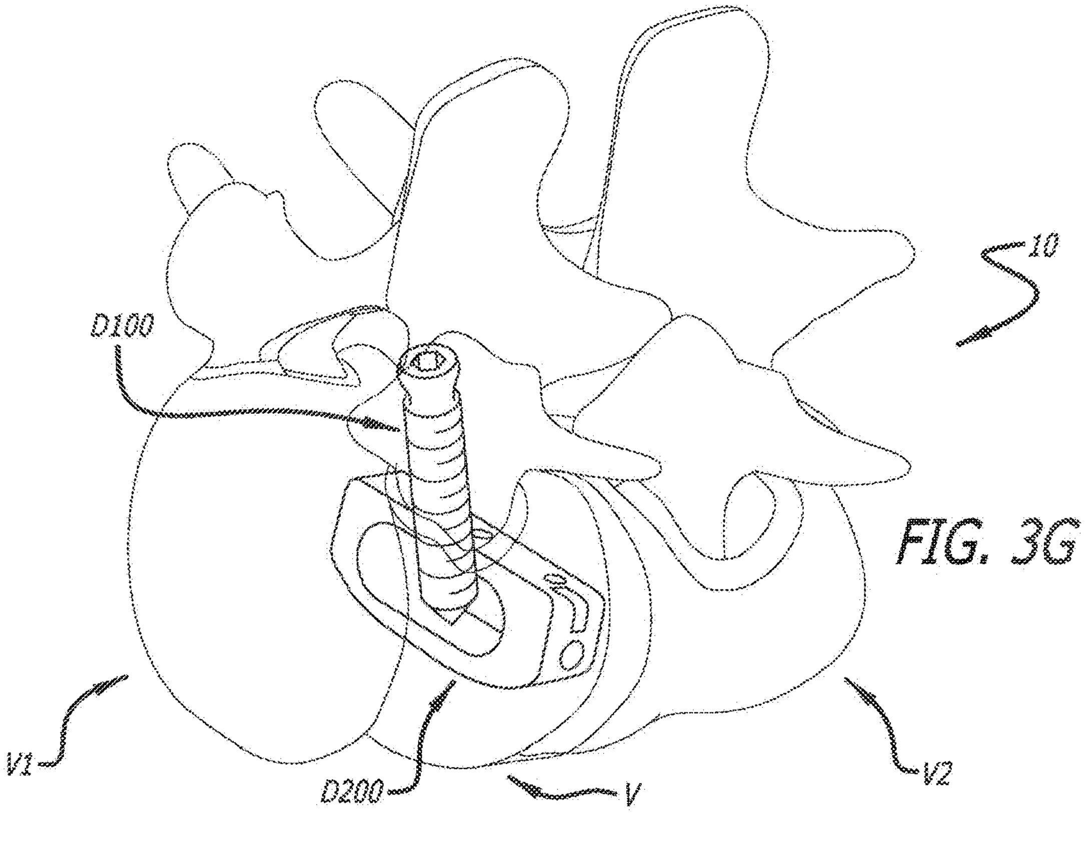
FIG. 3G

FIG. 3R
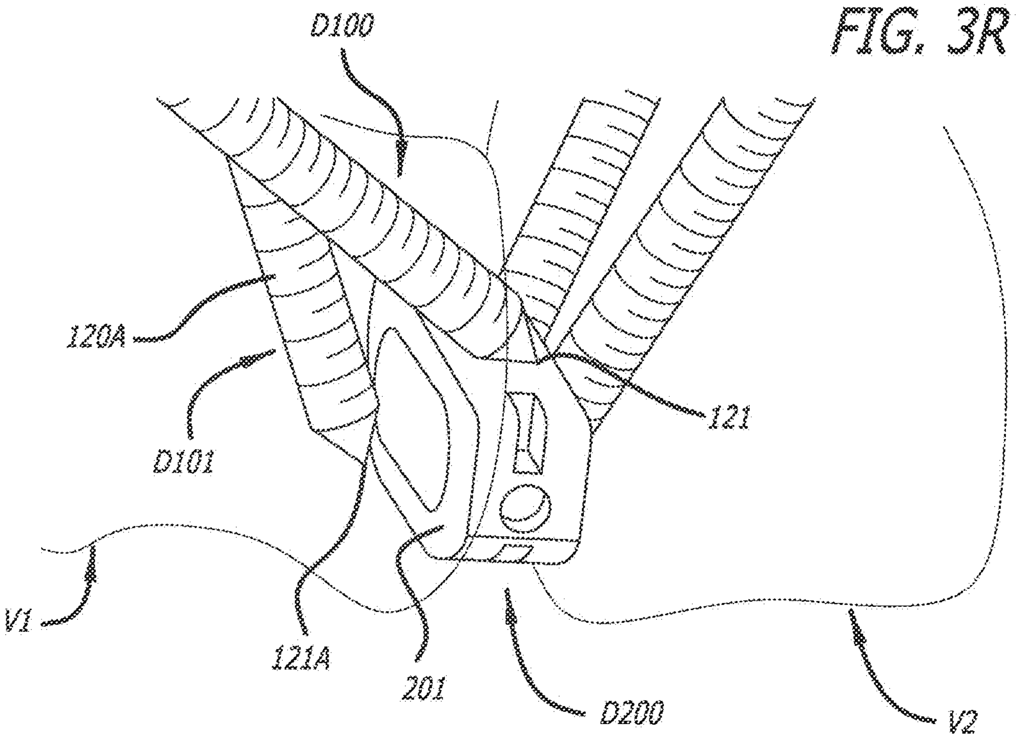
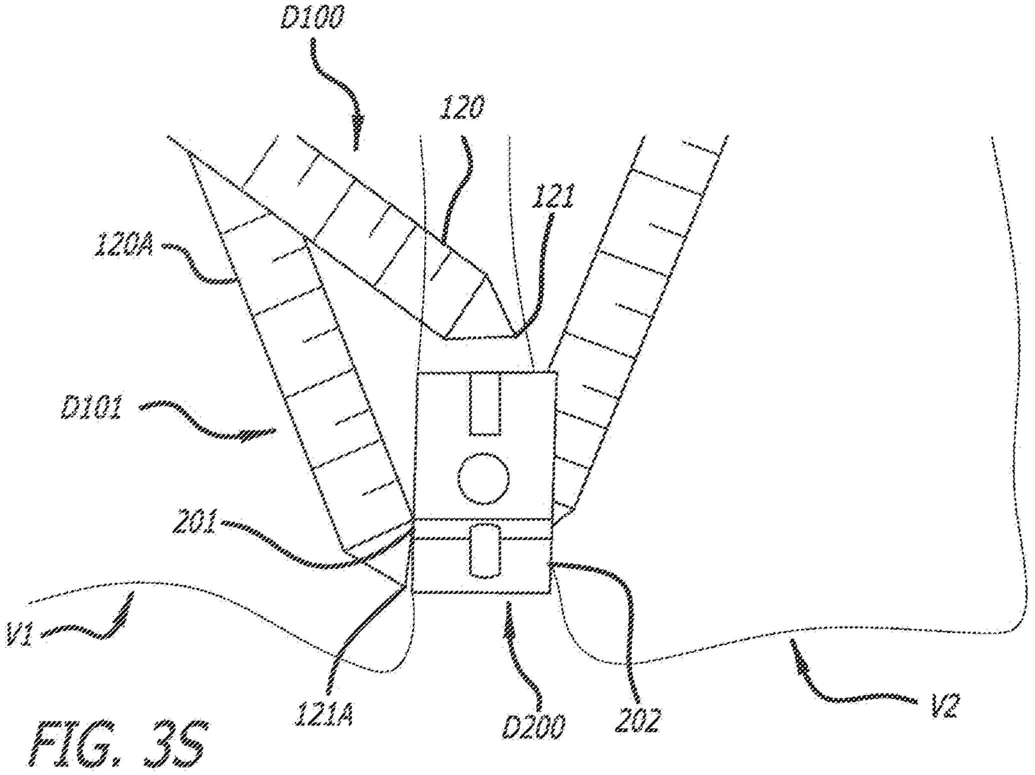
FIG. 3S

FIG. 4A
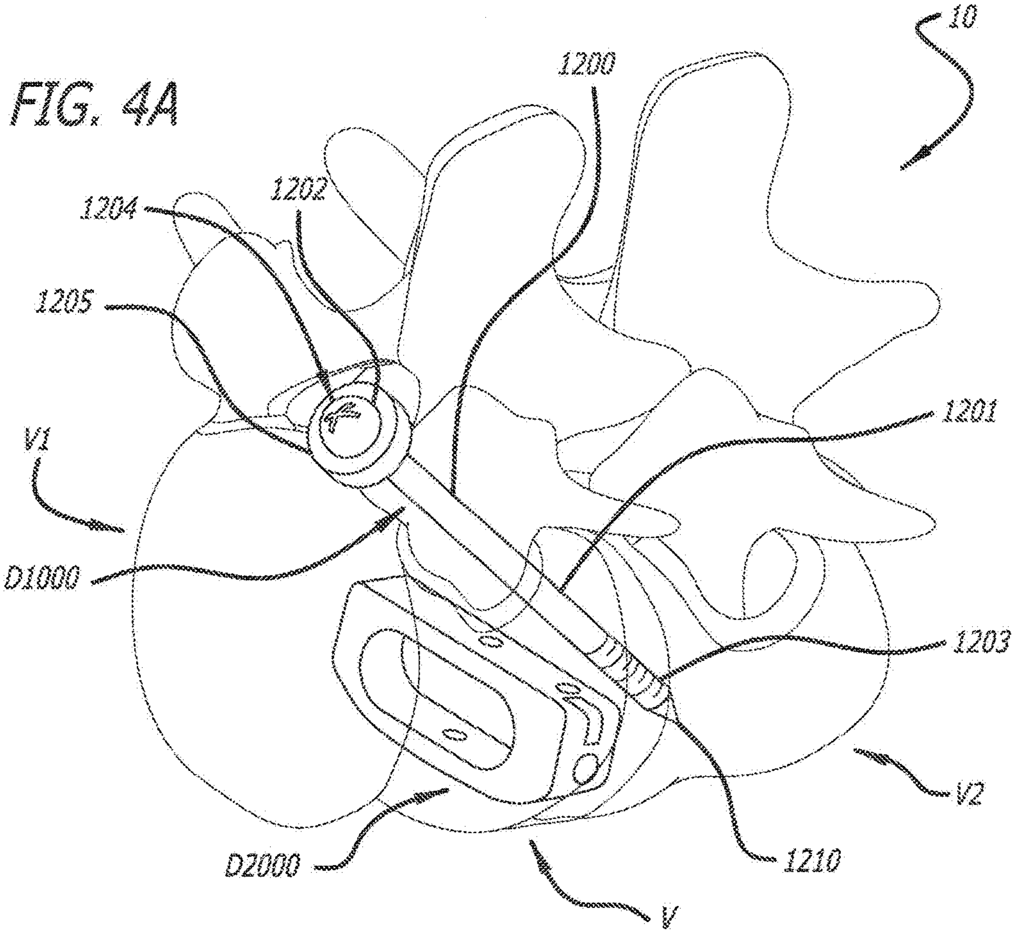
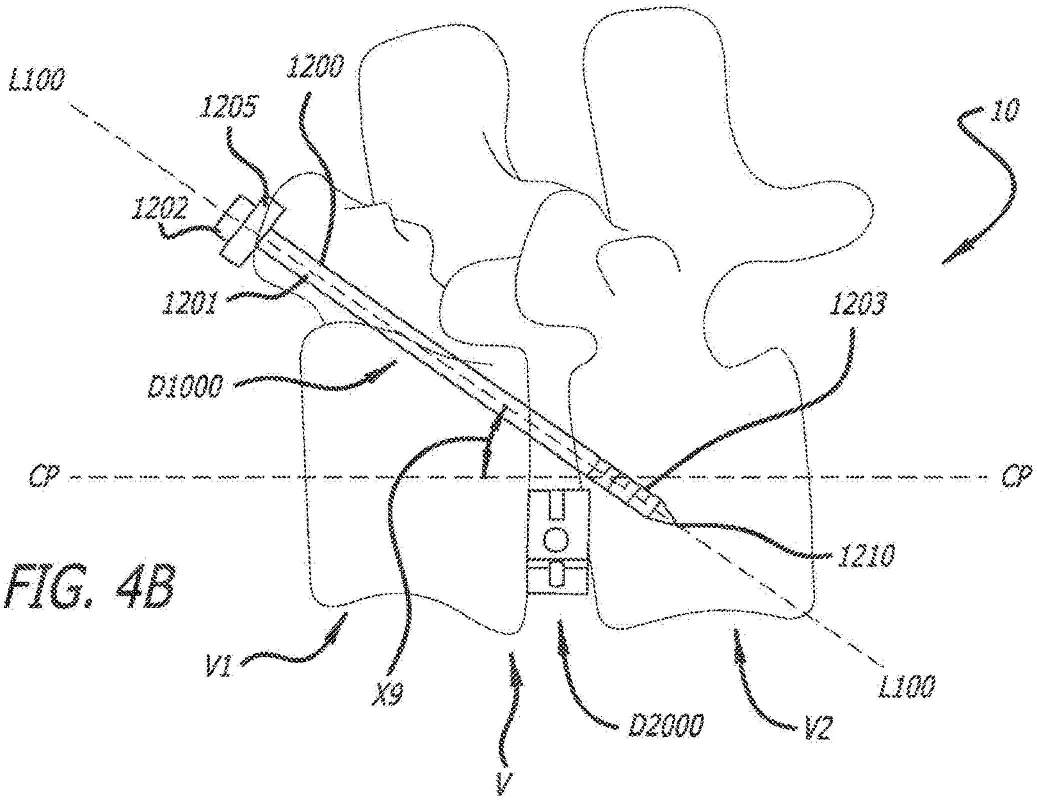
FIG. 4B

MULTIPLE SPINAL SURGICAL PATHWAYS SYSTEMS AND METHODS

The present application is a continuation of U.S. application Ser. No. 18/618,512, filed Mar. 27, 2024; which is a continuation of U.S. application Ser. No. 17/979,910, filed Nov. 3, 2022; which is a continuation of U.S. application Ser. No. 16/850,409, filed Apr. 16, 2020 (now U.S. Pat. No. 11,490,939); which is a continuation of U.S. application Ser. No. 16/110,246, filed Aug. 23, 2018 (now U.S. Pat. No. 10,653,408); which is a continuation of U.S. application Ser. No. 15/618,302, filed Jun. 9, 2017 (now U.S. Pat. No. 10,080,559); which is a continuation of U.S. application Ser. No. 14/694,802, filed Apr. 23, 2015 (now U.S. Pat. No. 9,730,684); which claims benefit of Provisional Application No. 62/021,490, filed Jul. 7, 2014; all of which are incorporated by reference herein.

TECHNICAL FIELD

The present disclosure generally relates to medical devices for the treatment of musculoskeletal disorders, and more particularly to a surgical system that utilizes multiple surgical pathways to manipulate and surgically treat the human spine.

BACKGROUND

Since the late 1800s, orthopedic surgeries have been performed to correct and stabilize patients' bony anatomy. While the majority of orthopedic surgeries continue to be performed on knees and hips, procedures on the spine have been increasing since the 1980s, and the number of approaches and procedures continues to expand. Rods, plates, screws, hooks, and interbody fusion spacers are examples of implants currently used align and stabilize patients' spines to address issues with deformity (such as scoliosis), tumor, trauma, or degenerative conditions.

Initially, surgeons treated their patients from a single incision, with a posterior approach. In this orientation, the patient may be positioned prone (on his/her stomach) and the surgeon makes an incision in the person's back. Corrections were made using instruments and implants from that approach, the implants were inserted and/or locked in place, and the incision was closed.

Not long after, anterior approaches started to be utilized. In an anterior approach, the patient may be positioned supine (on his/her back) and an incision is made in the abdomen, in line with where the correction needs to be made. This approach creates new challenges, because in a posterior approach the surgeon is just traversing muscle tissue, but in the anterior approach the surgeon is working near/against the patient's internal organs and vascular structures. The advantage of the anterior approach is that the anterior column of the spine is the primary load-bearing member, and addressing the anterior side directly is thought to allow the surgeon to impart greater correction than via a posterior-only approach.

A lateral approach has also been considered and used. In a lateral approach, the patient is typically positioned in the lateral decubitus position (e.g. on his/her side) and the incision is made approaching the anterior spinal column directly from the side, as opposed to the front as in the anterior approach. This avoids organs, as they tend to "fall forward" and move anteriorly out of the surgeon's field. But the lateral approach may also require addressing the psoas muscle, and within the psoas muscle are housed a bundle of nerve fibers that should be avoided to minimize post-operative complications. Therefore, the lateral approach was not used often until the advent of neural integrity monitoring, which allows the surgeon to monitor via electronic equipment how close they are to these nerves during the lateral approach. The lateral approach has physiologic limitations as well-ribs and the pelvis prevent easy access to levels beyond the upper lumbar region or below the third or fourth lumbar vertebra. However, the ability to place a large load-bearing interbody implant has made the lateral procedure appealing, despite its challenges.

Most recently, an oblique approach has been utilized. The patient may still be positioned laterally, but rather than a true lateral trajectory, the surgeon approaches the anterior from an oblique angle, or "tilted" towards the anterior spine. This allows access to the appropriate discs, yet avoids contact with the psoas (and hidden neural structures) while still avoiding conflict with the internal organs.

Finally, any of the above procedures might be used together in combination. For instance, the surgeon could perform an Oblique Lumbar Interbody Fusion (OLIF) procedure, thus providing a large anterior support structure using an interbody implant, then perhaps follow up with a posterior procedure to provide greater overall stability via posterior implant instrumentation. The surgeon could similarly couple any combination of procedures to accomplish treatment goals in a particular patient. Various approaches to the anterior spine can also be used in combination. For example, because direct lateral exposure does not allow for easy access to the lumbosacral junction (the disc between the lumbar spine and the sacrum or the L5-S1 space) the surgeon could perform an oblique or anterior approach to access that level, and then use direct lateral on the higher (superior) levels. In any event, in order to combine approaches, the surgeon currently has only two choices: reposition the patient during the procedure (while he/she is under anesthesia) or perform separate procedures in series (called "staged procedures"). In the first option, the length of surgery is extended, which is not preferable due to the desire to limit the amount of time that the patient is under anesthesia, and due to Operating Room (O.R.) operational costs added by the delay. Staged procedures may cost more, and typically involve increasing the patient's time in the hospital due to the multiple procedures. The changes in healthcare and/or implementation of the Affordable Healthcare Act (ACA) will likely affect the ability of the surgeon to choose particular combinations as well, given the drive towards cost containment and evidence-based medicine.

Therefore, there remains a clinical need in many cases for the surgeon to be able to utilize several different surgical approaches to the spine either substantially simultaneously or at the very least, during the same procedure. Furthermore, there exists a need for methods and apparatus that allow a surgeon more efficient and efficacious options for treating a patient using several approaches.

SUMMARY

The present invention in one preferred embodiment contemplates a method for surgically treating a spine in a patient is provided that includes inserting a first device through a first opening using a first approach; and inserting a second device through a second opening using a second approach while the first device is inserted through the first opening, where the first approach is different than the second approach.

The present invention in another preferred embodiment contemplates a method for surgically treating a spine in a patient is provided that includes performing a first surgical procedure with the patient in a surgical position; and performing a second surgical procedure without moving the patient from the surgical position, where the first and second surgical procedures are each selected from a group consisting of: discectomy, laminotomy, laminectomy, direct decompression, indirect decompression, cutting an anterior longitudinal ligament, implant insertion, trial insertion, distraction of vertebrae to ease implant insertion, distraction of vertebrae to facilitate disc removal, distraction of vertebrae to facilitate visualization and creation of a fulcrum, and where the first surgical procedure is different than the second surgical procedure.

The present invention in yet another preferred embodiment contemplates a method for surgically treating the spine of a patient that includes positioning a patient on a surgical table, providing a first opening into a posterior portion of the patient, providing a second opening into a lateral portion of the patient, inserting a first device through the first opening into the patient to contact the spine in a first direction that is transverse to the coronal plane of the patient, and inserting a second device through the second opening into the patient to contact the spine in a second direction that is transverse to the sagittal plane of the patient, where the first and second openings are accessible simultaneously, and, when the first and second devises are inserted into the patient, the position of the patient is stationary with respect to a portion of the table.

The present invention in still another preferred embodiment contemplates a method for surgically treating the spine of a patient that includes positioning the patient on a surgical table, maintaining a position of the patient with respect to the surgical table during surgery, while the position of the patient is being maintained, simultaneously accessing a first opening and a second opening in the patient during the surgery, the first opening affording access to a posterior portion of the patient, and the second opening affording access to a lateral portion of the patient, where accessing the first opening includes inserting a first device into the patient to contact the spine in a first insertion direction that can be from 45 degrees to −45 degrees with respect to a sagittal plane bisecting the patient, and where accessing the second opening includes inserting a second device into the patient to contact the spine in a second insertion direction that can be from 45 degrees to-45 degrees with respect to a coronal plane passing through the spine of the patient.

The present invention in yet still another preferred embodiment contemplates a method for surgically treating the spine of a patient that includes simultaneously accessing the spine of a patient through a first opening and a second opening in the patient during surgery, the first opening being through a posterior portion of the patient, and the second opening being through a lateral portion of the patient, while the first and second openings are being accessed, maintaining a position of the patient on a surgical table, inserting a first device through the first opening into the patient to contact the spine in a first insertion direction, inserting a second device through the second opening into the patient to contact the spine in a second insertion direction, inserting a third device through one of the first and second openings to contact the spine in a third insertion direction, and where the first insertion direction is substantially aligned with a sagittal plane bisecting the patient, the second insertion direction is substantially aligned with a coronal plane passing through the spine, and the third insertion direction is substantially perpendicular to one of the first and second insertion directions.

It is understood that both the foregoing general description and the following detailed description are exemplary and explanatory only, and are not restrictive of the invention as claimed.

BRIEF DESCRIPTION OF THE DRAWINGS

The present disclosure will become more readily apparent from the specific description accompanied by the following drawings, in which:

FIG. 1CC is a top, perspective view of the full length of the patient's spine depicting portions of the patient's abdomen shown in FIG. 1A;

FIG. 1CCC is another top, perspective view of the full length of the patient's spine depicting portions of the patient's abdomen shown in FIG. 1A;

FIG. 1L is a top view, in part cross section, of the patient's abdomen shown in FIG. 1A showing positioning of the patient's abdomen as the first device shown in FIG. 1E is inserted through the first incision using a posterior approach to engage the first vertebral body, the second device shown in FIG. 1E is inserted through the second incision using a posterior approach to engage the first vertebral body, the third device shown in FIG. 1E is inserted through the second incision using a posterior approach to engage the second vertebral body, the fourth device shown in FIG. 1E is inserted through the third incision using a lateral approach to engage the first vertebral body, the fifth device shown in FIG. 1E is inserted through the third incision using a lateral approach to engage the second vertebral body, and the sixth device shown in FIG. 1F is inserted through the first incision using a posterior approach to engage the second vertebral body;

FIG. 1M is a top, perspective view of portions of the spine shown in FIG. 1A depicting portions of the patient's abdomen shown in FIG. 1A, the first and second incisions shown in FIG. 1D, the third incision shown in FIG. 1D, the first device shown in FIG. 1E extending through the first incision using a posterior approach to engage the first vertebral body, the second device shown in FIG. 1E extending through the second incision using a posterior approach to engage the first vertebral body, the third device shown in FIG. 1E extending through the second incision using a posterior approach to engage the second vertebral body, the fourth device shown in FIG. 1E extending through the third incision using a lateral approach to engage the first vertebral body, the fifth device shown in FIG. 1E extending through the third incision using a lateral approach to engage the second vertebral body, and the sixth device shown in FIG. 1F extending through the first incision using a posterior approach to engage the second vertebral body, where the first, second, third, fourth, fifth and sixth devices are Steinmann pins;

FIG. 2G is a top, perspective view, in part phantom, of a vertebral body including a first device that is inserted through a first incision using a posterior approach to engage the vertebral body, a second device that is inserted through the first incision using a posterior approach to engage the vertebral body, and a third device that is inserted through a second incision using a lateral approach to engage the vertebral body, where at least one of the first and second devices are in a first plane and the third device is in a second plane that is different than the first plane;

FIG. 2H is a side, perspective view, in part phantom, of a vertebral body including the first device shown in FIG. 2G inserted through a first incision using a posterior approach to engage the vertebral body, the second device shown in FIG. 2G inserted through the first incision using a posterior approach to engage the vertebral body, and the third device shown in FIG. 2G inserted through a second incision using a lateral approach to engage the vertebral body, where at least one of the first and second devices are in a first plane and the third device is in a second plane that is different than the first plane;

FIG. 3D is a top, perspective view, in part phantom, of first and second vertebral bodies, with a first device extending through a first incision using a posterior approach such that the first device extends through the first vertebral body and into a space between the first and second vertebral bodies, and a second device extending through a second incision using a lateral approach to position the second device in the space between the first and second vertebral bodies such that a tip of the first device is positioned within the second device and a head of the first device is posterior to a facet of the first vertebral body;

FIG. 3E is a side view, in part phantom, of the first and second vertebral bodies shown in FIG. 3D, with the first device shown in FIG. 3D extending through a first incision using a posterior approach such that the first device extends through the first vertebral body and into a space between the first and second vertebral bodies, and the second device shown in FIG. 3D extending through a second incision using a lateral approach to position the second device in the space between the first and second vertebral bodies such that the tip of the first device is positioned within the second device and the head of the first device is posterior to the facet of the first vertebral body;

FIG. 3F is a top view, in part phantom, of the first and second vertebral bodies shown in FIG. 3D, with the first device shown in FIG. 3D extending through a first incision using a posterior approach such that the first device extends through the first vertebral body and into a space between the first and second vertebral bodies, and the second device shown in FIG. 3D extending through a second incision using a lateral approach to position the second device in the space between the first and second vertebral bodies such that the tip of the first device is positioned within the second device and the head of the first device is posterior to the facet of the first vertebral body;

FIG. 3G is a top, perspective view, in part phantom, of first and second vertebral bodies, with a first device extending through a first incision using a posterior approach such that the first device extends through the first vertebral body and into a space between the first and second vertebral bodies, and a second device extending through a second incision using a lateral approach to position the second device in the space between the first and second vertebral bodies such that a tip of the first device is positioned within the second device and a head of the first device is posterior to a facet of the first vertebral body, where the first device is a cannulated bone screw and the second device is an interbody implant;

FIG. 3O is a top view, in part phantom, of the first and second vertebral bodies shown in FIG. 3M, with the first device shown in FIG. 3M extending along a first surgical pathway using a posterior approach such that the first device extends through the first vertebral body and into a space between the first and second vertebral bodies, the second device shown in FIG. 3M extending along a second surgical pathway using a lateral approach to position the second device in the space between the first and second vertebral bodies such that the second device engages the first device, the third device shown in FIG. 3M extending along a third surgical pathway using a posterior approach such that the third device extends through the first vertebral body and into contact with the second device, the fourth device shown in FIG. 3M extending along a fourth surgical pathway using a posterior approach such that the fourth device extends through the second vertebral body and into the second device, and the fifth device shown in FIG. 3M extending along a fifth surgical pathway using a posterior approach such that the fifth device extends through the second vertebral body and into the second device;

FIG. 3R is an enlarged side, perspective view, in part phantom, of the first and second vertebral bodies shown in FIG. 3M, showing the relative orientations and position of each of the first, second, third, fourth and fifth devices shown in FIG. 3M;

FIG. 3S is an enlarged side view, in part phantom, of the first and second vertebral bodies shown in FIG. 3M, showing the relative orientations and position of each of the first, second, third, fourth, and fifth devices shown in FIG. 3M;

FIG. 4A is a top, perspective view, in part phantom, of first and second vertebral bodies, with a first device extending through a first incision using a posterior approach such that the first device extends through the first vertebral body and into the second vertebral body, and a second device extending through a second incision using a lateral approach to position the second device in a space between the first and second vertebral bodies;

FIG. 4B is a side view, in part phantom, of the first and second vertebral bodies shown in FIG. 4A, with the first device shown in FIG. 4A extending through a first incision using a posterior approach such that the first device extends through the first vertebral body and into the second vertebral body, and the second device shown in FIG. 4A extending through a second incision using a lateral approach to position the second device in a space between the first and second vertebral bodies.

DETAILED DESCRIPTION

Figure 1A:
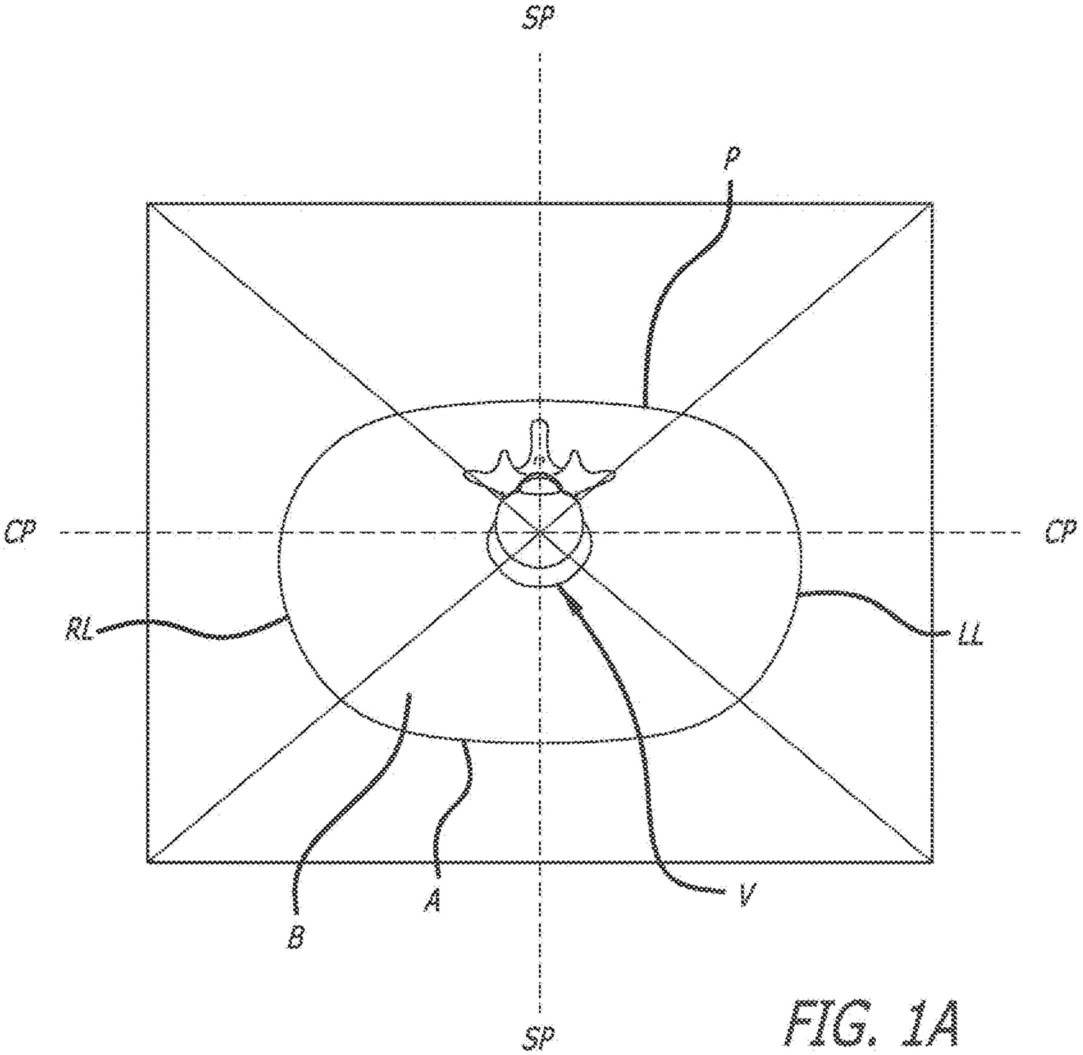
FIG. 1A is a diagram showing a portion of a spine of a patient within the patient's abdomen and posterior, anterior, right lateral and left lateral portions of the patient.

The exemplary embodiments of the methods disclosed are discussed in terms of methods for the treatment of musculoskeletal disorders and more particularly, in terms of methods for treating a spine. It should be understood that the various embodiments described herein may also be useful for establishing multiple surgical pathways in the treatment of other body systems or structures which may include, but are not limited to: orthopedic, cardiac, otolaryngologic and gastrointestinal. In some embodiments, the methods for treating a spine include, for example, antero-lateral interbody fusion (ALIF), oblique lateral interbody fusion (OLIF), midline interbody fusion (MIDLIF), and/or a direct lateral interbody fusion (DLIF).

In one embodiment, interbody implants and instruments are provided that are each positioned through different insertion pathways simultaneously to access at least a portion of the patient's spine. The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-4C, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites, depending on the particular application and/or preference of a medical practitioner. For example, the components of spinal implant system 10, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaS04 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials (for example, various PEEK interbody implants may be selectively coated with porous titanium). The components of spinal implant system 10 may be monolithically formed, integrally connected or include fastening elements and/or instruments, as described herein.

Spinal implant system 10 is employed, for example, with a fully open surgical procedure, a minimally invasive procedure, including percutaneous techniques, and mini-open surgical techniques to deliver and introduce instrumentation and/or an implant, such as, for example, at least one interbody implant, at a surgical site within a subject body B of a patient, which includes, for example, a spine having vertebrae V. In some embodiments, the implant(s) can include spinal constructs, such as, for example, pins, bone fasteners, spinal rods, connectors and/or plates.

As shown in FIG. 1A, body B includes a posterior portion P, an anterior portion A and opposite right lateral and left lateral portions RL, LL between posterior and anterior portions P, A. The instrumentation and/or implants of system 10 can be introduced into the patient using a posterior approach, an anterior approach, a right lateral approach, a left lateral approach, or a combination thereof. The posterior approach involves accessing at least one of vertebrae V through the back of the patient, such as, for example, posterior portion P. The anterior approach involves accessing at least one of vertebrae V through the front of the patient, such as, for example, anterior portion A. The right lateral approach involves accessing at least one of vertebrae V through the side of the patient, such as, for example, right lateral portion RL. The left lateral approach involves accessing at least one of vertebrae V through the side of the patient, such as, for example, left lateral portion LL.

In some embodiments, the posterior approach involves accessing at least one of vertebrae V via a pathway extending at an angle that is perpendicular to a coronal plane CP of body Band/or an acute angle relative to coronal plane CP. In some embodiments, the acute angle is in a range of about −45° o to about 45° o relative to a sagittal plane SP of body B and/or up to a right angle relative to coronal plane CP in a range of about −90° to about −90° relative to a sagittal plane SP of body B. In some embodiments, the anterior approach involves accessing at least one of vertebrae V via a pathway extending at an angle that is perpendicular to coronal plane CP of body B and/or an acute angle relative to coronal plane CP. In some embodiments, the acute angle is in a range of about −45° to about 45° relative to a sagittal plane SP of body B and/or up to a right angle relative to sagittal plane SP in a range of about −90° to about 90° relative to a sagittal plane SP of body B. In some embodiments, the right and left lateral approaches each access at least one of vertebrae V along a pathway extending parallel to coronal plane CP and/or at an acute angle relative to coronal plane CP. In some embodiments, the acute angle is a range of about −45° to about 45° relative to coronal plane CP of body B.

Figure 1B:
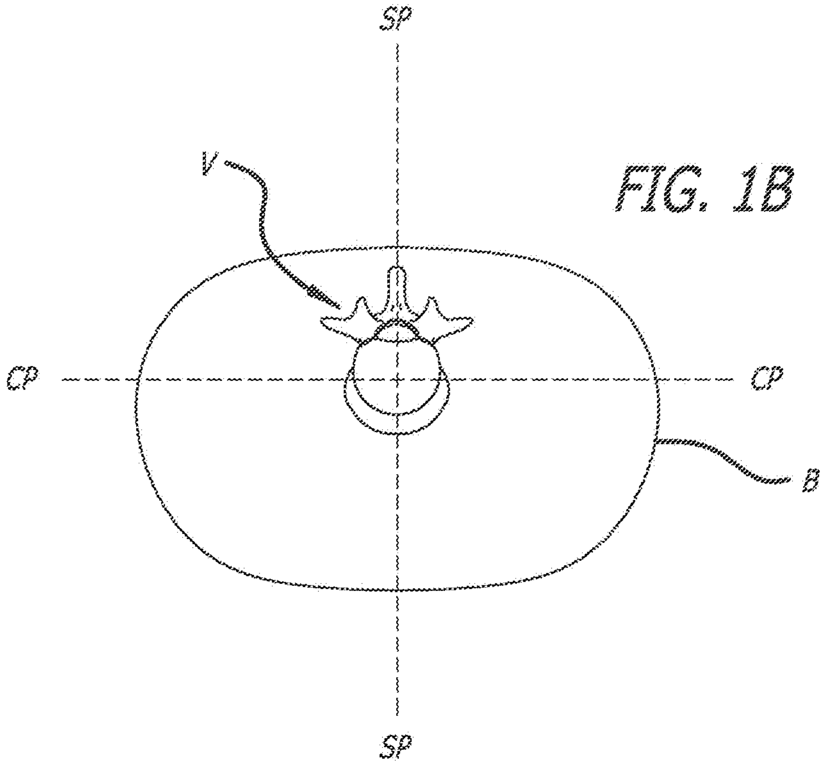
FIG. 1B is a top view showing the portion of the spine shown in FIG. 1A within the patient's abdomen shown in FIG. 1A.
Figure 1C:
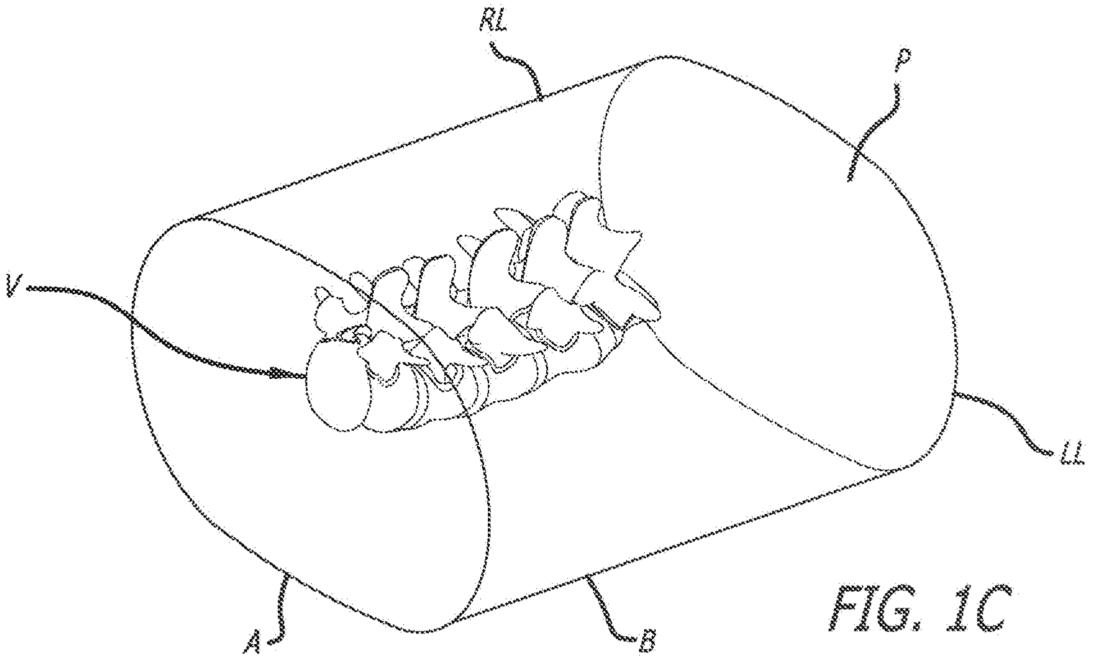
FIG. 1C is a top, perspective view of the portion of the spine shown in FIG. 1A depicting portions of the patient's abdomen shown in FIG. 1A.
Figure 1C:
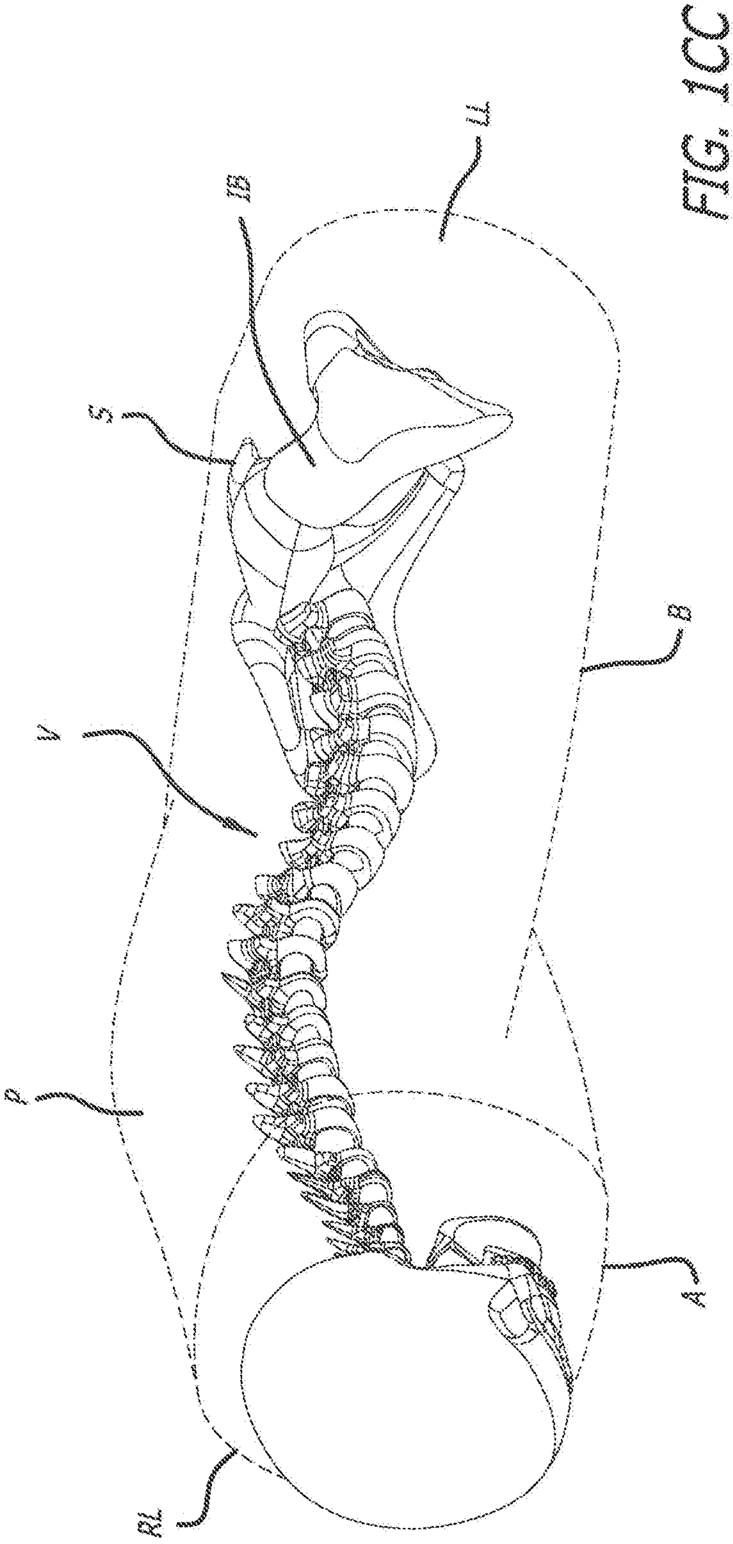
Figure 1D:
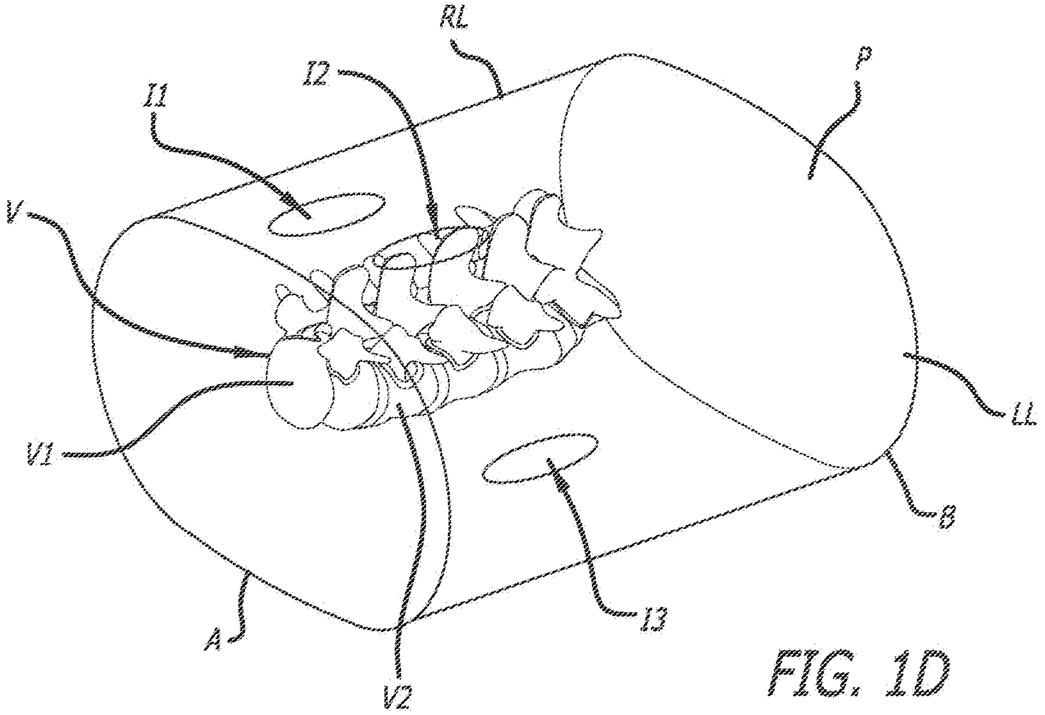
FIG. 1D is a top, perspective view of the portion of the spine shown in FIG. 1A depicting portions of the patient's abdomen shown in FIG. 1A, two incisions in the posterior portion of the patient to access the portion of the spine using a posterior approach, and one incision in the left lateral portion of the patient to access the portion of the spine using a lateral approach or an oblique approach.

In one embodiment, shown in FIGS. 1D-1H, 1M, and 1M, a first incision I1 is made in posterior portion P of a patient on to the right of a sagittal plane of body B, such as, for example, a midsagittal plane SP and a second incision I2 is made in posterior portion P of the patient to the left of sagittal plane SP, as shown in FIG. 1D, for example. First incision 11 defines a first surgical pathway to vertebrae V using a posterior approach and second incision I2 defines a second surgical pathway to vertebrae V using a posterior approach. First and second incisions I1, I2 are configured to provide access to at least a first vertebral body V1 and a second vertebral body V2 of vertebrae V. A third incision I3, as shown in FIG. 1D, for example, is made in left lateral portion LL of the patient. Third incision I3 defines a third surgical pathway to vertebrae V using a lateral approach to provide access to at least first vertebral body V1 and second vertebral body V2. In some embodiments, at least one of first, second and third incisions I1, I2, I3 is created for use in a fully open surgical procedure, a minimally invasive procedure, including percutaneous techniques, and mini-open surgical techniques that use a tube, such as, for example, a METRX® tube, an XTUBE® retractor or a QUADRANT™ retractor, all available from Medtronic Spine. In some embodiments, each of portions A, P, RL, LL can include one or a plurality of incisions, such as, for example, the incisions discussed above. That is, there is one or a plurality of incisions per surgical approach plane. In some embodiments, first, second and third incisions I1, I2, I3 can be anywhere in the patient's body where multiple entry points are necessary and/or desirable. The various incisions I1, I2, I3, for example, may be sized as relatively small "stab" incisions for percutaneous procedures, and/or longer >30 mm incisions that may be expanded to a "mini-open" incision or full open incision where larger swaths of the bony anatomy are exposed. Furthermore, various retractors and/or dilators may be used to prevent tissue migration into the working corridors initially established via incisions I1, I2, I3. Furthermore, the incisions I1, I2, I3 in a single procedure may be made with substantially equal sizes or have a variety of sizes to accommodate the various instruments, inserters and/or implants described more fully herein. The working spaces or working corridors defined by a combination of instruments via the incisions may be defined virtually by surgical navigation means as described further herein.

Figure 1E:
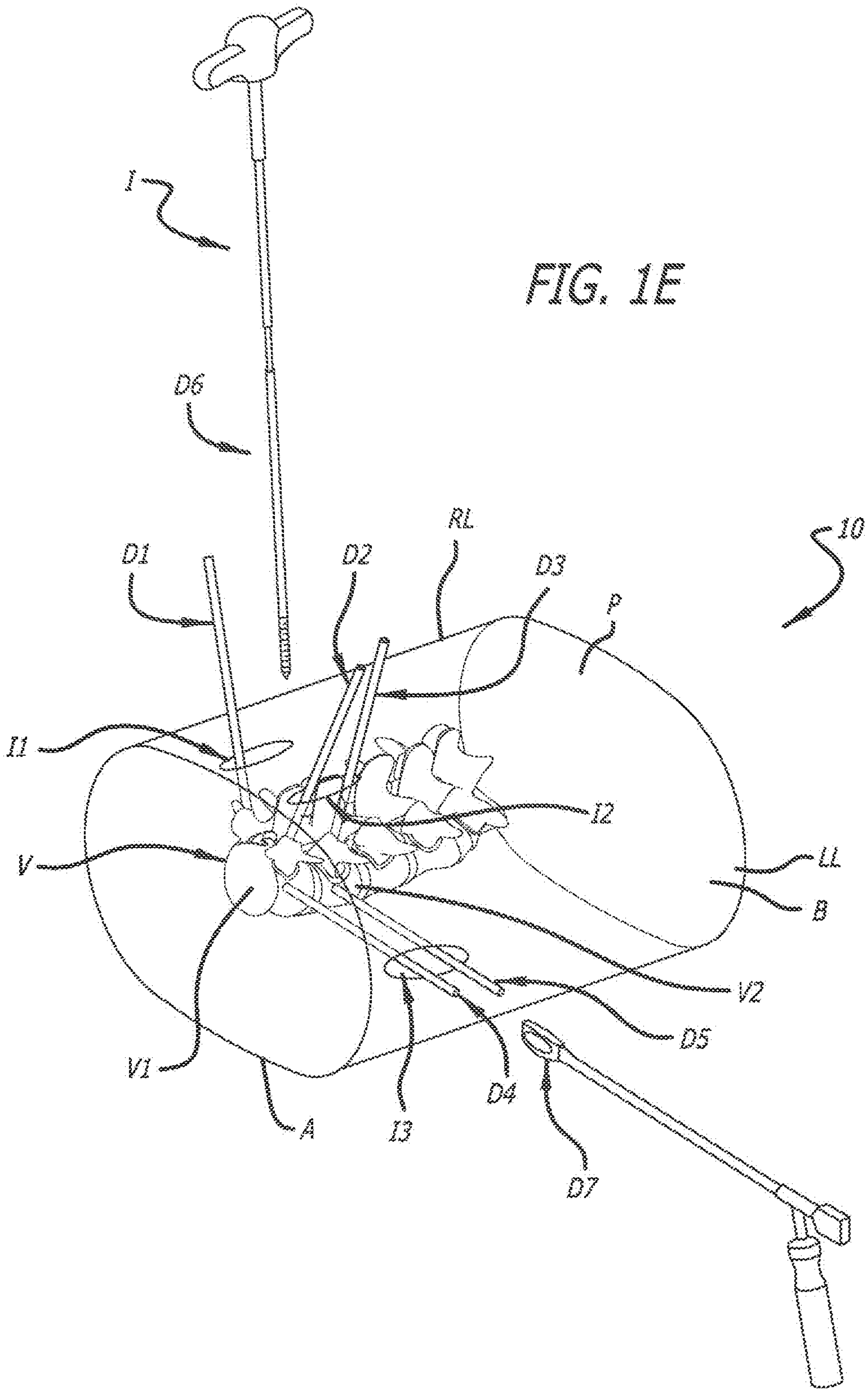
FIG. 1E is a top, perspective view of the portion of the spine shown in FIG. 1A depicting portions of the patient's abdomen shown in FIG. 1A, the first and second incisions shown in FIG. 1D, the third incision shown in FIG. 1D, a first device extending through the first incision using a posterior approach to engage a first vertebral body, a second device extending through the second incision using a posterior approach to engage the first vertebral body, a third device extending through the second incision using a posterior approach to engage a second vertebral body, a fourth device extending through the third incision using a lateral approach to engage the first vertebral body, and a fifth device extending through the third incision using a lateral approach to engage the second vertebral body.

As shown in FIG. 1E, for example, a first device D1, such as, for example, a Steinmann pin or a posted/extended screw, is inserted into first incision I1 such that first device D1 extends along the first surgical pathway using a posterior approach to engage first vertebral body V1 to the right of sagittal plane SP percutaneously. In some embodiments, first device D1 engages a portion of first vertebral body V1 between the articular process of first vertebral body V1 and the transverse process of first vertebral body V1. In some embodiments, a pilot hole is made in first vertebral body V1 for first device D1, and first device D1 is inserted into the pilot hole such that threads on an outer surface of first device D1 engage a portion of first vertebral body V1 that defines the pilot hole and first device D1 is rotated about a longitudinal axis defined by first device D1 until first device D1 threadingly engages first vertebral body V1. In some embodiments, first device D1 is threaded into first vertebral body V1 using a driver, such as, for example, a screw driver or an instrument I that engages a proximal end of first device D1. In some embodiments, first device D1 is threaded into first vertebral body V1 using a surgical drill, such as, for example, a drill and/or tap included in the POWEREASE™ System sold by Medtronic. Any of the above-mentioned drivers or instruments may be fitted with surgical navigation elements to establish and monitor the device D1 insertion trajectory intra-operatively, using a navigation and/or imaging system.

A second device D2, such as, for example, a Steinmann pin or a posted/extended screw, is inserted into second incision I2 (as shown in FIG. 1E) such that second device D2 extends along the second surgical pathway using a posterior approach to engage first vertebral body V1 to the left of sagittal plane SP percutaneously. In some embodiments, second device D2 engages a portion of first vertebral body V1 between the articular process of first vertebral body V1 and the transverse process of first vertebral body V1. In some embodiments, a pilot hole is made in first vertebral body V1 for second device D2, and second device D2 is inserted into the pilot hole such that threads on an outer surface of second device D2 engage a portion of first vertebral body V1 that defines the pilot hole and second device D2 is rotated about a longitudinal axis defined by second device D2 until second device D2 threadingly engages first vertebral body V1.

In some embodiments, second device D2 is threaded into first vertebral body V1 using a driver, such as, for example, a screw driver or an instrument I that engages a proximal end of second device D2. In some embodiments, second device D2 is threaded into first vertebral body V1 using a surgical drill, such as, for example, a drill and/or tap included in the POWEREASE™ System sold by Medtronic. In some embodiments, second device D2 is inserted into second incision I2 to engage first vertebral body V1 without moving the patient from a position in which first device D1 is inserted into first incision I1 to engage first vertebral body V1. That is, the patient is not moved or repositioned to insert second device D2 into second incision I2 to engage first vertebral body V1 after inserting first device D1 into first incision I1 to engage first vertebral body V1. In some embodiments, the patient's position is maintained between the insertion of first device D1 into first incision I1 to engage first vertebral body V1 and the insertion of second device D2 into second incision I2 to engage first vertebral body V1, at least in part, by a device, such as, for example, a surgical table, a surgical bed, cushions, wedges, etc. In some embodiments, the device is a dynamic surgical table system, such as, for example, that disclosed in U.S. Pat. No. 7,234,180, which is incorporated herein by reference, in its entirety. In some embodiments, the patient is maintained in a position such that coronal plane CP of body B is disposed at an angle α, such as, for example an acute angle relative to a floor F of the operating room, as shown in FIG. 1L, for example.

A third device D3, such as, for example, a Steinmann pin or a posted/extended screw, is inserted into second incision I2 (as shown in FIG. 1E) such that third device D3 extends along the second surgical pathway using a posterior approach to engage second vertebral body V2 to the left of sagittal plane SP percutaneously. In some embodiments, third device D3 engages a portion of second vertebral body V2 between the articular process of second vertebral body V2 and the transverse process of second vertebral body V2. In some embodiments, a pilot hole is made in second vertebral body V2 for third device D3, and third device D3 is inserted into the pilot hole such that threads on an outer surface of third device D3 engage a portion of second vertebral body V2 that defines the pilot hole and third device D3 is rotated about a longitudinal axis defined by third device D3 until third device D3 threadingly engages second vertebral body V2.

In some embodiments, third device D3 is threaded into second vertebral body V2 using a driver, such as, for example, a screw driver or an instrument I that engages a proximal end of third device D3. In some embodiments, third device D3 is threaded into second vertebral body V2 using a surgical drill, such as, for example, a drill and/or tap included in the POWEREASE™ System sold by Medtronic. In some embodiments, third device D3 is inserted into second incision I2 to engage second vertebral body V2 without moving the patient from a position in which first and second devices D1, D2 are inserted into first incision I1 and second incision I2, respectively, to engage first vertebral body V1. That is, the patient is not moved or repositioned to insert third device D3 into second incision I2 to engage second vertebral body V2 after inserting first and second devices D1, D2 into first incision I1 and second incision I2, respectively, to engage first vertebral body V1. In some embodiments, the patient's position is maintained between the insertion of first and second devices D1, D2 into first incision I1 and second incision I2, respectively, to engage first vertebral body V1 and the insertion of third device D3 into second incision I2 to engage second vertebral body V2, at least in part, by a device, such as, for example, a surgical table, a surgical bed, cushions, wedges, etc. In some embodiments, the device is a dynamic surgical table system, such as, for example, that disclosed in U.S. Pat. No. 7,234,180, which is incorporated herein by reference, in its entirety. In some embodiments, the patient is maintained in a position such that coronal plane CP of body B is disposed at an angle α, such as, for example an acute angle relative to a floor F of the operating room, as shown in FIG. 1L, for example.

A fourth device D4, such as, for example, a Steinmann pin or a posted/extended screw, is inserted into third incision I3 (as shown in FIG. 1E) such that fourth device D4 extends along the third surgical pathway using a lateral approach to engage first vertebral body V1 to the left of sagittal plane SP percutaneously. In some embodiments, a pilot hole is made in first vertebral body V1 for fourth device D4, and fourth device D4 is inserted into the pilot hole such that threads on an outer surface of fourth device D4 engage a portion of first vertebral body V1 that defines the pilot hole and fourth device D4 is rotated about a longitudinal axis defined by fourth device D4 until fourth device D4 threadingly engages first vertebral body V1.

In some embodiments, fourth device D4 is threaded into first vertebral body V1 using a driver, such as, for example, a screw driver or an instrument I that engages a proximal end of fourth device D4. In some embodiments, fourth device D4 is threaded into first vertebral body V1 using a surgical drill, such as, for example, a drill and/or tap included in the POWEREASE™ System sold by Medtronic. In some embodiments, fourth device D4 is inserted into third incision I3 to engage first vertebral body V1 without moving the patient from a position in which first, second and third devices D1, D2, D3 are inserted into first and second incisions I1, I2 to engage first and second vertebral bodies V1, V2. That is, the patient is not moved or repositioned to insert fourth device D4 into third incision I3 to engage first vertebral body V1 after inserting first, second and third device D1, D2, D3 into first and second incisions I1, I2 to engage first and second vertebral bodies V1, V2. In some embodiments, the patient's position is maintained between the insertion of first, second and third devices D1, D2, D3 into first and second incisions I1, I2 to engage first and second vertebral bodies V1, V2, and the insertion of fourth device D4 into third incision I3 to engage first vertebral body V1, at least in part, by a device, such as, for example, a surgical table, a surgical bed, cushions, wedges, etc. In some embodiments, the device is a dynamic surgical table system, such as, for example, that disclosed in U.S. Pat. No. 7,234,180, which is incorporated herein by reference, in its entirety. In some embodiments, the patient is maintained in a position such that coronal plane CP of body B is disposed at an angle α, such as, for example an acute angle relative to a floor F of the operating room, as shown in FIG. 1L, for example.

A fifth device D5, such as, for example, a Steinmann pin or a posted/extended screw, is inserted into third incision I3 (as shown in FIG. 1E) such that fifth device D5 extends along the third surgical pathway using a lateral approach to engage second vertebral body V2 to the left of sagittal plane SP percutaneously. In some embodiments, a pilot hole is made in second vertebral body V2 for fifth device D5, and fifth device D5 is inserted into the pilot hole such that threads on an outer surface of fifth device D5 engage a portion of second vertebral body V2 that defines the pilot hole and fifth device D5 is rotated about a longitudinal axis defined by fifth device D5 until fifth device D5 threadingly engages second vertebral body V2.

In some embodiments, fifth device D5 is threaded into second vertebral body V2 using a driver, such as, for example, a screw driver or an instrument I that engages a proximal end of fifth device D5. In some embodiments, fifth device D5 is threaded into second vertebral body V2 using a surgical drill, such as, for example, a drill and/or tap included in the POWEREASE™ System sold by Medtronic. In some embodiments, fifth device D5 is inserted into third incision I3 to engage second vertebral body V2 without moving the patient from a position in which first, second, third and fourth devices D1, D2, D3, D4 are inserted into first, second and third incisions I1, I2, I3 to engage first and second vertebral bodies V1, V2. That is, the patient is not moved or repositioned to insert fifth device D5 into third incision I3 to engage second vertebral body V2 after inserting first, second, third and fourth devices D1, D2, D3, D4 into first, second and third incisions I1, I2, 13 to engage first and second vertebral bodies V1, V2. In some embodiments, the patient's position is maintained between the insertion of first, second, third and fourth devices D1, D2, D3, D4 into first, second and third incisions I1, I2, I3 to engage first and second vertebral bodies V1, V2, and the insertion of fifth device D5 into third incision I3 to engage second vertebral body V2, at least in part, by a device, such as, for example, a surgical table, a surgical bed, cushions, wedges, etc. In some embodiments, the device is a dynamic surgical table system, such as, for example, that disclosed in U.S. Pat. No. 7,234,180, which is incorporated herein by reference, in its entirety. In some embodiments, the patient is maintained in a position such that coronal plane CP of body B is disposed at an angle α, such as, for example an acute angle relative to a floor F of the operating room, as shown in FIG. 1L, for example.

A sixth device D6, such as, for example, a Steinmann pin or a posted/extended screw, is inserted into first incision I1 (as shown in FIG. 1E) such that sixth device D6 extends along the first surgical pathway using a posterior approach to engage second vertebral body V2 to the right of sagittal plane SP percutaneously. In some embodiments, sixth device D6 engages a portion of second vertebral body V2 between the articular process of second vertebral body V2 and the transverse process of second vertebral body V2. In some embodiments, a pilot hole is made in second vertebral body V2 for sixth device D6, and sixth device D6 is inserted into the pilot hole such that threads on an outer surface of sixth device D6 engage a portion of second vertebral body V2 that defines the pilot hole and sixth device D6 is rotated about a longitudinal axis defined by sixth device D6 until sixth device D6 threadingly engages second vertebral body V2.

In some embodiments, sixth device D6 is threaded into second vertebral body V2 using a driver, such as, for example, a screw driver or an instrument I that engages a proximal end of sixth device D6. In some embodiments, sixth device D6 is threaded into second vertebral body V2 using a surgical drill, such as, for example, a drill and/or tap included in the POWEREASE™ System sold by Medtronic. In some embodiments, sixth device D6 is inserted into first incision I1 to engage second vertebral body V2 without moving the patient from a position in which first, second, third, fourth and fifth devices D1, D2, D3, D4, D5 are inserted into first, second and third incisions I1, I2, I3 to engage first and second vertebral bodies V1, V2. That is, the patient is not moved or repositioned to insert sixth device D6 into first incision I1 to engage second vertebral body V2 after inserting first, second, third, fourth and fifth devices D1, D2, D3, D4, D5 into first, second and third incisions I1, I2, I3 to engage first and second vertebral bodies V1, V2. In some embodiments, the patient's position is maintained between the insertion of first, second, third, fourth and fifth devices D1, D2, D3, D4, D5 into first, second and third incisions I1, I2, 13 to engage first and second vertebral bodies V1, V2, and the insertion of sixth device D6 into first incision I1 to engage second vertebral body V2, at least in part, by a device, such as, for example, a surgical table, a surgical bed, cushions, wedges, etc. In some embodiments, the device is a dynamic surgical table system, such as, for example, that disclosed in U.S. Pat. No. 7,234,180, which is incorporated herein by reference, in its entirety. In some embodiments, the patient is maintained in a position such that coronal plane CP of body B is disposed at an angle α, such as, for example an acute angle relative to a floor F of the operating room, as shown in FIG. 1L, for example.

In some embodiments, first, second and fourth devices D1, D2, D4 are moved relative to third, fifth and sixth devices D3, D5, D6 to move the position of first vertebral body V1 relative to second vertebral body V2. In some embodiments, first, second and fourth devices D1, D2, D4 are moved relative to third, fifth and sixth devices D3, D5, D6 to separate first vertebral body V1 from second vertebral body V2 in a manner that creates a space for a seventh device D7, such as, for example, an interbody implant, an expandable interbody implant, a trial implant, an expandable trial (such as the Medtronic Spine SCISSOR JACK® distractor), an inflatable implant or one or more Fernstrom balls. In some embodiments, as shown in FIG. 1M, for example, first device D1 is separated from sixth device D6 by a first gap G1 and second device D2 is separated from third device D3 by a second gap G2, first device D1 is drawn toward sixth device D6 and/or sixth device D6 is drawn toward first device D1 to reduce the width of first gap G1, and second device D2 is drawn toward third device D3 and/or third device D3 is drawn toward second device D2 to reduce the width of second gap G2. Reducing the widths of first and second gaps G1, G2 decreases separation of first vertebral body V1 and second vertebral body V2 in portion P, and creates greater separation between first vertebral body V1 and second vertebral body V2 in portions A, RL, LL to facilitate insertion of seventh device D7.

Figure 1F:
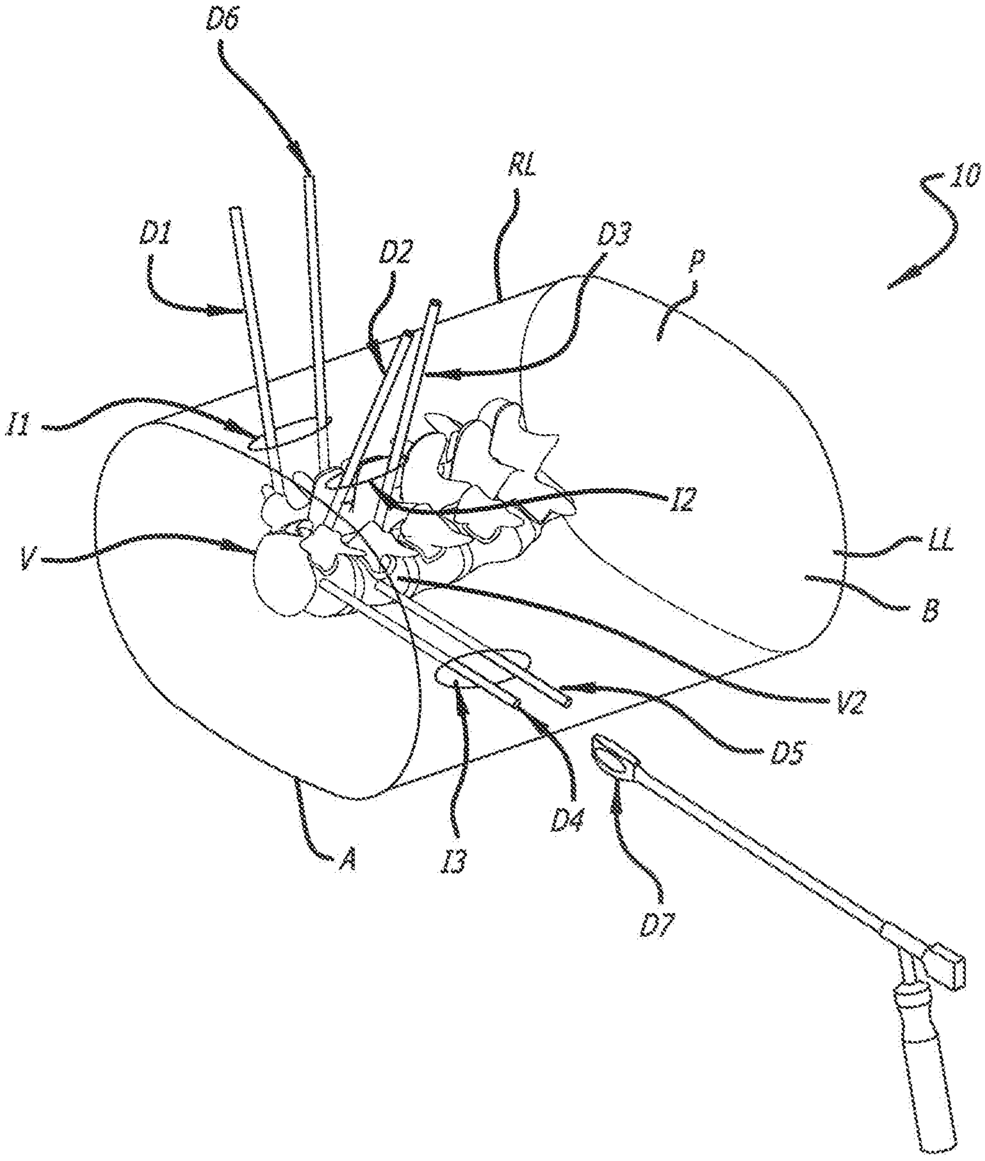
FIG. 1F is a top, perspective view of the portion of the spine shown in FIG. 1A depicting portions of the patient's abdomen shown in FIG. 1A, the first and second incisions shown in FIG. 1D, the third incision shown in FIG. 1D, the first device shown in FIG. 1E extending through the first incision using a posterior approach to engage the first vertebral body, the second device shown in FIG. 1E extending through the second incision using a posterior approach to engage the first vertebral body, the third device shown in FIG. 1E extending through the second incision using a posterior approach to engage the second vertebral body, the fourth device shown in FIG. 1E extending through the third incision using a lateral approach to engage the first vertebral body, the fifth device shown in FIG. 1E extending through the third incision using a lateral approach to engage the second vertebral body, and a sixth device extending through the first incision using a posterior approach to engage the second vertebral body.
Figure 1G:
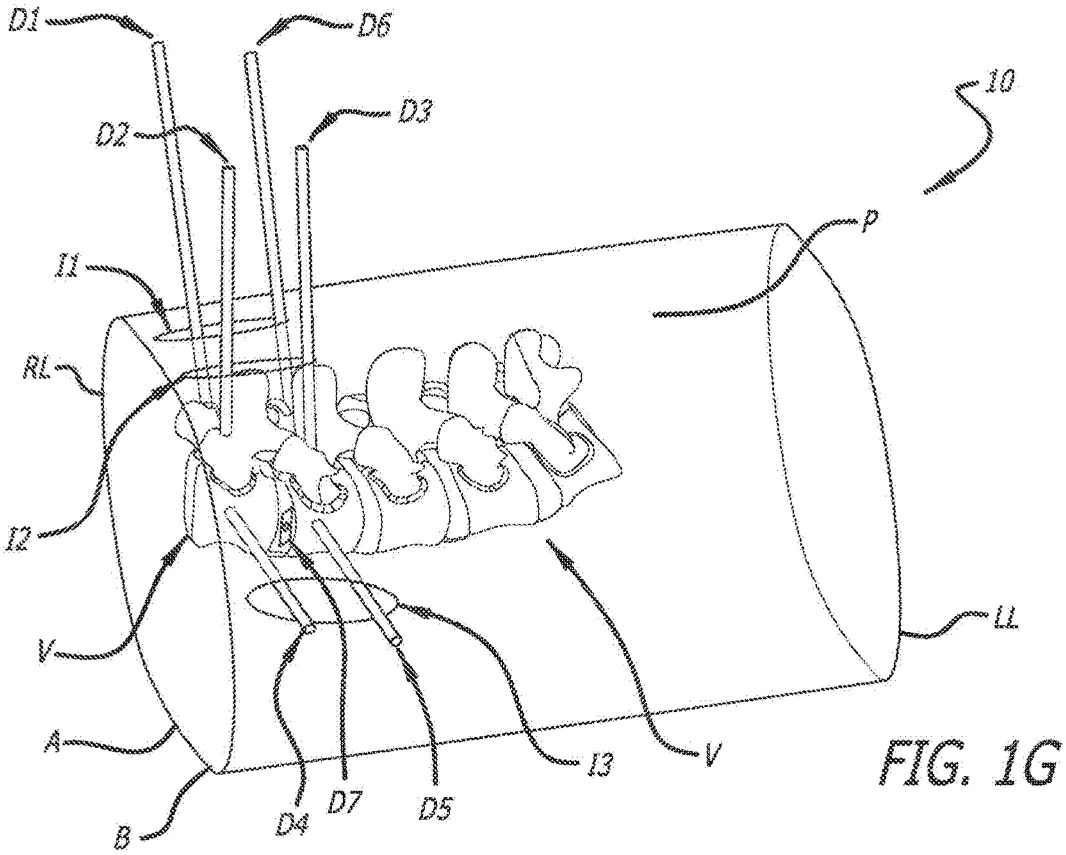
FIG. 1G is a side, perspective view of the portion of the spine shown in FIG. 1A depicting portions of the patient's abdomen shown in FIG. 1A, the first and second incisions shown in FIG. 1D, the third incision shown in FIG. 1D, the first device shown in FIG. 1E extending through the first incision using a posterior approach to engage the first vertebral body, the second device shown in FIG. 1E extending through the second incision using a posterior approach to engage the first vertebral body, the third device shown in FIG. 1E extending through the second incision using a posterior approach to engage the second vertebral body, the fourth device shown in FIG. 1E extending through the third incision using a lateral approach to engage the first vertebral body, the fifth device shown in FIG. 1E extending through the third incision using a lateral approach to engage the second vertebral body, and the sixth device shown in FIG. 1F extending through the first incision using a posterior approach to engage the second vertebral body.
Figure 1H:
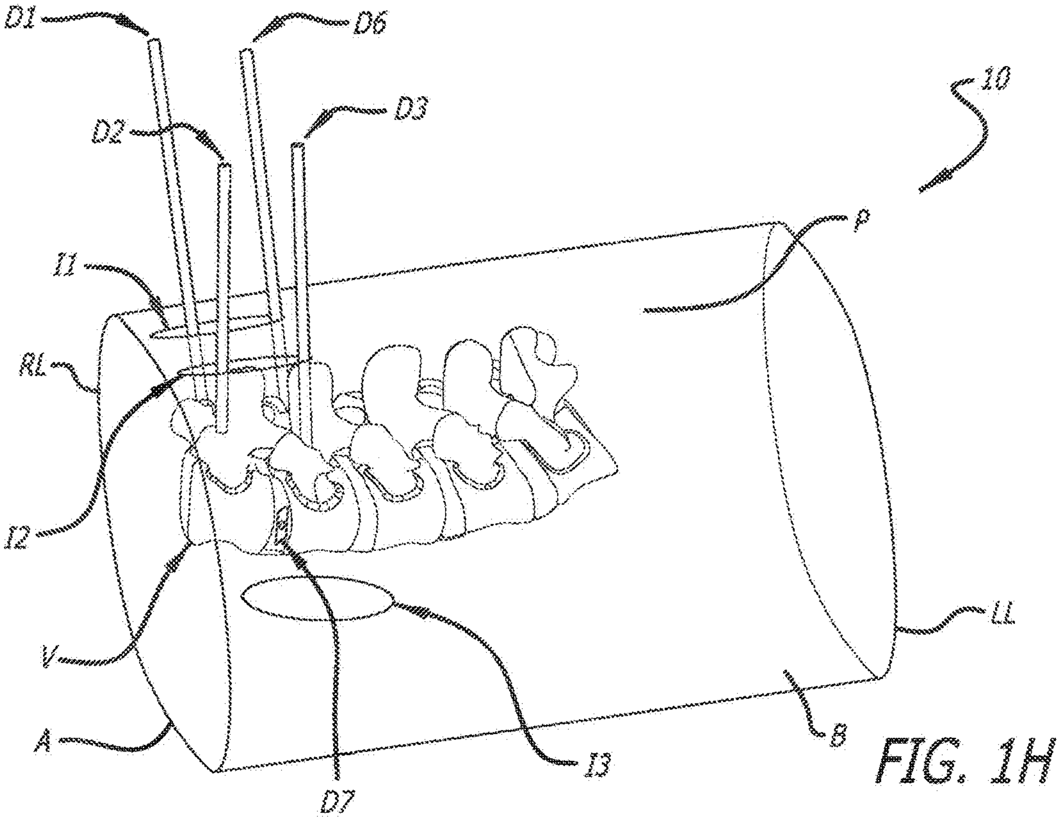
FIG. 1H is a side, perspective view of the portion of the spine shown in FIG. 1A depicting portions of the patient's abdomen shown in FIG. 1A, the first and second incisions shown in FIG. 1D, the third incision shown in FIG. 1D, the first device shown in FIG. 1E extending through the first incision using a posterior approach to engage the first vertebral body, the second device shown in FIG. 1E extending through the second incision using a posterior approach to engage the first vertebral body, the third device shown in FIG. 1E extending through the second incision using a posterior approach to engage the second vertebral body, and the sixth device shown in FIG. 1F extending through the first incision using a posterior approach to engage the second vertebral body, the fourth device shown in FIG. 1E and the fifth device shown in FIG. 1E having been removed from the first and second vertebral bodies through the third incision.
Figure 1I:
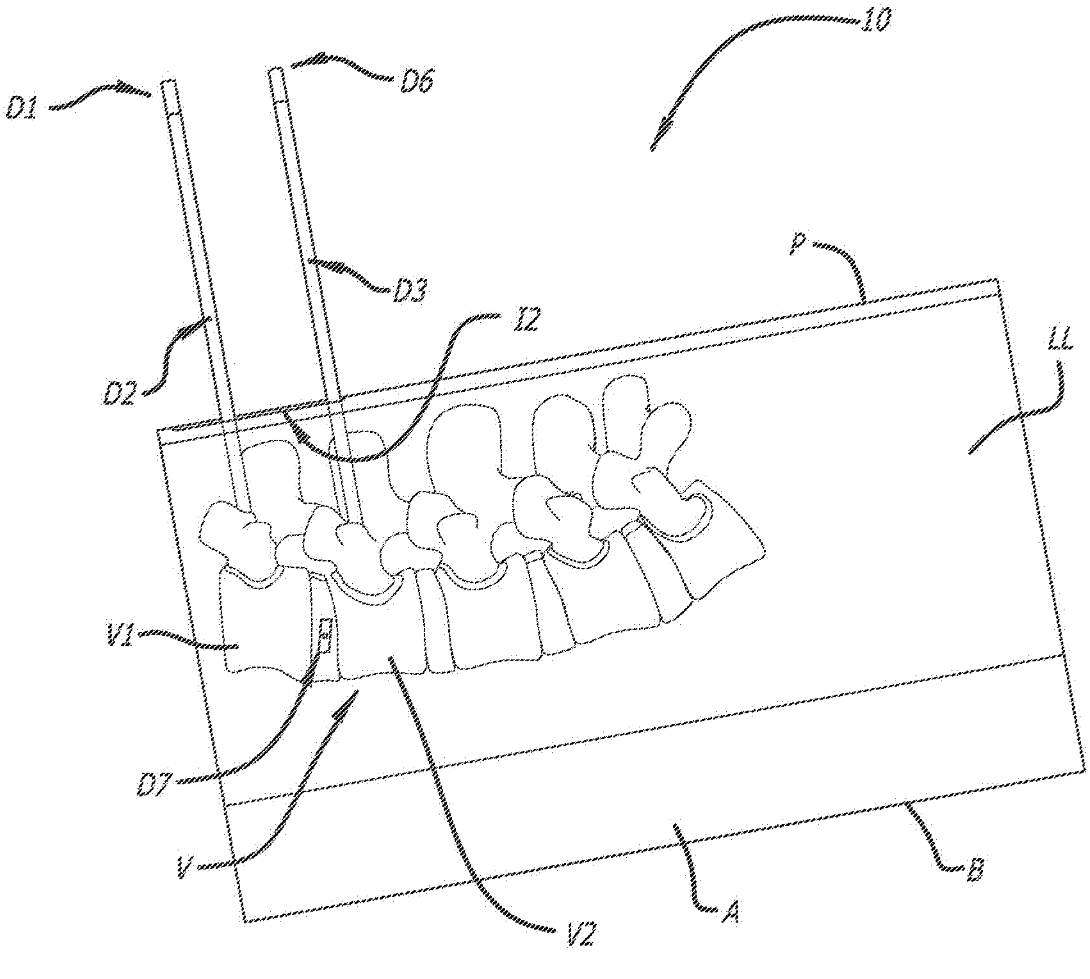
FIG. 1I is a side view of the portion of the spine shown in FIG. 1A depicting patient's abdomen shown in FIG. 1A, the second device shown in FIG. 1E extending through the second incision using a posterior approach to engage the first vertebral body, the third device shown in FIG. 1E extending through the second incision using a posterior approach to engage the second vertebral body, and an interbody implant positioned between the first and second vertebral bodies.
Figure 1J:
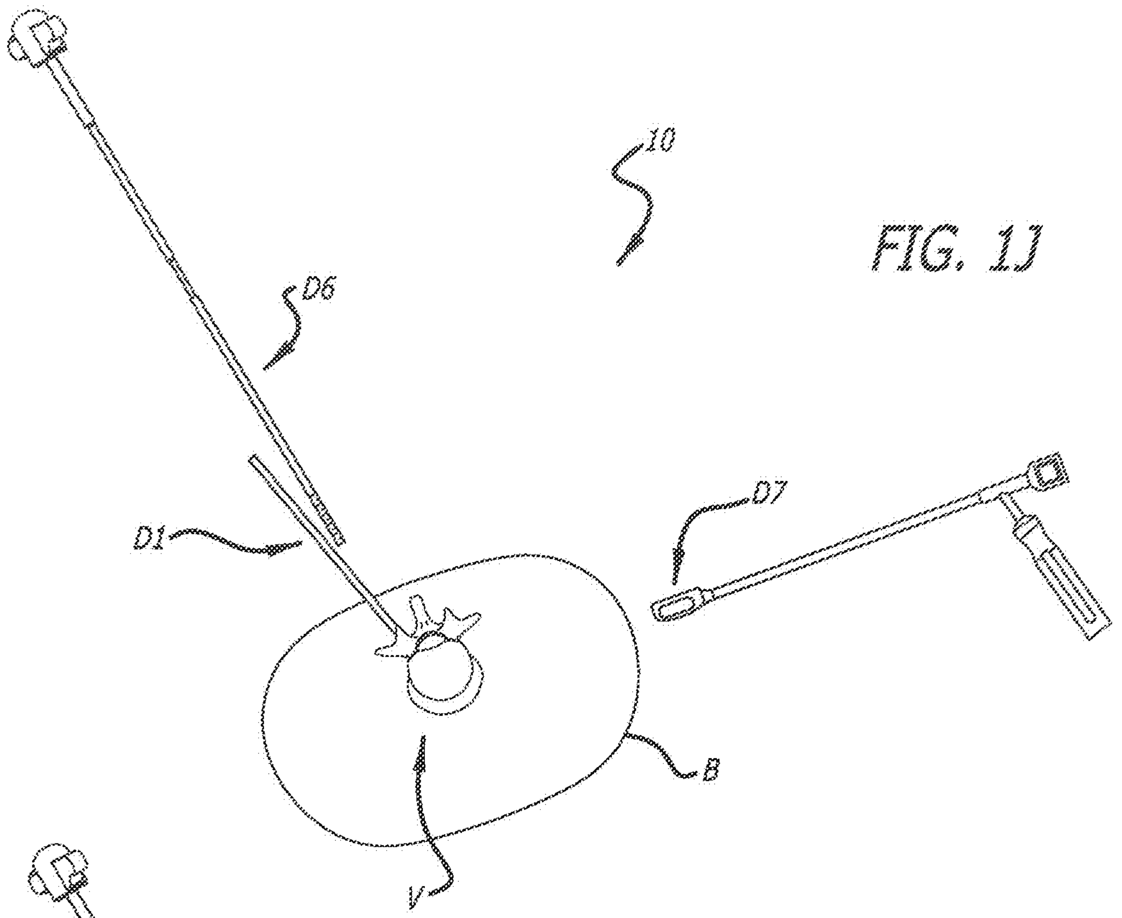
FIG. 1J is a top view of the patient's abdomen shown in FIG. 1A showing positioning of the patient's abdomen as the first device shown in FIG. 1E is inserted through the first incision using a posterior approach to engage the first vertebral body, and the sixth device shown in FIG. 1F is inserted through the first incision using a posterior approach to engage the second vertebral body.
Figure 1K:
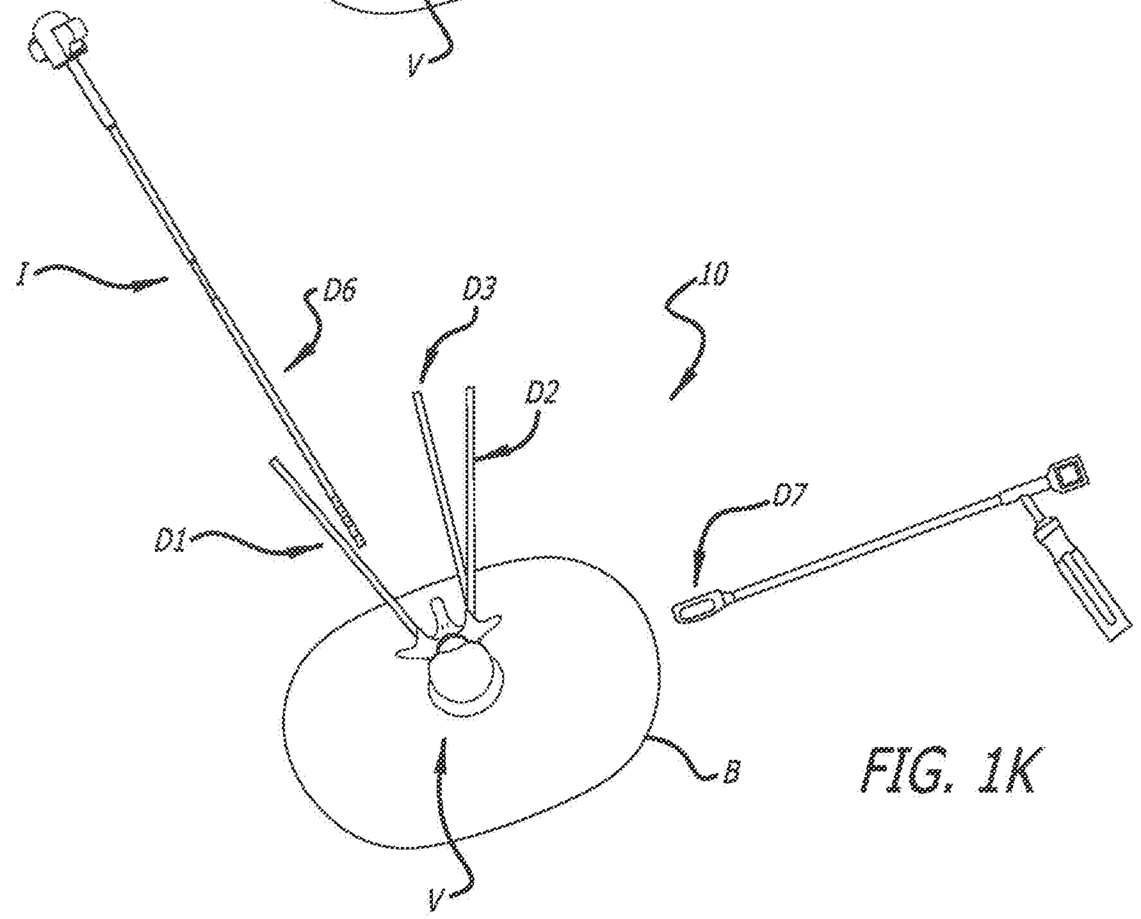
FIG. 1K is a top view of the patient's abdomen shown in FIG. 1A showing positioning of the patient's abdomen as the first device shown in FIG. 1E is inserted through the first incision using a posterior approach to engage the first vertebral body, the second device shown in FIG. 1E is inserted through the second incision using a posterior approach to engage the first vertebral body, the third device shown in FIG. 1E is inserted through the second incision using a posterior approach to engage the second vertebral body, and the sixth device shown in FIG. 1F is inserted through the first incision using a posterior approach to engage the second vertebral body.
Figure 1N:
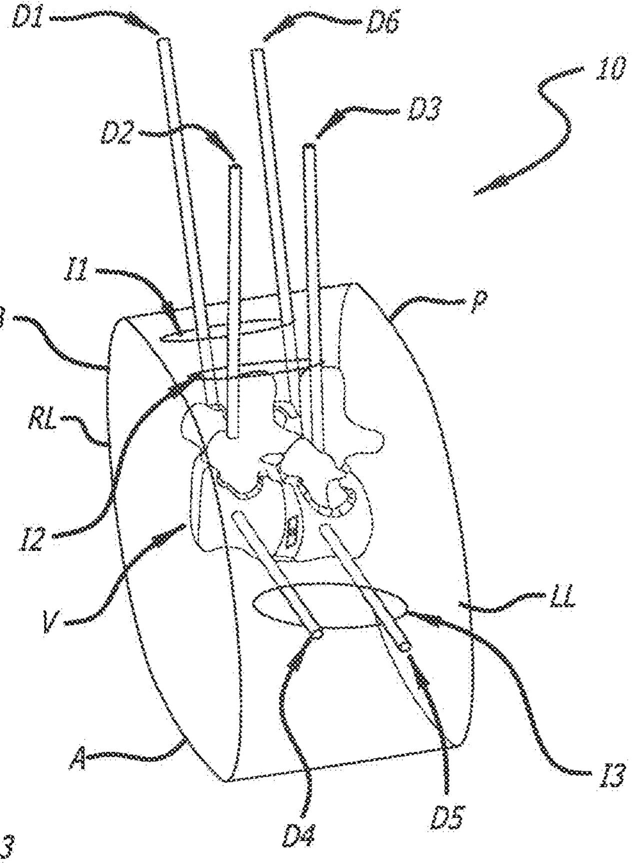
FIG. 1N is a side, perspective view of portions of the spine shown in FIG. 1A depicting portions of the patient's abdomen shown in FIG. 1A, the first and second incisions shown in FIG. 1D, the third incision shown in FIG. 1D, the first device shown in FIG. 1E extending through the first incision using a posterior approach to engage the first vertebral body, the second device shown in FIG. 1E extending through the second incision using a posterior approach to engage the first vertebral body, the third device shown in FIG. 1E extending through the second incision using a posterior approach to engage the second vertebral body, the fourth device shown in FIG. 1E extending through the third incision using a lateral approach to engage the first vertebral body, the fifth device shown in FIG. 1E extending through the third incision using a lateral approach to engage the second vertebral body, and the sixth device shown in FIG. 1F extending through the first incision using a posterior approach to engage the second vertebral body.

Seventh device D7 is inserted into third incision I3 such that seventh device D7 extends along the third surgical pathway using a lateral approach to position seventh device D7 in the space between first vertebral body V1 and second vertebral body V2 percutaneously, as shown in FIG. 1G, for example. In some embodiments, seventh device D7 is inserted into third incision I3 for positioning in the space between first vertebral body V1 and second vertebral body V2 without moving the patient from a position in which first, second, third, fourth, fifth and sixth devices D1, D2, D3, D4, D5, D6 are inserted into first, second and third incisions I1, I2, I3 to engage first and second vertebral bodies V1, V2. That is, the patient is not moved or repositioned to insert seventh device D7 into third incision I3 for positioning in the space between first vertebral body V1 and second vertebral body V2 after inserting first, second, third, fourth, fifth and sixth devices D1, D2, D3, D4, D5, D6 into first and second incisions I1, I2 to engage first and second vertebral bodies V1, V2. In some embodiments, fourth and fifth devices D4, D5 are removed after device D7 is positioned in the space between first vertebral body V1 and second vertebral body V2, as shown in FIG. 1H, for example.

Figure 1O:
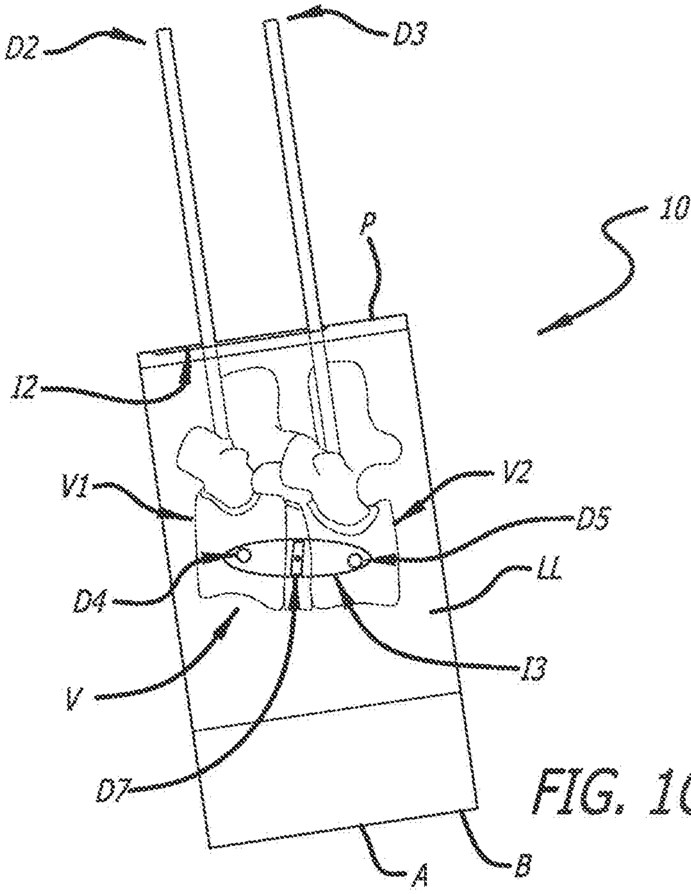
FIG. 1O is a side view of portions of the spine shown in FIG. 1A depicting portions of the patient's abdomen shown in FIG. 1A, the second device shown in FIG. 1E extending through the second incision using a posterior approach to engage the first vertebral body, the third device shown in FIG. 1E extending through the second incision using a posterior approach to engage the second vertebral body, and an interbody implant positioned between the first and second vertebral bodies.
Figure 1P:
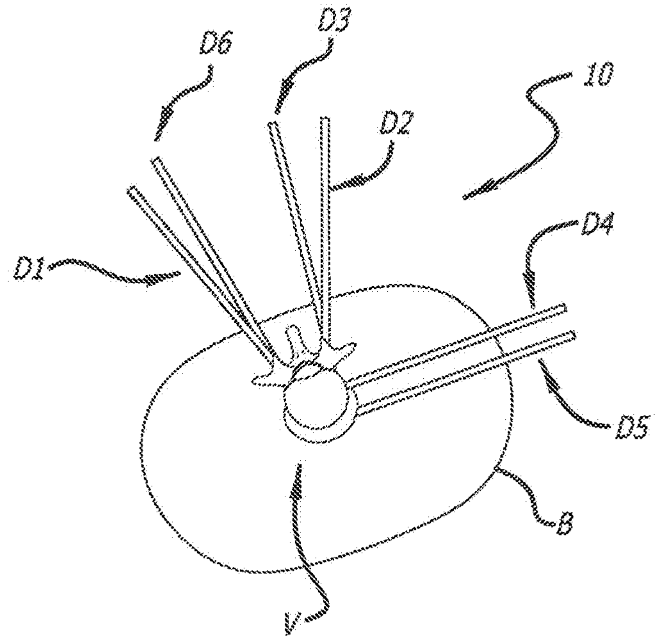
FIG. 1P is a top view of the patient's abdomen shown in FIG. 1A showing positioning of the patient's abdomen as the first device shown in FIG. 1E is inserted through the first incision using a posterior approach to engage the first vertebral body, the second device shown in FIG. 1E is inserted through the second incision using a posterior approach to engage the first vertebral body, the third device shown in FIG. 1E is inserted through the second incision using a posterior approach to engage the second vertebral body, the fourth device shown in FIG. 1E is inserted through the third incision using a lateral approach to engage the first vertebral body, the fifth device shown in FIG. 1E is inserted through the third incision using a lateral approach to engage the second vertebral body, and the sixth device shown in FIG. 1F is inserted through the first incision using a posterior approach to engage the second vertebral body.

In one embodiment, shown in FIG. 1O, devices D4, D5 are inserted through third incision I3 after device D7 is positioned in the space between first vertebral body V1 and second vertebral body V2. That is, first, second, third and sixth devices D1, D2, D3, D6 are inserted through first and second incisions I1, I2 to engage first and second vertebral bodies V1, V2 in the manner discussed above. First and second devices D1, D2 are moved relative to third and sixth devices D3, D6 to move first vertebral body V1 relative to second vertebral body V2 to create a space between first vertebral body V1 and second vertebral body V2 for seventh device D7. Seventh device D7 is inserted into the space between first vertebral body V1 and second vertebral body V2 through third incision I3 in the manner discussed above. Fourth and fifth devices D4, D5 are inserted through third incision I3 in the manner discussed above until fourth and fifth devices D4, D5 extend through first and second vertebral bodies V1, V2 and into seventh device D7.

In some embodiments, first, second, third and sixth devices D1, D2, D3, D6 are used as fiducial pins and/or surgical landmarks for reference in navigating or enabling robotic surgical procedures.

Figure 1Q:
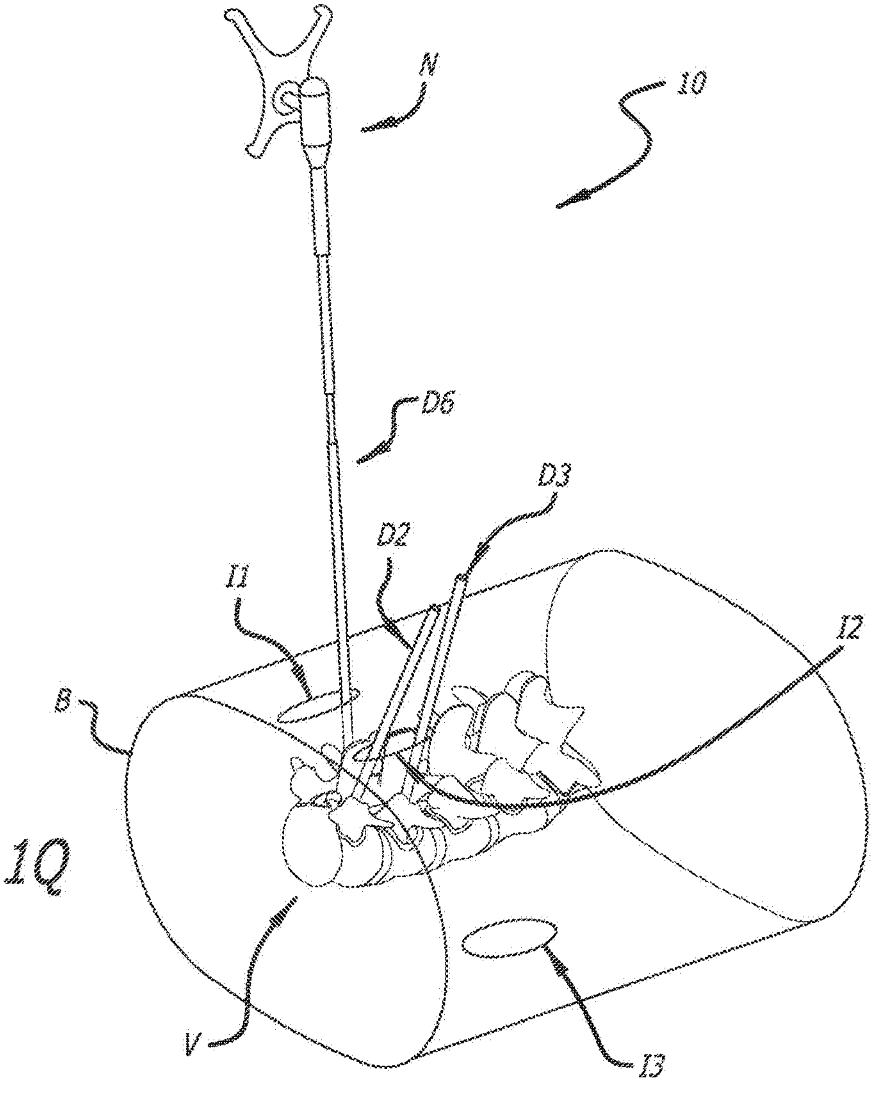
FIG. 1Q is a top, perspective view of portions of the spine shown in FIG. 1A depicting portions of the patient's abdomen shown in FIG. 1A, the first and second incisions shown in FIG. 1D, the third incision shown in FIG. 1D, the second device shown in FIG. 1E extending through the second incision using a posterior approach to engage the first vertebral body, the third device shown in FIG. 1E extending through the second incision using a posterior approach to engage the second vertebral body, and the sixth device shown in FIG. 1F extending through the first incision using a posterior approach to engage the second vertebral body, where the sixth device is guided into position using a navigational tool.

In one embodiment, shown in FIG. 1Q, at least one of first, second, third, fourth, fifth, sixth and seventh devices D1, D2, D3, D4, D5, D6, D7 are inserted into body B using an instrument, such as, for example, instrument N having integrated neuromonitoring and/or navigation capabilities. In some embodiments, instrument N is used to establish and/or monitor the trajectories of at least one of first, second, third, fourth, fifth, sixth and seventh devices D1, D2, D3, D4, D5, D6, D7. That is, instrument N may be used to determine and/or select a safe trajectory in relation to the patient's anatomy for at least one of first, second, third, fourth, fifth, sixth and seventh devices D1, D2, D3, D4, D5, D6, D7, even as that anatomy shifts in real-time and/or ensure that at least one of first, second, third, fourth, fifth, sixth and seventh devices D1, D2, D3, D4, D5, D6, D7 is being inserted and/or implanted using the selected trajectory. In some embodiments, instrument N is part of a navigation system sold by Medtronic, such as, for example, StealthStation® S7®, StealthStation i7™ StealthStation iNav®, AxiEM Electromagnetic Navigation System, Fusion™ ENT and/or StealthViz™ Planning Station. In some embodiments, use of instrument N and/or another instrument having integrated neuromonitoring and/or navigation capabilities aids a medical practitioner to perform safer, more precise procedure, reduce procedure invasiveness and risk and/or improve patient outcomes and recovery.

In some embodiments, imaging is used to establish and/or monitor the trajectories of at least one of first, second, third, fourth, fifth, sixth and seventh devices D1, D2, D3, D4, D5, D6, D7 through incisions I1, I2, I3 using the approaches discussed above. In one embodiment, an imaging system, such as, for example, the O-arm Surgical Imaging System available from Medtronic is used to establish and/or monitor the trajectories of at least one of first, second, third, fourth, fifth, sixth and seventh devices D1, D2, D3, D4, D5, D6, D7 using intra-operative imaging. The O-arm Surgical Imaging System, among other things, provides fast access to real-time, multi-plane 3D images (and 2D images), provides full support of the unique workflow of procedures, such as, for example, spinal procedures, minimizes radiation dose for surgical staff (by reducing X-ray exposure, for example) and provides visualization to confirm hardware therapy placement, potentially eliminating revision surgeries.

In some embodiments, fourth device D4 intersects at least one of first device D1 and second device D2 such that fourth device D4 extends through at least one of first device D1 and second device D2. That is, at least one of first device D1 and second device D2 includes a threaded shaft configured to penetrate tissue, such as, for example, bone, where at least one aperture extends through the threaded shaft such that the aperture(s) extend(s) transverse to a longitudinal axis defined by first device D1 or second device D2. A shaft of fourth device D4 extends through one of the apertures in first device D1 and/or one of the apertures in second device D2. In some embodiments, first device D1, second device D2 and fourth device D4 are similar in structure and/or function to the components of the cannulated and fenestrated bone fastener disclosed in U.S. patent application Ser. No. 13/446,347, which is incorporated herein by reference, in its entirety.

In some embodiments, fifth device D5 intersects at least one of sixth device D6 and third device D3 such that fifth device D5 extends through at least one of sixth device D6 and third device D3. That is, at least one of sixth device D6 and third device D3 includes a threaded shaft configured to penetrate tissue, such as, for example, bone, where at least one aperture extends through the threaded shaft such that the aperture(s) extend(s) transverse to a longitudinal axis defined by sixth device D6 or third device D3. A shaft of fifth device D5 extends through one of the apertures in sixth device D6 and/or one of the apertures in third device D3. In some embodiments, third device D3, fifth device D5 and sixth device D6 are similar in structure and/or function to the components of the cannulated and fenestrated bone fastener disclosed in U.S. patent application Ser. No. 13/446,347, which is incorporated herein by reference, in its entirety.

In some embodiments, at least one of first, second, third, fourth, fifth and sixth devices D1, D2, D3, D4, D5, D6 are fixed to at least another one of first, second, third, fourth, fifth and sixth devices D1, D2, D3, D4, D5, D6. In some embodiments, at least one of first, second, third, fourth, fifth and sixth devices D1, D2, D3, D4, D5, D6 are fixed to a surgical bed, such as, for example, a frame of a surgical bed. In some embodiments, at least one of first, second, third, fourth, fifth and sixth devices D1, D2, D3, D4, D5, D6 is used to manipulate vertebrae V to correct deformities while at least one of first, second, third, fourth, fifth and sixth devices D1, D2, D3, D4, D5, D6 is used to distract the space between first vertebral body V1 and second vertebral body V2 to create a space for seventh device D7 in the manner described above.

In some embodiments, at least one of first, second, third, fourth, fifth and sixth devices D1, D2, D3, D4, D5, D6 is cannulated and/or fenestrated nail or tube. In some embodiments, at least one of first, second, third, fourth, fifth and sixth devices D1, D2, D3, D4, D5, D6 is a cannulated and/or fenestrated screw. In some embodiments, where at least one of first, second, third, fourth, fifth and sixth devices D1, D2, D3, D4, D5, D6 is a screw, the thread on the screw may comprise the OSTEOGRIP® thread pattern available from Medtronic, having a varying pitch and/or thread-count in order to optimize screw purchase in bony structures having layers of hard cortical bone and softer cancellous bone. In some embodiments, a guide wire is inserted to guide at least one of first, second, third, fourth, fifth and sixth devices D1, D2, D3, D4, D5, D6. That is, at least one guide wire is inserted into first vertebral body V1 and/or second vertebral body V2. One of the guidewires is inserted into the cannula of one of first, second, third, fourth, fifth and sixth devices D1, D2, D3, D4, D5, D6. First, second, third, fourth, fifth and sixth devices D1, D2, D3, D4, D5, D6 are then slid along the guidewires to engage first, second, third, fourth, fifth and sixth devices D1, D2, D3, D4, D5, D6 in the manner described above.

In some embodiments, at least one of first, second, third, fourth, fifth and sixth devices D1, D2, D3, D4, D5, D6 is a cannulated screw without fenestrations and/or a cannulated screw having at least one lateral fenestration that is in communication with the cannula, such as, for example, that disclosed in U.S. Pat. No. 6,565,572 and/or U.S. patent application Ser. No. 13/397,316, which are each incorporated herein by reference, in their entireties. In some embodiments, a material is introduced through the cannulae and/or fenestrations of at least one of first, second, third, fourth, fifth and sixth devices D1, D2, D3, D4, D5, D6 to deliver the material to first vertebral body V1 and/or second vertebral body V2. In some embodiments, the material is bone cement, a bone growth material, such as, for example, bone morphogenetic protein (BMP), an analgesic and/or an anti-inflammatory agent. In some embodiments, an instrument is introduced through the cannulae and/or fenestrations of at least one of first, second, third, fourth, fifth and sixth devices D1, D2, D3, D4, D5, D6 to provide navigational capabilities and/or stimulate bone growth. In some embodiments, the instrument is a probe and/or electrodes.

Figure 2A:
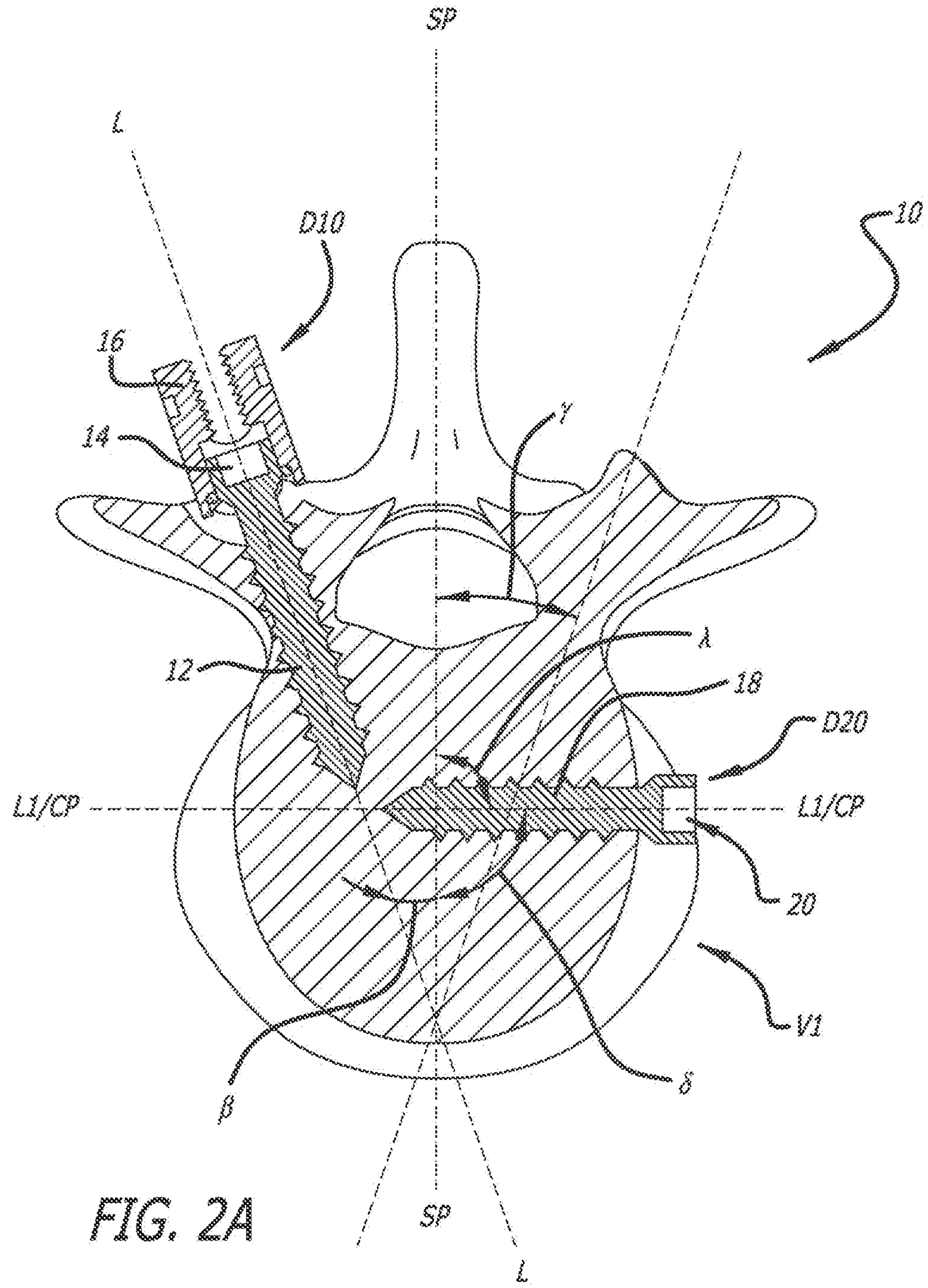
FIG. 2A is a top view, in part cross section, of a vertebral body of a patient including a first device that is inserted through a first incision using a posterior approach to engage the vertebral body, and a second device that is inserted through a second incision using a lateral approach to engage the vertebral body, where the first and second devices are each bone screws that are in the same plane and the first device is spaced apart from the second device.

In one embodiment, shown in FIG. 2A, a first device D10, such as, for example, a bone screw, is positioned through a first surgical pathway using a posterior approach to engage a first vertebral body V1 to the right of sagittal plane SP percutaneously. In some embodiments, first device D10 engages a portion of first vertebral body V1 between the articular process of vertebral body V1 and the transverse process of first vertebral body V1. In some embodiments, a pilot hole is made in first vertebral body V1 for first device D10 and first device D10 is inserted into the pilot hole such that threads on the outer surface of a shaft 12 of first device D10 engage a portion of first vertebral body V1 that define the pilot hole and first device D10 is rotated about a longitudinal axis L defined by shaft 12 until first device D10 threadingly engages first vertebral body V1. In some embodiments, first device D10 is threaded into the pilot hole and/or first vertebral body V1 using an instrument, such as, for example, a driver that engages a tool engaging portion 14 of shaft 12. In some embodiments, first device D10 is threaded into first vertebral body V1 using a surgical drill, such as, for example, a drill and/or tap included in the POWEREASE™ System sold by Medtronic. In some embodiments, first device D10 includes receiver 16 that is rotatably coupled to shaft 12. Receiver 16 comprises a pair of arms defining an implant cavity, such as, for example a U-shaped implant cavity (such as the "tulip head" of a multi-axial screw (MAS) available as part of the Medtronic CD HORIZON® SOLERA® spinal implant system) configured for disposal of a connecting element, such as, for example, a surgical rod. In some embodiments, first device D10 is inserted into first vertebral body V1 such that longitudinal axis L extends at an angle β relative to sagittal plane SP. In some embodiments, angle β is an acute angle. In some embodiments, angle β is an angle between about 1 and 45 degrees. In some embodiments, shaft 12 can be variously configured, such as, for example, smooth, ringed and/or have various cross sectional configurations, such as, for example, square, polygonal or round. In some embodiments, receiver 16 is fixed to shaft such that first device D10 is a monoaxial or uniaxial screw.

In some embodiments, first device D10 is positioned through the first surgical pathway using a posterior approach to engage first vertebral body V1 to the left of sagittal plane SP percutaneously and first device D10 is inserted into first vertebral body V1 such that longitudinal axis L extends at an angle γ relative to sagittal plane SP. In some embodiments, angle γ is an acute angle. In some embodiments, angle γ is an angle between about 1 and 45 degrees.

A second device D20 is positioned through a second surgical pathway using a lateral approach to engage first vertebral body V1 to the left of sagittal plane SP percutaneously. In some embodiments, a pilot hole is made in first vertebral body V1 for second device D20, and second device D20 is inserted into the pilot hole such that threads on the outer surface of a shaft 18 of second device D20 engage a portion of first vertebral body V1 that define the pilot hole and second device D20 is rotated about a longitudinal axis L1 defined by shaft 18 until second device D20 threadingly engages first vertebral body V1. In some embodiments, second device D20 is threaded into the pilot hole and/or first vertebral body V1 using an instrument, such as, for example, a driver that engages a tool engaging portion 20 of shaft 18.

In some embodiments, second device D20 is threaded into first vertebral body V1 using a surgical drill, such as, for example, a drill and/or tap included in the POWEREASE™ System sold by Medtronic. As shown in FIG. 2A, second device D20 is inserted relative to first device D10 such that shaft 12 is spaced apart from shaft 18. In some embodiments, second device D20 is inserted into first vertebral body V1 such that longitudinal axis L1 extends parallel to coronal plane CP. In some embodiments, axis L1 extends at an angle A relative to coronal plane CP. In some embodiments, angle λ is an acute angle. In some embodiments, angle λ is an angle between about 1 and 45 degrees. In some embodiments, axis L1 extends at an angle δ relative to coronal plane CP. In some embodiments, angle δ is an acute angle. In some embodiments, angle δ is an angle between about 1 and 45 degrees. In some embodiments, second device D20 is positioned through a second surgical pathway using a lateral approach to engage first vertebral body V1 to the right of sagittal plane SP percutaneously. In some embodiments, first device D10 and second device D20 are each in the same transverse plane of body B. In some embodiments, shaft 18 can be variously configured, such as, for example, smooth, ringed and/or have various cross sectional configurations, such as, for example, square, polygonal or round.

In some embodiments, second device D20 is inserted through the second surgical pathway to engage first vertebral body V1 without moving the patient from a position in which first device D10 is inserted through the first surgical pathway to engage first vertebral body V1. That is, the patient is not moved or repositioned to insert second device D20 within body B to engage first vertebral body V1 after inserting first device D10 into body B to engage first vertebral body V1. In some embodiments, the patient's position is maintained between the insertion of first device D10 through the first surgical pathway to engage first vertebral body V1 and the insertion of second device D20 through the second surgical pathway to engage first vertebral body V1, at least in part, by a device, such as, for example, a surgical table, a surgical bed, cushions, wedges, etc. In some embodiments, the device is a dynamic surgical table system, such as, for example, that disclosed in U.S. Pat. No. 7,234,180, which is incorporated herein by reference, in its entirety. In some embodiments, the patient is maintained in a position such that coronal plane CP of body B is disposed at an angle α, such as, for example an acute angle relative to a floor F of the operating room, as shown in FIG. 1L, for example.

Figure 2B:
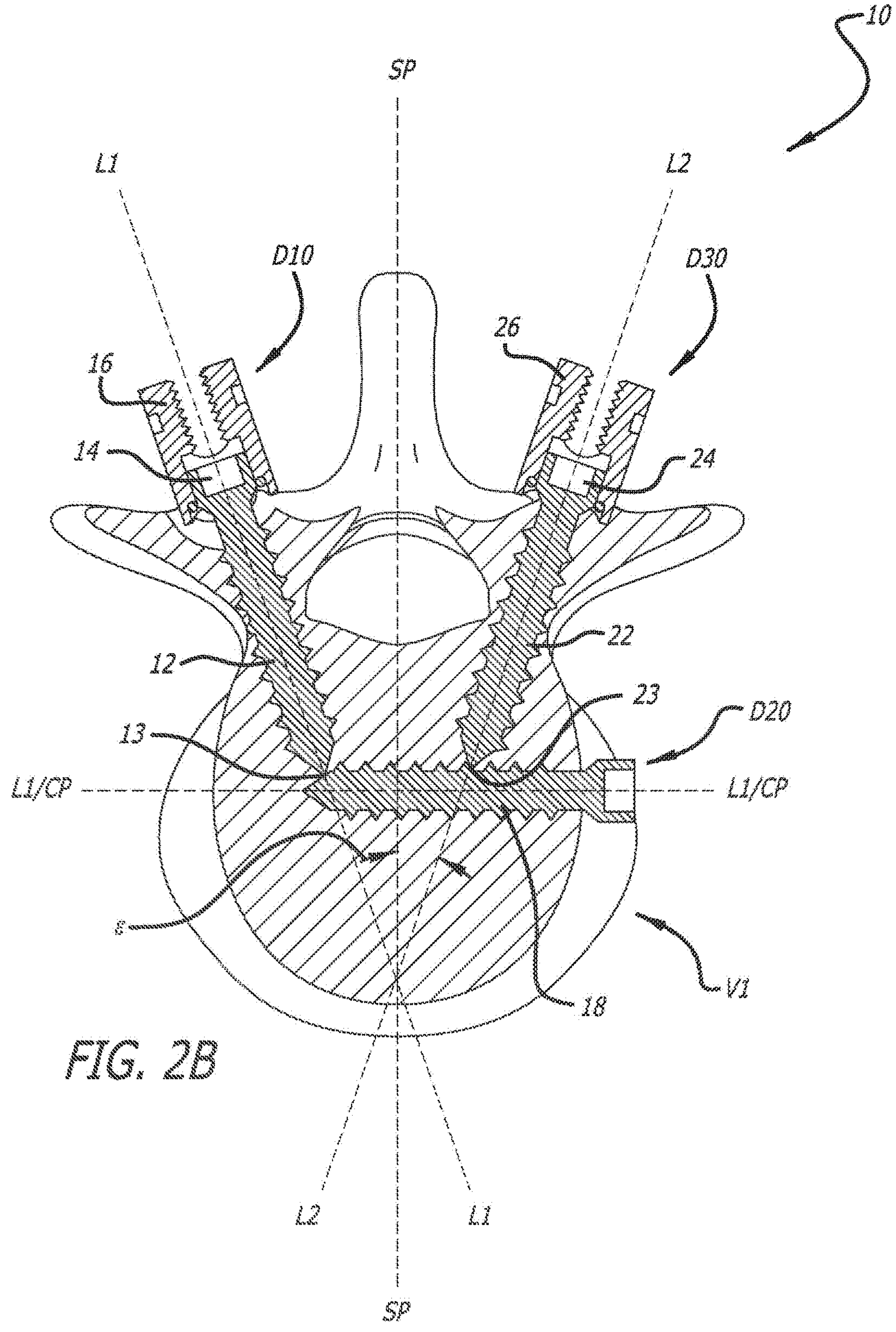
FIG. 2B is a top view, in part cross section, of the vertebral body shown in FIG. 2A including the first device shown in FIG. 2A inserted through a first incision using a posterior approach to engage the vertebral body, a second device inserted through a second incision using a lateral approach to engage the vertebral body, and a third device inserted through the first incision using a posterior approach to engage the vertebral body, where the second and third devices are each bone screws that are in the same plane and the second device engages each of the first and third devices.

In one embodiment, shown in FIG. 2B, the length of shaft 18 in FIG. 2B is greater than the length of shaft 18 in FIG. 2A such that a distal tip 13 of shaft 12 engages and/or comes into close proximity shaft 18 to increase loading on first vertebral body V1, especially any points near the shafts where there is additional load imparted on the bony structure. According to Wolff's law, for example, increasing the loading on a bone, such as, for example a vertebra, will cause the bone to remodel itself over time to resist such increased loading. That is the bone will become stronger by, for example, increasing the thickness of cortical bone. In some embodiments, the amount of loading on first vertebral body V1 is increased when shaft 18 engages shaft 12 than when shaft 18 is spaced apart from shaft 12. Thus the combinations of implants placed as shown in FIGS. 2A-21 may act to strengthen otherwise weakened, structurally-compromised and/or fractured vertebrae as well as create a rigid and/or semi-rigid support structure within the vertebrae.

As also shown in FIG. 2B, a third device D30, such as, for example a bone screw is positioned through a third surgical pathway using a posterior approach to engage first vertebral body V1 to the left of sagittal plane SP percutaneously. In some embodiments, third device D30 engages a portion of first vertebral body V1 between the articular process of vertebral body V1 and the transverse process of first vertebral body V1. In some embodiments, a pilot hole is made in first vertebral body V1 for third device D30, and third device D30 is inserted into the pilot hole such that threads on the outer surface of a shaft 22 of third device D30 engage a portion of first vertebral body V1 that define the pilot hole and third device D30 is rotated about a longitudinal axis L2 defined by shaft 22 until third device D30 threadingly engages first vertebral body V1. In some embodiments, third device D30 is threaded into the pilot hole and/or first vertebral body V1 using an instrument, such as, for example, a driver that engages a tool engaging portion 24 of shaft 22. In some embodiments, third device D30 includes receiver 26 that is rotatably coupled to shaft 22. Receiver 26 comprises a pair of arms defining an implant cavity, such as, for example a U-shaped implant cavity (such as a "tulip head" typically associated with multi-axial screws in spinal implant systems) configured for disposal of a connecting element, such as, for example, a surgical rod. In some embodiments, third device D30 is inserted into first vertebral body V1 such that longitudinal axis L2 extends at an angle ε relative to sagittal plane SP. In some embodiments, angle ε is an acute angle. In some embodiments, angle ε is an angle between about 1 and 45 degrees. In some embodiments, first device D10, second device D20 and third device D30 are each in the same transverse plane of body B. In some embodiments, shaft 22 can be variously configured, such as, for example, smooth, ringed and/or have various cross sectional configurations, such as, for example, square, polygonal or round.

In some embodiments, third device D30 is substantially similar to second device D20. In some embodiments, axis L extends at a first angle (e.g., angle β) relative to sagittal plane SP and axis L2 extends at a second angle (e.g., angle ε) relative to sagittal plane SP, where the first and second angles are inverse angles. That is, the angle axis L extends relative to sagittal plane SP is the inverse of the angle axis L2 extends relative to sagittal plane SP. For example, if axis L extends at an angle β of 30° relative to sagittal plane SP, axis L2 extends an angle ε of −30° relative to sagittal plane SP, and vice versa.

As shown in FIG. 2B, third device D30 is positioned relative to second device D20 such that a distal tip 23 of shaft 22 engages shaft 18 to increase the loading on first vertebral body V1. That is, the amount of loading on first vertebral body V1 is increased when shaft 22 engages shaft 18 and shaft 18 engages shaft 12 than when shaft 18 engages shaft 12 without shaft 22 engaging shaft 18. According to Wolff's law, the increased loading caused by having shafts 12, 22 each engage shaft 18 causes first vertebral body V1 to become stronger by, for example, increasing the thickness of cortical bone.

In some embodiments, third device D30 is inserted through the third surgical pathway to engage first vertebral body V1 without moving the patient from a position in which first device D10 is inserted through the first surgical pathway to engage first vertebral body V1 and second device D20 is inserted through the second surgical pathway to engage first vertebral body V1. That is, the patient is not moved or repositioned to insert third device D30 within body B to engage first vertebral body V1 after inserting first device D10 and second device D20 into body B to engage first vertebral body V1. In some embodiments, the patient's position is maintained between the insertion of first device D10 through the first surgical pathway to engage first vertebral body V1, the insertion of second device D20 through the second surgical pathway to engage first vertebral body V1, and the insertion of third device 30 through the third surgical pathway to engage first vertebral body V1, at least in part, by a device, such as, for example, a surgical table, a surgical bed, cushions, wedges, etc. In some embodiments, the device is a dynamic surgical table system, such as, for example, that disclosed in U.S. Pat. No. 7,234,180, which is incorporated herein by reference, in its entirety. In some embodiments, the patient is maintained in a position such that coronal plane CP of body B is disposed at an angle α, such as, for example an acute angle relative to a floor F of the operating room, as shown in FIG. 1L, for example.

Figure 2C:
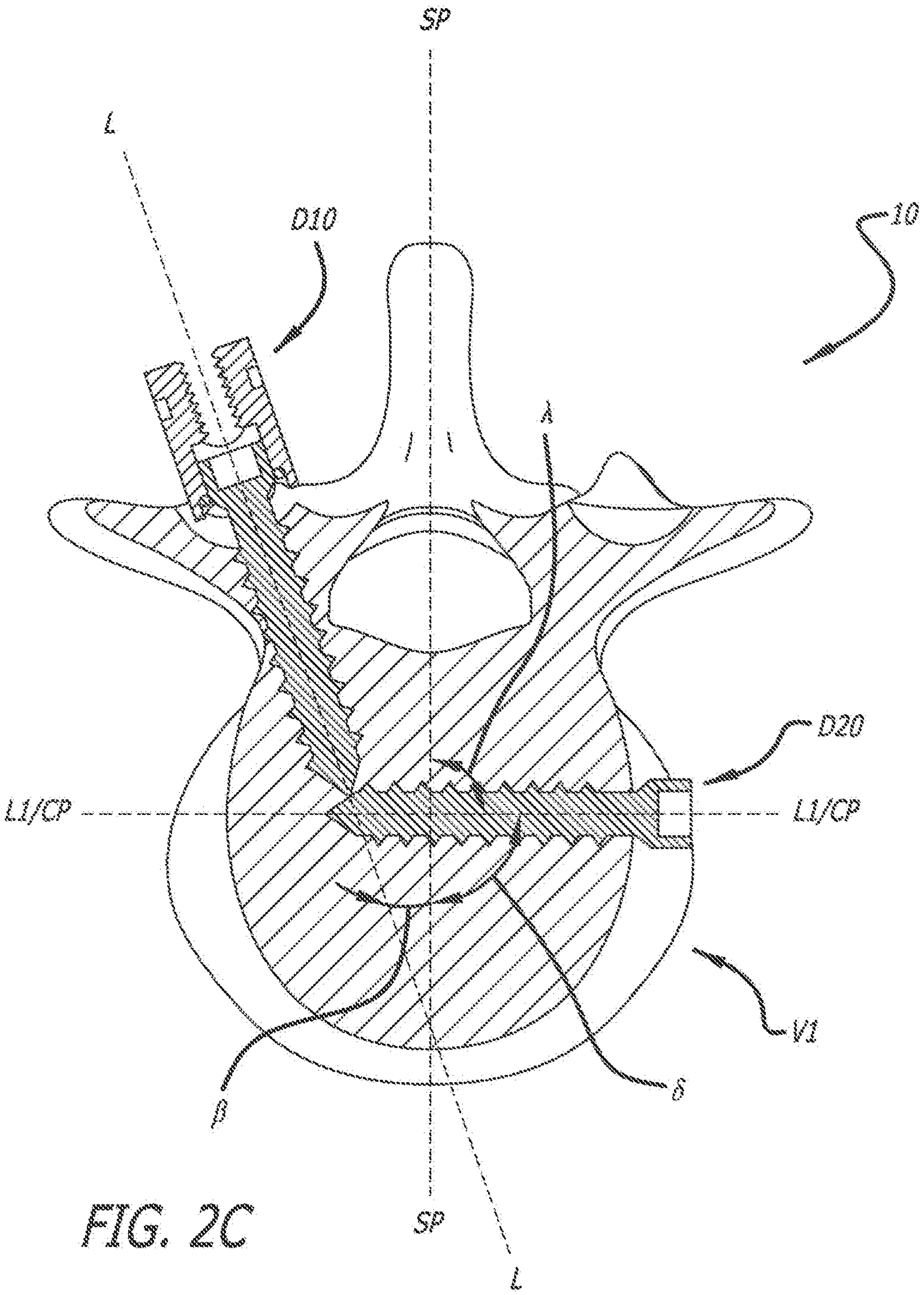
FIG. 2C is a top view, in part cross section, of the vertebral body shown in FIG. 2A including the first device shown in FIG. 2A inserted through a first incision using a posterior approach to engage the vertebral body, and the second device shown in FIG. 2B inserted through a second incision using a lateral approach to engage the vertebral body and the first device, where the first and second devices are in the same plane and the third device shown in FIG. 2B has been removed from the vertebral body.

As shown in FIG. 2C, first device D10 is positioned through a first surgical pathway using a posterior approach to engage first vertebral body V1 to the right of sagittal plane SP percutaneously. First device D10 engages a portion of first vertebral body V1 between the articular process of vertebral body V1 and the transverse process of first vertebral body V1. First device D10 is inserted into first vertebral body V1 such that longitudinal axis L extends at an angle β relative to sagittal plane SP. In some embodiments, angle β is an acute angle. In some embodiments, angle β is an angle between about 1 and 45 degrees.

Second device D20 is positioned through a second surgical pathway using a lateral approach to engage first vertebral body V1 to the left of sagittal plane SP percutaneously. Second device D20 is inserted into first vertebral body V1 such that longitudinal axis L1 extends parallel to coronal plane CP. In some embodiments, axis L1 extends at an angle λ relative to coronal plane CP. In some embodiments, angle λ is an acute angle. In some embodiments, angle λ is an angle between about 1 and 45 degrees. In some embodiments, axis L1 extends at an angle δ relative to coronal plane CP. In some embodiments, angle δ is an acute angle. In some embodiments, angle δ is an angle between about 1 and 45 degrees. In some embodiments, second device D20 is positioned through a second surgical pathway using a lateral approach to engage first vertebral body V1 to the right of sagittal plane SP percutaneously. In some embodiments, first device D10 and second device D20 are each in the same transverse plane of body B. As shown in FIG. 2C, shaft 18 engages shaft 12 to increase loading on first vertebral body V1.

In some embodiments, second device D20 is inserted through the second surgical pathway to engage first vertebral body V1 without moving the patient from a position in which first device D10 is inserted through the first surgical pathway to engage first vertebral body V1. That is, the patient is not moved or repositioned to insert second device D20 within body B to engage first vertebral body V1 after inserting first device D10 into body B to engage first vertebral body V1. In some embodiments, the patient's position is maintained between the insertion of first device D10 through the first surgical pathway to engage first vertebral body V1 and the insertion of second device D20 through the second surgical pathway to engage first vertebral body V1, at least in part, by a device, such as, for example, a surgical table, a surgical bed, cushions, wedges, etc. In some embodiments, the device is a dynamic surgical table system, such as, for example, that disclosed in U.S. Pat. No. 7,234,180, which is incorporated herein by reference, in its entirety. In some embodiments, the patient is maintained in a position such that coronal plane CP of body B is disposed at an angle α, such as, for example an acute angle relative to a floor F of the operating room, as shown in FIG. 1L, for example.

Figure 2D:
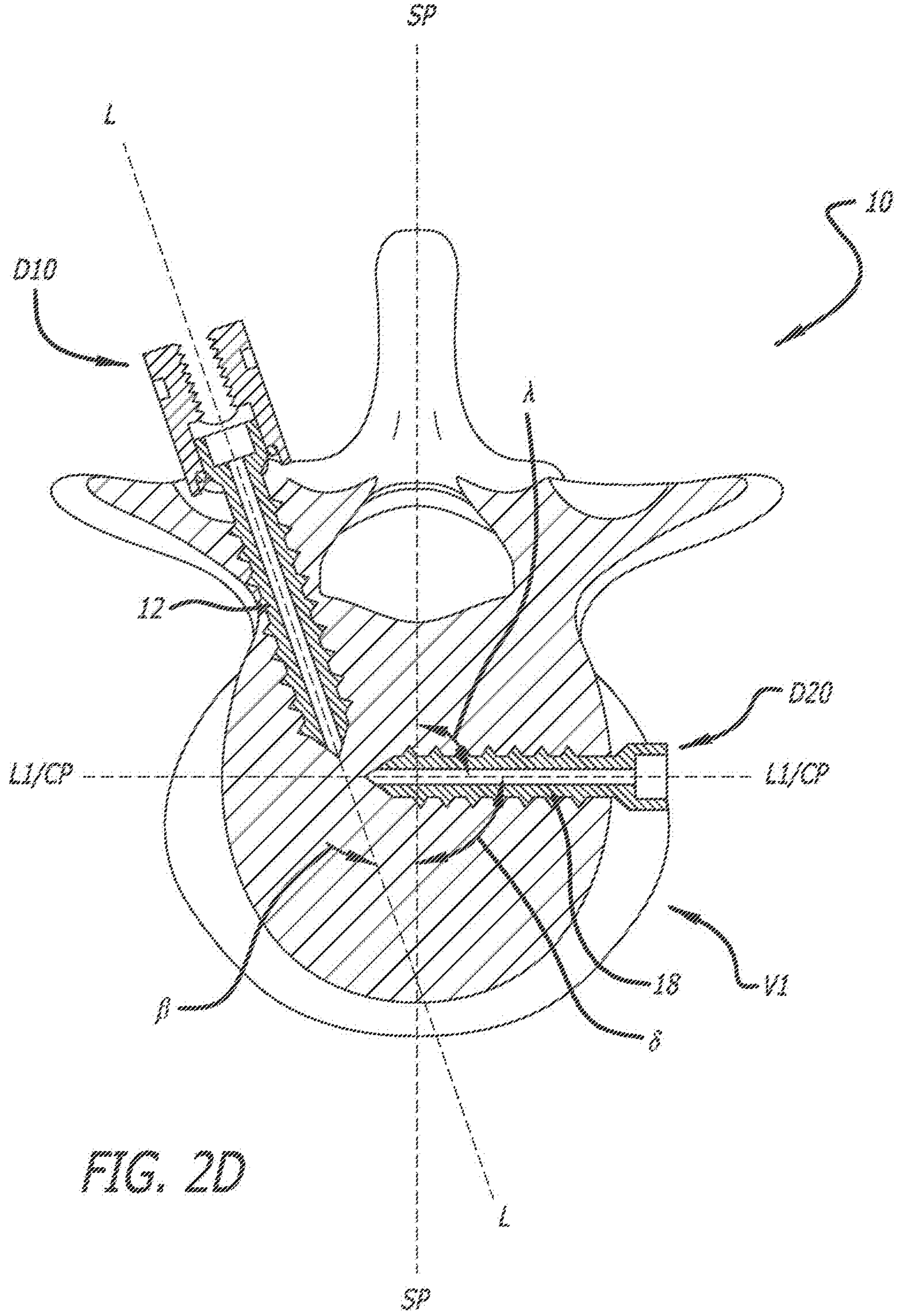
FIG. 2D is a top view, in part cross section, of the vertebral body shown in FIG. 2A including a first device inserted through a first incision using a posterior approach to engage the vertebral body, and a second device inserted through a second incision using a lateral approach to engage the vertebral body, where the first and second devices are cannulated bone screws and the first device is spaced apart from the second device.

In one embodiment, shown in FIG. 2D, first device D10 is a cannulated bone screw that is positioned through a first surgical pathway using a posterior approach to engage a first vertebral body V1 to the right of sagittal plane SP percutaneously, as described above with reference to FIG. 2A and/or FIG. 2B. Second device D20 is a cannulated bone screw that is positioned through a second surgical pathway using a lateral approach to engage first vertebral body V1 to the left of sagittal plane SP percutaneously, as described above with reference to FIG. 2A and/or FIG. 2B. As shown in FIG. 2D, second device D20 is inserted relative to first device D10 such that shaft 12 is spaced apart from shaft 18. In some embodiments, second device D20 is inserted into first vertebral body V1 such that longitudinal axis L1 extends parallel to coronal plane CP. In some embodiments, axis L1 extends at an angle A relative to coronal plane CP. In some embodiments, angle λ is an acute angle. In some embodiments, angle λ is an angle between about 1 and 45 degrees. In some embodiments, axis L1 extends at an angle δ relative to coronal plane CP. In some embodiments, angle δ is an acute angle. In some embodiments, angle δ is an angle between about 1 and 45 degrees. In some embodiments, second device D20 is positioned through a second surgical pathway using a lateral approach to engage first vertebral body V1 to the right of sagittal plane SP percutaneously. In some embodiments, first device D10 and second device D20 are each in the same transverse plane of body B.

In some embodiments, second device D20 is inserted through the second surgical pathway to engage first vertebral body V1 without moving the patient from a position in which first device D10 is inserted through the first surgical pathway to engage first vertebral body V1. That is, the patient is not moved or repositioned to insert second device D20 within body B to engage first vertebral body V1 after inserting first device D10 into body B to engage first vertebral body V1. In some embodiments, the patient's position is maintained between the insertion of first device D10 through the first surgical pathway to engage first vertebral body V1 and the insertion of second device D20 through the second surgical pathway to engage first vertebral body V1, at least in part, by a device, such as, for example, a surgical table, a surgical bed, cushions, wedges, etc. In some embodiments, the device is a dynamic surgical table system, such as, for example, that disclosed in U.S. Pat. No. 7,234,180, which is incorporated herein by reference, in its entirety. In some embodiments, the patient is maintained in a position such that coronal plane CP of body B is disposed at an angle α, such as, for example an acute angle relative to a floor F of the operating room, as shown in FIG. 1L, for example.

In some embodiments, a guide wire is inserted to guide at least one of first and second devices D10, D20. That is, at least one guide wire is inserted into first vertebral body V1. One of the guidewires is inserted into the cannula of one of first and second devices D10, D20. First and second devices D10, D20 are then slid along the guidewires to engage first and second devices D10, D20 with first vertebral body V1 in the manner described above.

In some embodiments, a material is introduced through the cannulae of at least one of first and second devices D10, D20 to deliver the material to first vertebral body V1. In some embodiments, the material is bone cement, a bone growth material, such as, for example, bone morphogenetic protein (BMP), an analgesic and/or an anti-inflammatory agent. In some embodiments, an instrument is introduced through the cannulae of at least one of first and second devices D10, D20 to provide navigational capabilities and/or stimulate bone growth. In some embodiments, the instrument is a probe and/or electrodes.

Figure 2E:
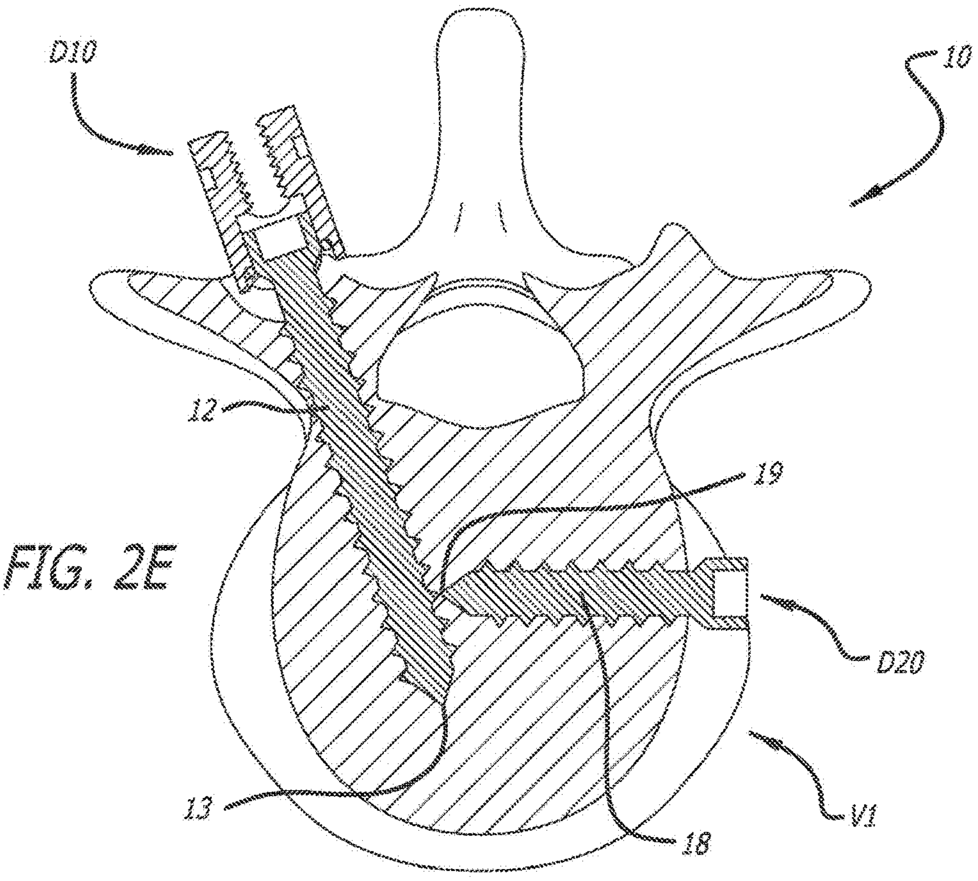
FIG. 2E is a top view, in part cross section, of the vertebral body shown in FIG. 2A including a first device inserted through a first incision using a posterior approach to engage the vertebral body, and a second device inserted through a second incision using a lateral approach to engage the vertebral body and the first device, where the first device has a length that is greater than that of the second device.

In one embodiment, shown in FIG. 2E, the length of shaft 12 in FIG. 2E is greater than the length of shaft 12 in FIG. 2A such that a distal tip 19 of shaft 18 engages shaft 12 to increase loading on first vertebral body V1 and tip 13 is spaced apart from shaft 18. In one embodiment, first device D10 is a pedicle screw and second device D20 is a lateral screw having a maximum length that is less than that of first device D10.

Figure 2F:
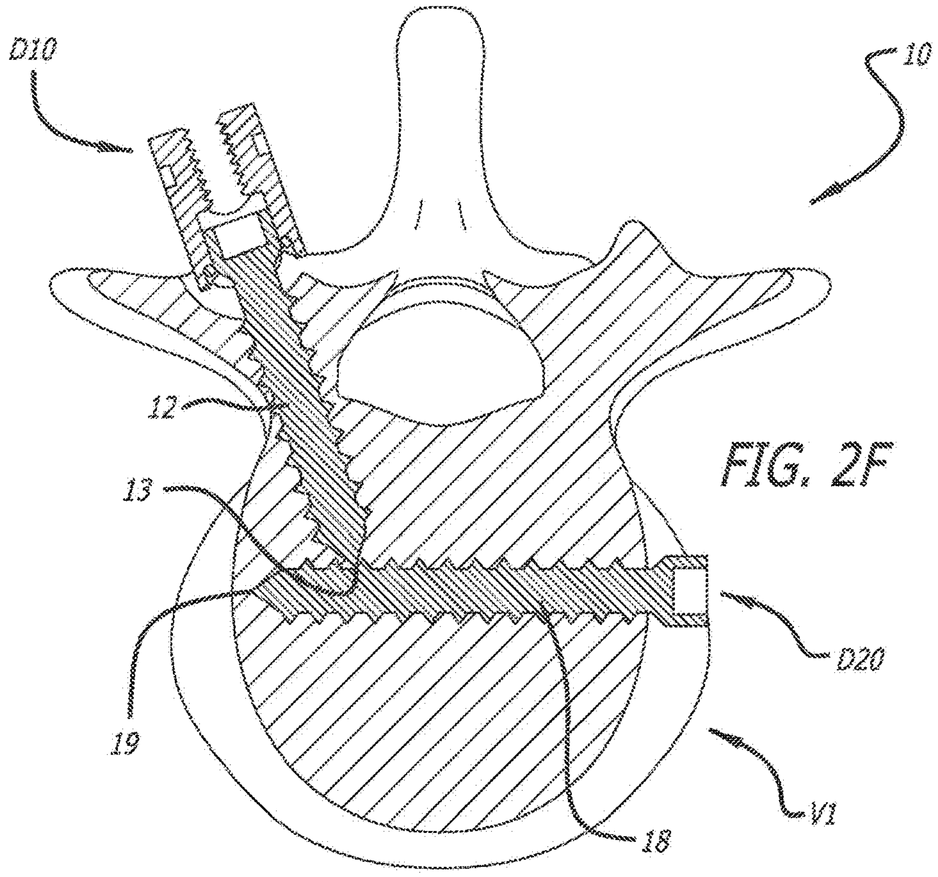
FIG. 2F is a top view, in part cross section, of the vertebral body shown in FIG. 2A including a first device inserted through a first incision using a posterior approach to engage the vertebral body, and a second device inserted through a second incision using a lateral approach to engage the vertebral body and the first device, where the second device has a length that is greater than that of the first device.
Figure 2I:
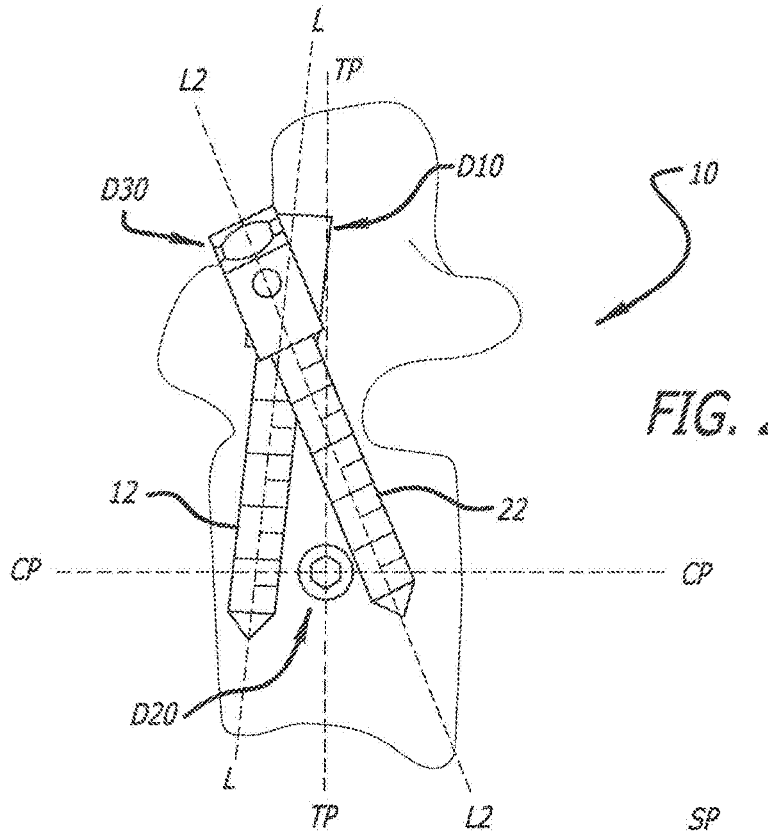
FIG. 2I is a side view in part phantom, of a vertebral body including the first device shown in FIG. 2G inserted through a first incision using a posterior approach to engage the vertebral body, the second device shown in FIG. 2G inserted through the first incision using a posterior approach to engage the vertebral body, and the third device shown in FIG. 2G inserted through a second incision using a lateral approach to engage the vertebral body, where at least one of the first and second devices are in a first plane and the third device is in a second plane that is different than the first plane.

In one embodiment, shown in FIG. 2F, the length of shaft 18 in FIG. 2F is greater than the length of shaft 18 in FIG. 2A such that tip 13 of shaft 12 engages shaft 18 to increase loading on first vertebral body V1 and tip 19 is spaced apart from shaft 12. In one embodiment, first device D10 is a pedicle screw and second device D20 is a lateral screw having a maximum length that is greater than that of first device D10.

In one embodiment, shown in FIGS. 2G-21, first device D10 is positioned through the first surgical pathway using a posterior approach to engage first vertebral body V1 to the right of sagittal plane SP percutaneously. First device D10 engages a portion of first vertebral body V1 between the articular process of vertebral body V1 and the transverse process of first vertebral body V1 such that longitudinal axis L extends at an acute angle relative to coronal plane CP and shaft 12 extends in a cranial direction through first vertebral body V1. Second device D20 is positioned through the second surgical pathway using a lateral approach to engage first vertebral body V1 to the left of sagittal plane SP percutaneously. Second device D20 is inserted into first vertebral body V1 such that longitudinal axis L1 extends parallel to coronal plane CP and/or a transverse plane TP of body B. Shaft 12 and/or tip 13 are positioned more toward a cranial end of body B than is shaft 18 such that shaft 12 is spaced apart from shaft 18. Third device D30 is positioned through the third surgical pathway using a posterior approach to engage first vertebral body V1 to the left of sagittal plane SP percutaneously. Third device D30 engages a portion of first vertebral body V1 between the articular process of vertebral body V1 and the transverse process of first vertebral body V1 such that longitudinal axis L2 extends at an acute angle relative to coronal plane CP and shaft 22 extends in a caudal direction through first vertebral body V1. Shaft 22 and/or tip 23 are positioned more toward a caudal end of body B than is shaft 12 such that shaft 22 is spaced apart from shafts 12, 18.

Figure 2J:
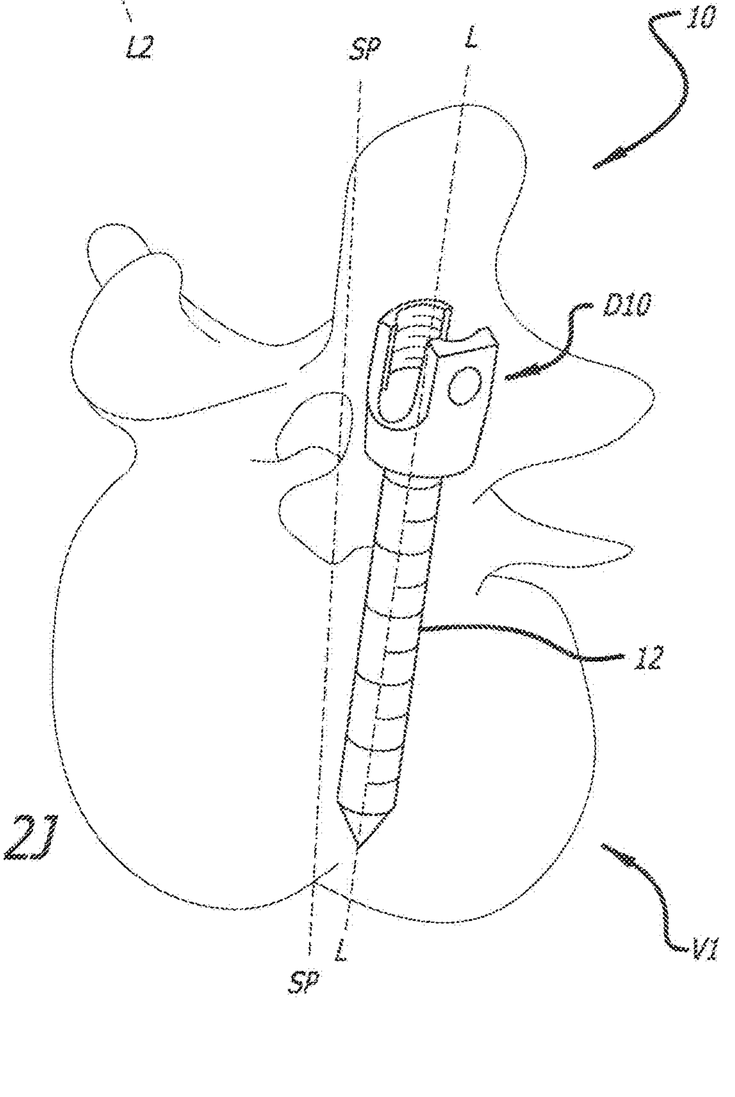
FIG. 2J is a top, perspective view, in part phantom, of a vertebral body that is accessed in the patient's middle lower back and includes a first device that is inserted through a first incision using a Minimally Invasive Lateral Interbody Fusion procedure with a posterior approach to engage the vertebral body.
Figure 2K:
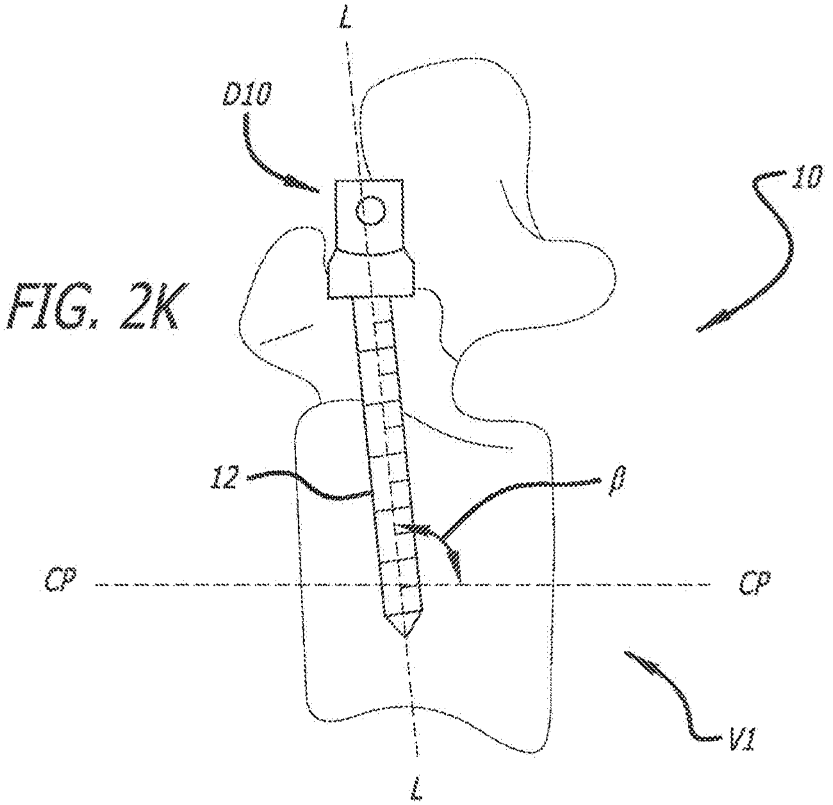
FIG. 2K is a side view in part phantom, of the vertebral body shown in FIG. 2J that is accessed in the patient's middle lower back and includes the first device shown in FIG. 2J inserted through the first incision using a Minimally Invasive Lateral Interbody Fusion procedure with a posterior approach to engage the vertebral body.

In one embodiment, shown in FIGS. 2J and 2K, first device D10 is used in performing a midline interbody fusion (MIDLIF) and is positioned through the first surgical pathway using a posterior approach to engage first vertebral body V1 to the left of sagittal plane SP percutaneously and/or via a "mini-open" hybrid technique using a smaller near-midline incision as described in Medtronic's MAST MIDLF® technique. First device D10 engages a portion of first vertebral body V1 between the articular process of vertebral body V1 and the transverse process of first vertebral body V1 such that longitudinal axis L extends at an angle β (FIG. 2K) relative to coronal plane CP. In some embodiments, angle β (FIG. 2K) is an obtuse angle. In some embodiments, angle β (FIG. 2K) is an angle between about 91 and 120 degrees.

Figure 2L:
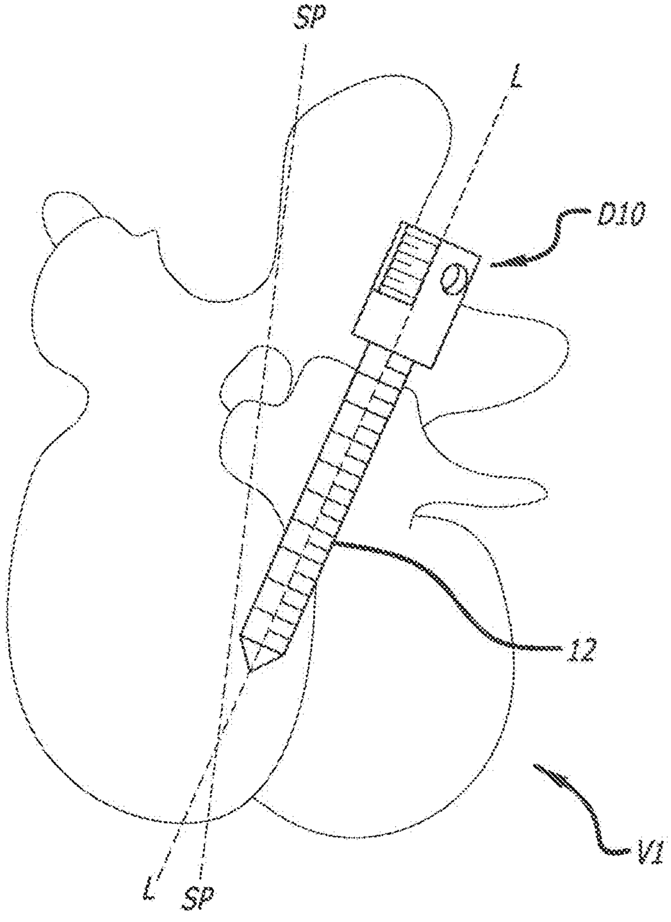
FIG. 2L is a top, perspective view, in part phantom, of a vertebral body that is accessed in the patient's middle lower back and includes a first device that is inserted through a first incision using a Minimally Invasive Lateral Interbody Fusion procedure with a posterior approach to engage the vertebral body.
Figure 2M:
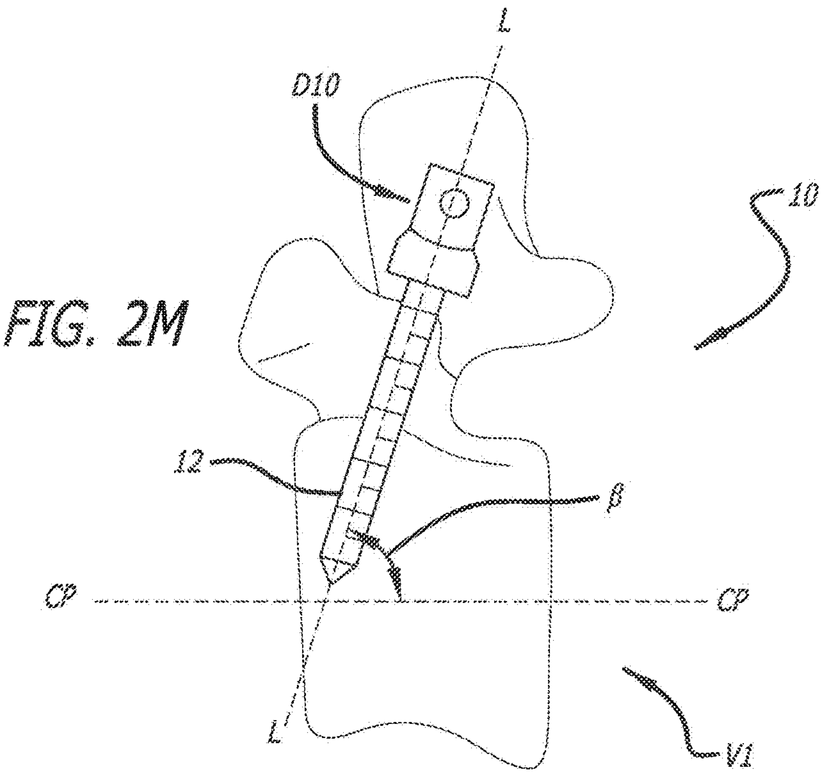
FIG. 2M is a side view in part phantom, of the vertebral body shown in FIG. 2L that is accessed in the patient's middle lower back and includes the first device shown in FIG. 2L inserted through the first incision using a Minimally Invasive Lateral Interbody Fusion procedure with a posterior approach to engage the vertebral body.

In one embodiment, shown in FIGS. 2L and 2M, first device D10 is used in performing midline interbody fusion (MIDLIF) and is positioned through the first surgical pathway using a posterior approach to engage first vertebral body V1 to the left of sagittal plane SP percutaneously. First device D10 engages a portion of first vertebral body V1 between the articular process of vertebral body V1 and the transverse process of first vertebral body V1 such that longitudinal axis L extends at an angle β (FIG. 2M) relative to coronal plane CP. In some embodiments, angle β (FIG. 2M) is an acute angle. In some embodiments, angle β (FIG. 2M) is an angle between about 1 and 75 degrees.

In any of the embodiments shown in FIGS. 2A-2M, at least one of first, second and third devices D10, D20, D30 may be inserted into body B using an instrument, such as, for example, an instrument having integrated neuromonitoring and/or navigation capabilities. In some embodiments, the instrument having integrated neuromonitoring and/or navigation capabilities is used to establish and/or monitor the trajectories of at least one of first, second and third devices D10, D20, D30. That is, the instrument having integrated neuromonitoring and/or navigation capabilities may be used to determine and/or select a safe trajectory in relation to the patient's anatomy for at least one first, second and third devices D10, D20, D30, even as that anatomy shifts in real-time and/or ensure that at least one of first, second and third devices D10, D20, D30 is being inserted and/or implanted using the selected trajectory. In some embodiments, the instrument having integrated neuromonitoring and/or navigation capabilities is part of a navigation system sold by Medtronic, such as, for example, StealthStation® S7®, StealthStation i7™, StealthStation iNav®, AxiEM Electromagnetic Navigation System, Fusion™ ENT and/or StealthViz™ Planning Station. In some embodiments, the instrument having integrated neuromonitoring and/or navigation capabilities aids a medical practitioner to perform safer, more precise procedure, reduce procedure invasiveness and risk and/or improve patient outcomes and recovery.

In any of the embodiments shown in FIGS. 2A-2M, imaging may be used to establish and/or monitor the trajectories of at least one of first, second and third devices D10, D20, D30 through incisions using the approaches discussed above. In one embodiment, an imaging system, such as, for example, the O-arm Surgical Imaging System available from Medtronic is used to establish and/or monitor the trajectories of at least one of first, second and third devices D10, D20, D30 using intra-operative imaging. The O-arm Surgical Imaging System, among other things, provides fast access to real-time, multi-plane 3D images (and 2D images), provides full support of the unique workflow of procedures, such as, for example, spinal procedures, minimizes radiation dose for surgical staff (by reducing X-ray exposure, for example) and provides visualization to confirm hardware therapy placement, potentially eliminating revision surgeries.

In any of the embodiments shown in FIGS. 2A-2M, at least one of first, second and third devices D10, D20, D30 may be cannulated. In some embodiments, a guide wire is inserted to guide at least one of first, second and third devices D10, D20, D30 into position relative to vertebrae V in the manner discussed above. That is, at least one guide wire is inserted into first vertebral body V1 and/or second vertebral body V2. One of the guidewires is inserted into the cannula of one of first, second and third devices D10, D20, D30. First, second and third devices D10, D20, D30 are then slid along the guidewires to engage first, second and third devices D10, D20, D30 with vertebrae V in the manner described above.

In any of the embodiments shown in FIGS. 2A-2M, at least one of first, second and third devices D10, D20, D30 is a cannulated screw without fenestrations and/or a cannulated screw having at least one lateral fenestration that is in communication with the cannula. In some embodiments, a material is introduced through the cannulae and/or fenestrations of at least one of first, second and third devices D10, D20, D30 to deliver the material to first vertebral body V1 and/or second vertebral body V2. In some embodiments, the material is bone cement, a bone growth material, such as, for example, bone morphogenetic protein (BMP), an analgesic and/or an anti-inflammatory agent. In some embodiments, an instrument is introduced through the cannulae and/or fenestrations of at least one of first, second and third devices D10, D20, D30 to provide navigational capabilities and/or stimulate bone growth. In some embodiments, the instrument is a probe and/or electrodes.

Figure 3A:
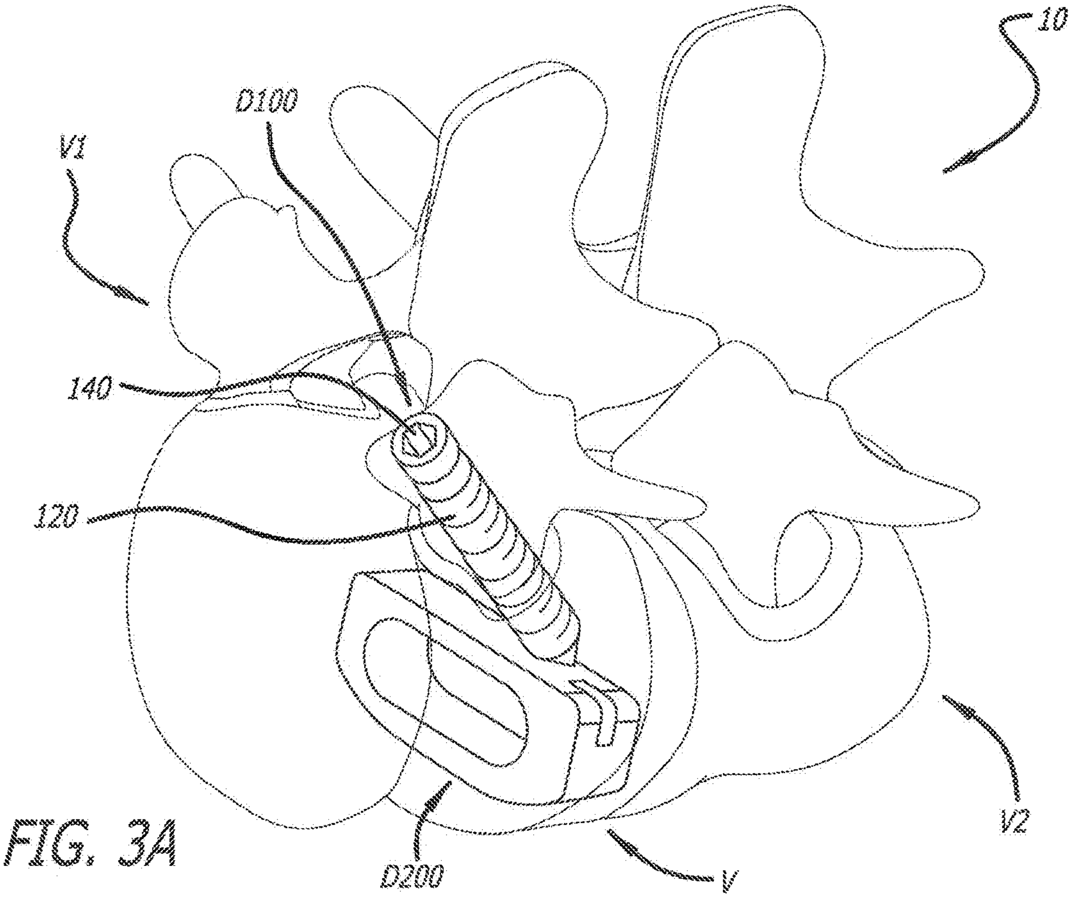
FIG. 3A is a top, perspective view, in part phantom, of first and second vertebral bodies, with a first device extending through a first incision using a posterior approach such that the first device extends through the first vertebral body and into a space between the first and second vertebral bodies, and a second device extending through a second incision using a lateral approach to position the second device in the space between the first and second vertebral bodies such that the first device engages the second device and a tip of the first device is posterior to the second device.
Figure 3B:
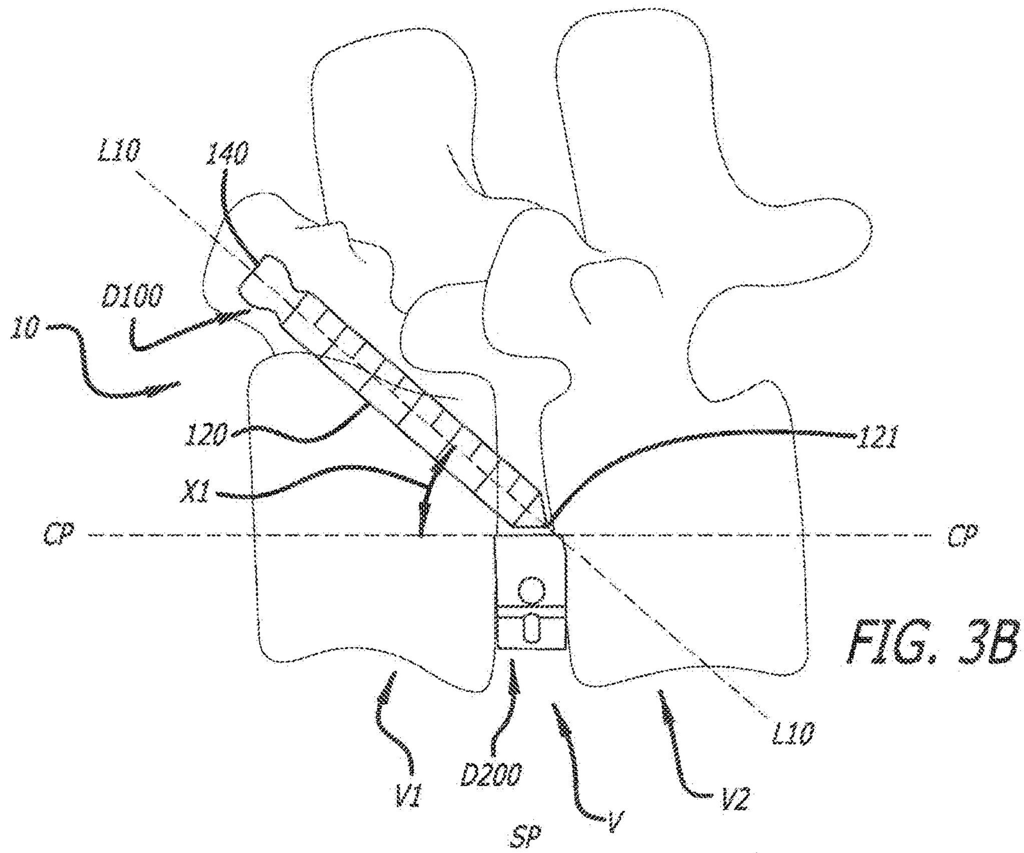
FIG. 3B is a side view, in part phantom, of the first and second vertebral bodies shown in FIG. 3A, with the first device shown in FIG. 3A extending through a first incision using a posterior approach such that the first device extends through the first vertebral body and into the space between the first and second vertebral bodies, and the second device shown in FIG. 3A extending through a second incision using a lateral approach to position the second device in the space between the first and second vertebral bodies such that the first device engages the second device and a tip of the first device is posterior to the second device.
Figure 3C:
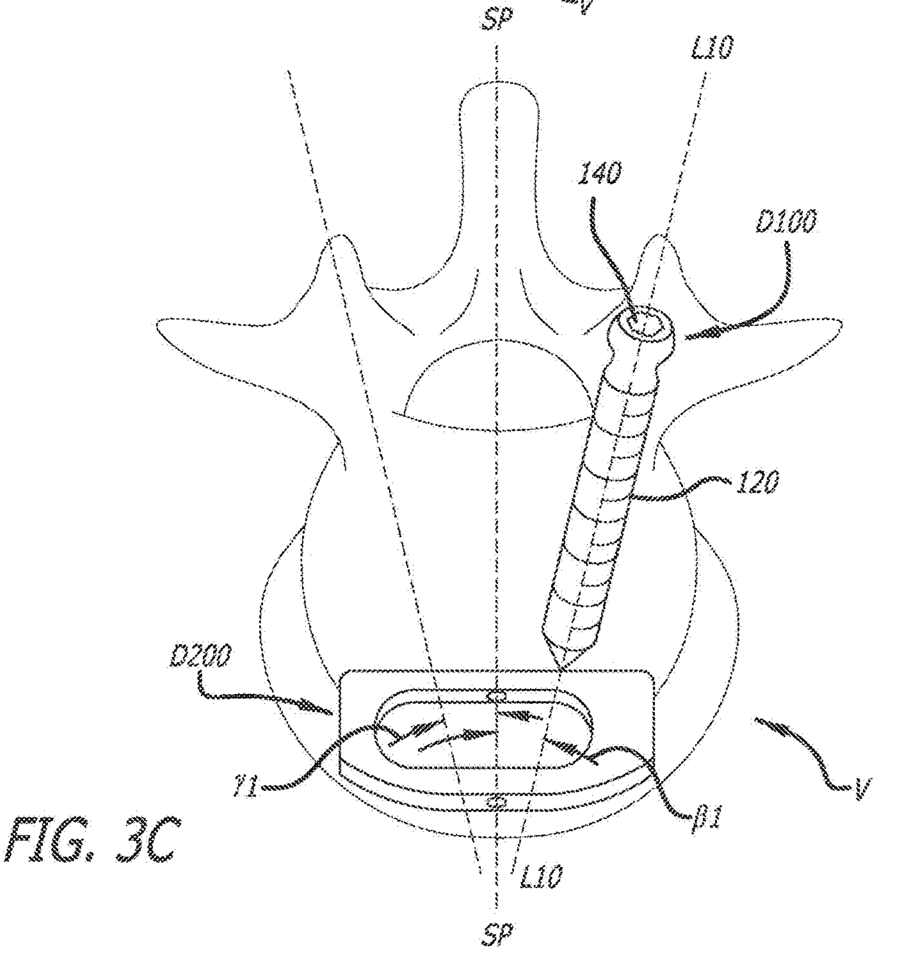
FIG. 3C is a top view, in part phantom, of the first and second vertebral bodies shown in FIG. 3A, with the first device shown in FIG. 3A extending through a first incision using a posterior approach such that the first device extends through the first vertebral body and into the space between the first and second vertebral bodies, and the second device shown in FIG. 3A extending through a second incision using a lateral approach to position the second device in the space between the first and second vertebral bodies such that the first device engages the second device and a tip of the first device is posterior to the second device.
Figure 3H:
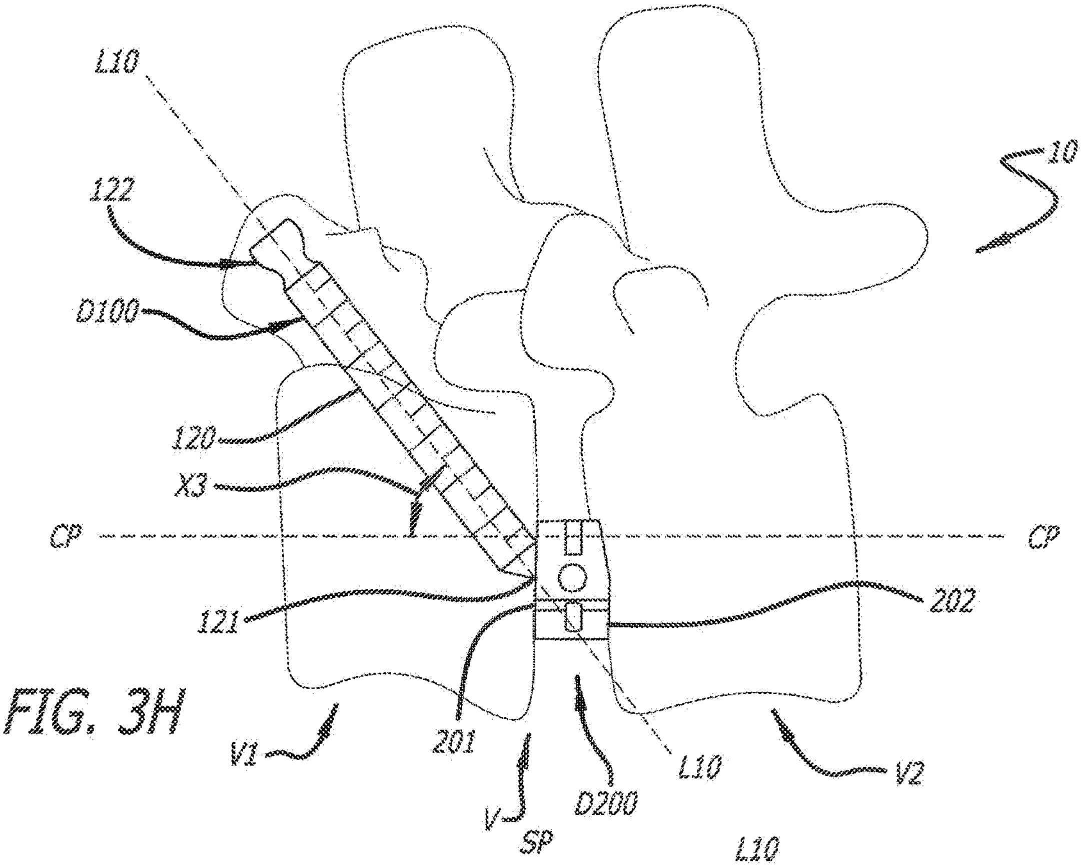
FIG. 3H is a side view, in part phantom, of the first and second vertebral bodies shown in FIG. 3G, with the first device shown in FIG. 3G extending through a first incision using a posterior approach such that the first device extends through the first vertebral body and into a space between the first and second vertebral bodies, and the second device shown in FIG. 3G extending through a second incision using a lateral approach to position the second device in the space between the first and second vertebral bodies such that the tip of the first device is positioned within the second device and the head of the first device is posterior to the facet of the first vertebral body, where the first device is a cannulated bone screw and the second device is an interbody implant.
Figure 3I:
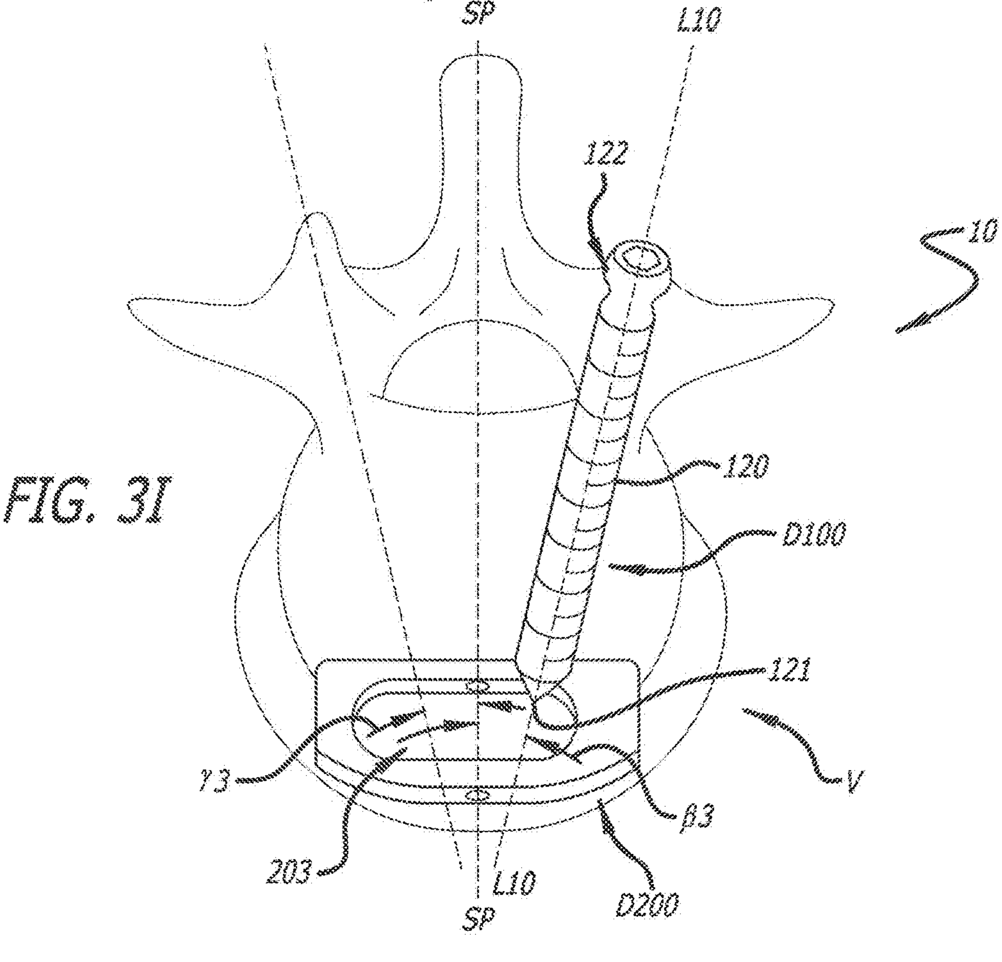
FIG. 3I is a top view, in part phantom, of the first and second vertebral bodies shown in FIG. 3G, with the first device shown in FIG. 3G extending through a first incision using a posterior approach such that the first device extends through the first vertebral body and into a space between the first and second vertebral bodies, and the second device shown in FIG. 3G extending through a second incision using a lateral approach to position the second device in the space between the first and second vertebral bodies such that the tip of the first device is positioned within the second device and the head of the first device is posterior to the facet of the first vertebral body, where the first device is a cannulated bone screw and the second device is an interbody implant.

In one embodiment, shown in FIGS. 3A-3C, a first device D100, such as, for example, a bone screw, is positioned through a first surgical pathway using a posterior approach to engage a first vertebral body V1 of vertebrae V to the left of sagittal plane SP percutaneously. In some embodiments, first device D100 engages a portion of first vertebral body V1 between the articular process of vertebral body V1 and the transverse process of first vertebral body V1. In some embodiments, a pilot hole is made in first vertebral body V1 for first device D100 and first device D100 is inserted into the pilot hole such that threads on the outer surface of a shaft 120 of first device D100 engage a portion of first vertebral body V1 that define the pilot hole and first device D100 is rotated about a longitudinal axis L10 defined by shaft 120 until first device D100 threadingly engages first vertebral body V1. In some embodiments, first device D100 is threaded into the pilot hole and/or first vertebral body V1 using an instrument, such as, for example, a driver that engages a tool engaging portion 140 of shaft 120. In some embodiments, first device D100 is threaded into first vertebral body V1 using a surgical drill, such as, for example, a drill and/or tap included in the POWEREASE™ System sold by Medtronic. In some embodiments, first device D100 is inserted into first vertebral body V1 such that longitudinal axis L10 extends at an angle β1 relative to sagittal plane SP. In some embodiments, angle β1 is an acute angle. In some embodiments, angle β1 is an angle between about 1 and 45 degrees. In some embodiments, first device D100 is inserted into first vertebral body V1 such that longitudinal axis L10 extends at an angle β1 relative to coronal plane CP. In some embodiments, angle β1 is an acute angle. In some embodiments, angle β1 is an angle between about 1 and 45 degrees. In some embodiments, first device D100 is inserted into first vertebral body V1 such that a tip 121 of shaft 120 is positioned in a space between first vertebral body V1 and second vertebral body V2. In some embodiments, shaft 120 can be variously configured, such as, for example, smooth, ringed and/or have various cross sectional configurations, such as, for example, square, polygonal or round.

In some embodiments, first device D100 is positioned through the first surgical pathway using a posterior approach to engage first vertebral body V1 to the right of sagittal plane SP percutaneously and first device D100 is inserted into first vertebral body V1 such that longitudinal axis L10 extends at an angle γ1 relative to sagittal plane SP. In some embodiments, angle γ1 is an acute angle. In some embodiments, angle γ1 is an angle between about 1 and 45 degrees.

A second device D200, such as, for example, an interbody implant, is positioned through a second surgical pathway using a lateral approach and is positioned in the space between first vertebral body V1 and second vertebral body V2 of vertebrae V percutaneously such that tip 121 is posterior to second device D200. Second device D200 is positioned in the space between first vertebral body V1 and second vertebral body V2 such that second device D200 is spaced apart from first device D100. In some embodiments, second device D200 is inserted in the space between first vertebral body V1 and second vertebral body V2 before first device D100 is inserted into first vertebral body V1. In some embodiments, first vertebral body V1 and second vertebral body V2 are distracted relative to one another to increase the space between first vertebral body V1 and second vertebral body V2 for insertion of second device D200. In some embodiments, second device D200 is an interbody implant, a trial implant, a SCISSOR JACK® implant, an inflatable implant or one or more Fernstrom balls.

In some embodiments, second device D200 is inserted through the second surgical pathway for positioning in the space between first vertebral body V1 and second vertebral body V2 without moving the patient from a position in which first device D100 is inserted through the first surgical pathway to engage first vertebral body V1. That is, the patient is not moved or repositioned to insert second device D200 within body B for positioning in the space between first vertebral body V1 and second vertebral body V2 after inserting first device D100 into body B to engage first vertebral body V1. Likewise, in embodiments, where second device D200 is inserted before first device D100, the patient is not moved or repositioned to insert first device D100 into body B to engage first vertebral body V1 after inserting second device D200 within body B for positioning in the space between first vertebral body V1 and second vertebral body V2.

In some embodiments, the patient's position is maintained between the insertion of first device D100 through the first surgical pathway to engage first vertebral body V1 and the insertion of second device D200 through the second surgical pathway for positioning in the space between first vertebral body V1 and second vertebral body V2, at least in part, by a device, such as, for example, a surgical table, a surgical bed, cushions, wedges, etc. In some embodiments, the device is a dynamic surgical table system, such as, for example, that disclosed in U.S. Pat. No. 7,234,180, which is incorporated herein by reference, in its entirety. In some embodiments, the patient is maintained in a position such that coronal plane CP of body B is disposed at an angle α, such as, for example an acute angle relative to a floor F of the operating room, as shown in FIG. 1L, for example.

In one embodiment, shown in FIGS. 3D-3F, first device D100 is positioned through a first surgical pathway using a posterior approach to engage a first vertebral body V1 of vertebrae V to the left of sagittal plane SP percutaneously. In some embodiments, first device D100 engages a portion of first vertebral body V1 between the articular process of vertebral body V1 and the transverse process of first vertebral body V1 such that a head 122 of first device D100 is posterior to a facet of first vertebral body V1. In some embodiments, first device D100 is inserted into first vertebral body V1 such that longitudinal axis L10 extends at an angle β2 relative to sagittal plane SP. In some embodiments, angle β2 is an acute angle. In some embodiments, angle β2 is an angle between about 1 and 45 degrees. In some embodiments, first device D100 is inserted into first vertebral body V1 such that longitudinal axis L10 extends at an angle X2 relative to coronal plane CP.

In some embodiments, angle X2 is an acute angle. In some embodiments, angle X2 is an angle between about 1 and 45 degrees. In some embodiments, first device D100 is positioned through the first surgical pathway using a posterior approach to engage first vertebral body V1 to the right of sagittal plane SP percutaneously and first device D100 is inserted into first vertebral body V1 such that longitudinal axis L10 extends at an angle γ2 relative to sagittal plane SP. In some embodiments, angle γ2 is an acute angle. In some embodiments, angle γ2 is an angle between about 1 and 45 degrees.

Second device D200 is positioned through a second surgical pathway using a lateral approach and is positioned in the space between first vertebral body V1 and second vertebral body V2 of vertebrae V percutaneously such that a bone engaging surface 201 of second device D200 engages first vertebral body V1 and a bone engaging surface 202 of second device D200 opposite bone engaging surface 201 engages second vertebral body V2. Second device is positioned such that tip 121 extends through an opening 203 in second device D200 that extends through and between bone engaging surfaces 201, 202. In some embodiments, second device D200 is inserted in the space between first vertebral body V1 and second vertebral body V2 before first device D100 is inserted into first vertebral body V1. In some embodiments, first vertebral body V1 and second vertebral body V2 are distracted relative to one another to increase the space between first vertebral body V1 and second vertebral body V2 for insertion of second device D200.

In some embodiments, second device D200 is inserted through the second surgical pathway for positioning in the space between first vertebral body V1 and second vertebral body V2 without moving the patient from a position in which first device D100 is inserted through the first surgical pathway to engage first vertebral body V1. That is, the patient is not moved or repositioned to insert second device D200 within body B for positioning in the space between first vertebral body V1 and second vertebral body V2 after inserting first device D100 into body B to engage first vertebral body V1. Likewise, in embodiments, where second device D200 is inserted before first device D100, the patient is not moved or repositioned to insert first device D100 into body B to engage first vertebral body V1 after inserting second device D200 within body B for positioning in the space between first vertebral body V1 and second vertebral body V2. In some embodiments, the patient's position is maintained between the insertion of first device D100 through the first surgical pathway to engage first vertebral body V1 and the insertion of second device D200 through the second surgical pathway for positioning in the space between first vertebral body V1 and second vertebral body V2, at least in part, by a device, such as, for example, a surgical table, a surgical bed, cushions, wedges, etc. In some embodiments, the device is a dynamic surgical table system, such as, for example, that disclosed in U.S. Pat. No. 7,234,180, which is incorporated herein by reference, in its entirety. In some embodiments, the patient is maintained in a position such that coronal plane CP of body B is disposed at an angle α, such as, for example an acute angle relative to a floor F of the operating room, as shown in FIG. 1L, for example.

In one embodiment, shown in FIGS. 3G-31, shaft 120 is cannulated and includes an opening a distal end thereof. First device D100 is positioned through a first surgical pathway using a posterior approach to engage a first vertebral body V1 of vertebrae V to the left of sagittal plane SP percutaneously. In some embodiments, first device D100 engages a portion of first vertebral body V1 between the articular process of vertebral body V1 and the transverse process of first vertebral body V1 such that head 122 is posterior to a facet of first vertebral body V1. In some embodiments, first device D100 is inserted into first vertebral body V1 such that longitudinal axis L10 extends at an angle β3 relative to sagittal plane SP. In some embodiments, angle β3 is an acute angle. In some embodiments, angle 33 is an angle between about 1 and 45 degrees. In some embodiments, first device D100 is inserted into first vertebral body V1 such that longitudinal axis L10 extends at an angle X3 relative to coronal plane CP. In some embodiments, angle X3 is an acute angle.

In some embodiments, angle X3 is an angle between about 1 and 45 degrees. In some embodiments, first device D100 is positioned through the first surgical pathway using a posterior approach to engage first vertebral body V1 to the right of sagittal plane SP percutaneously and first device D100 is inserted into first vertebral body V1 such that longitudinal axis L10 extends at an angle γ3 relative to sagittal plane SP. In some embodiments, angle γ3 is an acute angle. In some embodiments, angle γ3 is an angle between about 1 and 45 degrees.

Second device D200 is positioned through a second surgical pathway using a lateral approach and is positioned in the space between first vertebral body V1 and second vertebral body V2 of vertebrae V percutaneously such that bone engaging surface 201 engages first vertebral body V1 and bone engaging surface 202 engages second vertebral body V2. Second device is positioned such that tip 121 extends through opening 203. In some embodiments, second device D200 is inserted in the space between first vertebral body V1 and second vertebral body V2 before first device D100 is inserted into first vertebral body V1. In some embodiments, first vertebral body V1 and second vertebral body V2 are distracted relative to one another to increase the space between first vertebral body V1 and second vertebral body V2 for insertion of second device D200.

In some embodiments, second device D200 is inserted through the second surgical pathway for positioning in the space between first vertebral body V1 and second vertebral body V2 without moving the patient from a position in which first device D100 is inserted through the first surgical pathway to engage first vertebral body V1. That is, the patient is not moved or repositioned to insert second device D200 within body B for positioning in the space between first vertebral body V1 and second vertebral body V2 after inserting first device D100 into body B to engage first vertebral body V1. Likewise, in embodiments, where second device D200 is inserted before first device D100, the patient is not moved or repositioned to insert first device D100 into body B to engage first vertebral body V1 after inserting second device D200 within body B for positioning in the space between first vertebral body V1 and second vertebral body V2. In some embodiments, the patient's position is maintained between the insertion of first device D100 through the first surgical pathway to engage first vertebral body V1 and the insertion of second device D200 through the second surgical pathway for positioning in the space between first vertebral body V1 and second vertebral body V2, at least in part, by a device, such as, for example, a surgical table, a surgical bed, cushions, wedges, etc. In some embodiments, the device is a dynamic surgical table system, such as, for example, that disclosed in U.S. Pat. No. 7,234,180, which is incorporated herein by reference, in its entirety. In some embodiments, the patient is maintained in a position such that coronal plane CP of body B is disposed at an angle α, such as, for example an acute angle relative to a floor F of the operating room, as shown in FIG. 1L, for example.

In some embodiments, a guide wire is inserted to guide first device D100 into position. That is, a guide wire is inserted into first vertebral body V1. The guidewire is inserted into the cannula of first device D100. First device D100 is then slid along the guidewire to engage first device D100 with first vertebral body V1 in the manner described above.

In some embodiments, a material is introduced through the cannula of first device D100 to deliver the material into opening 203 and/or the space between first vertebral body V1 and second vertebral body V2. In some embodiments, the material is bone cement, a bone growth material, such as, for example, bone morphogenetic protein (BMP), an analgesic and/or an anti-inflammatory agent. In some embodiments, an instrument is introduced through the cannula of first device D100 to provide navigational capabilities and/or stimulate bone growth. In some embodiments, the instrument is a probe and/or electrodes.

Figure 3J:
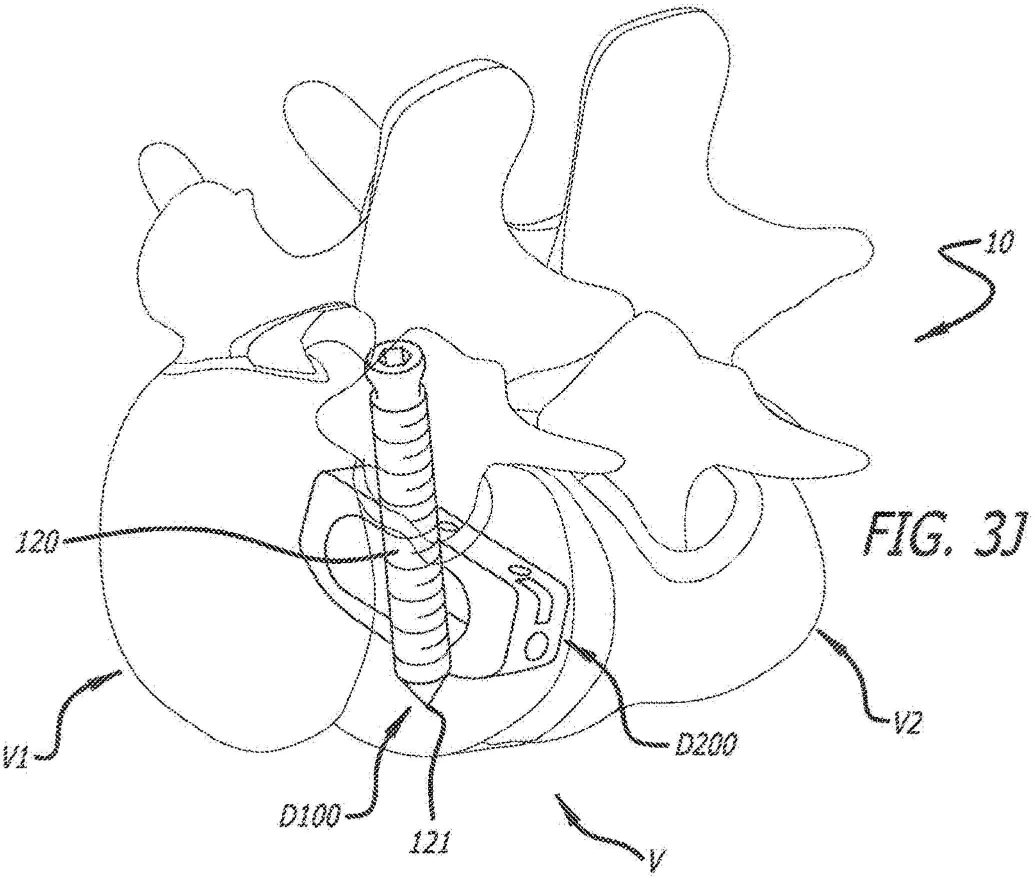
FIG. 3J is a top, perspective view, in part phantom, of first and second vertebral bodies, with a first device extending through a first incision using a posterior approach such that the first device extends through the first vertebral body and into a space between the first and second vertebral bodies, and a second device extending through a second incision using a lateral approach to position the second device in the space between the first and second vertebral bodies such that the first device engages the second device and a tip of the first device is anterior to the second device.
Figure 3K:
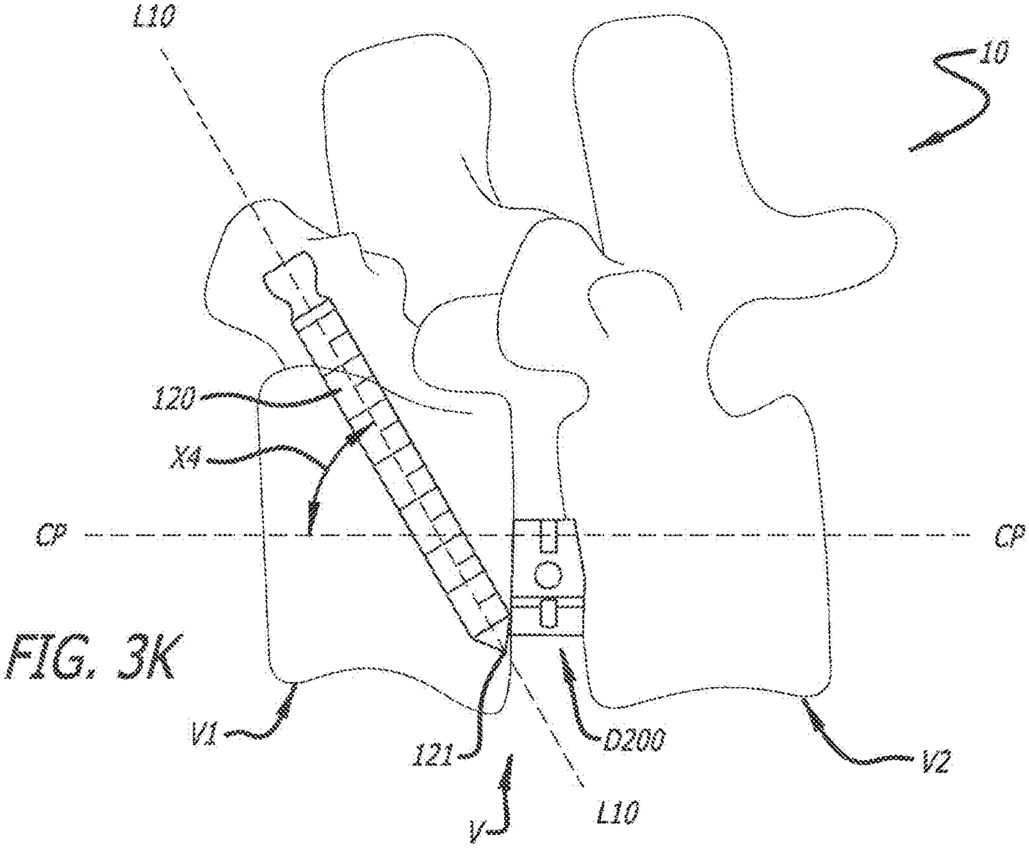
FIG. 3K is a side view, in part phantom, of the first and second vertebral bodies shown in FIG. 3J, with the first device shown in FIG. 3J extending through a first incision using a posterior approach such that the first device extends through the first vertebral body and into the space between the first and second vertebral bodies, and the second device shown in FIG. 3J extending through a second incision using a lateral approach to position the second device in the space between the first and second vertebral bodies such that the first device engages the second device and a tip of the first device is anterior to the second device.
Figure 3L:
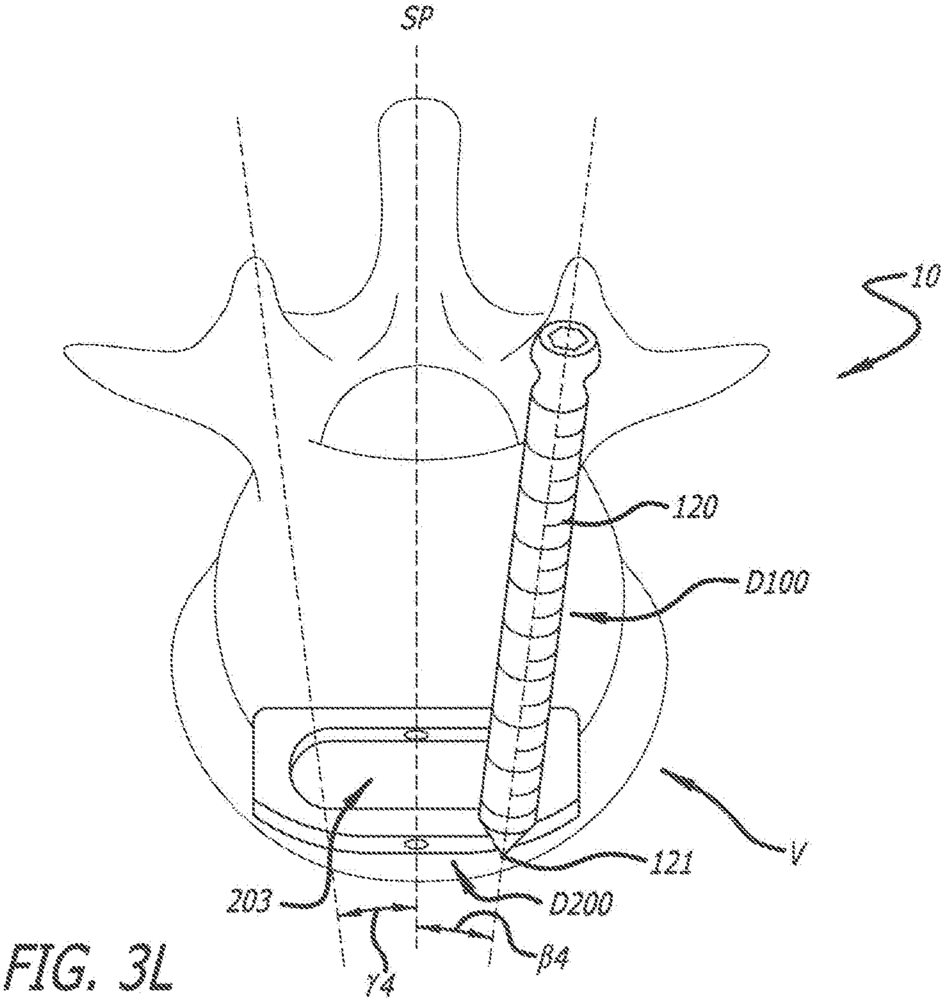
FIG. 3L is a top view, in part phantom, of the first and second vertebral bodies shown in FIG. 3J, with the first device shown in FIG. 3J extending through a first incision using a posterior approach such that the first device extends through the first vertebral body and into the space between the first and second vertebral bodies, and the second device shown in FIG. 3J extending through a second incision using a lateral approach to position the second device in the space between the first and second vertebral bodies such that the first device engages the second device and a tip of the first device is anterior to the second device.
Figure 3M:
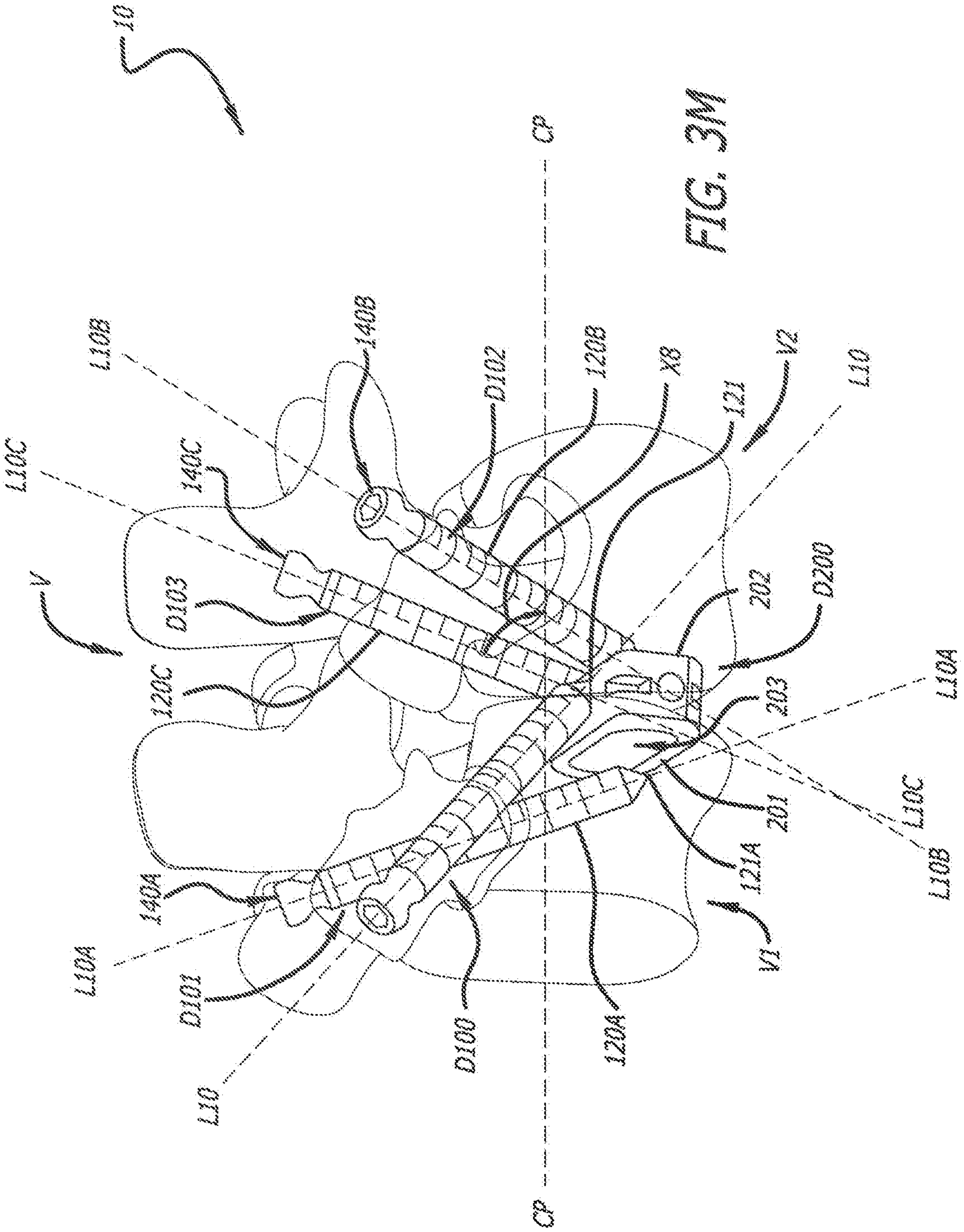
FIG. 3M is a top, perspective view, in part phantom, of first and second vertebral bodies, with a first device extending along a first surgical pathway using a posterior approach such that the first device extends through the first vertebral body and into a space between the first and second vertebral bodies, a second device extending along a second surgical pathway using a lateral approach to position the second device in the space between the first and second vertebral bodies such that the second device engages the first device, a third device extending along a third surgical pathway using a posterior approach such that the third device extends through the first vertebral body and into contact with the second device, a fourth device extending along a fourth surgical pathway using a posterior approach such that the fourth device extends through the second vertebral body and into the second device, and a fifth device extending along a fifth surgical pathway using a posterior approach such that the fifth device extends through the second vertebral body and into the second device.
Figure 3N:
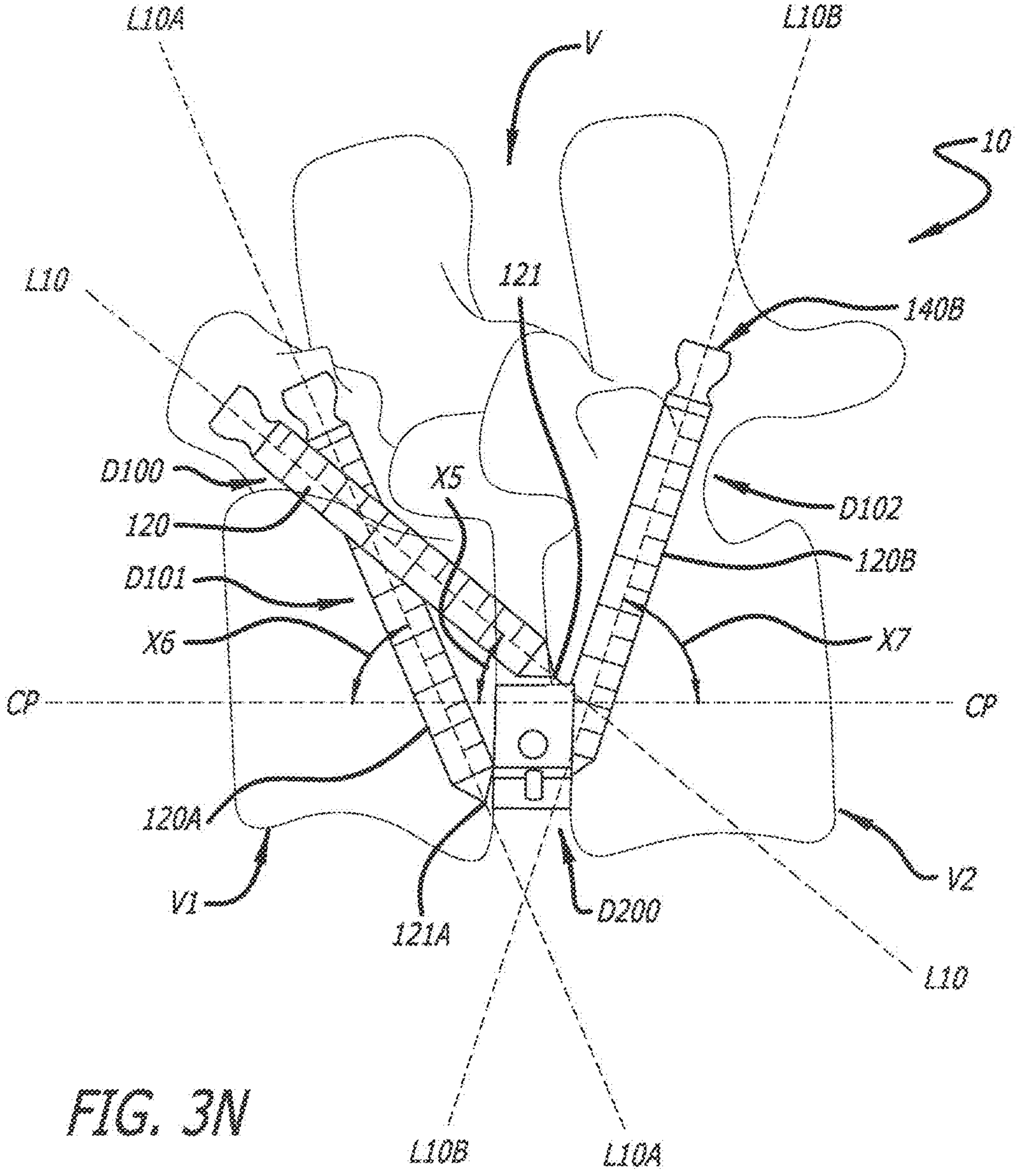
FIG. 3N is a side view, in part phantom, of the first and second vertebral bodies shown in FIG. 3M, with the first device shown in FIG. 3M extending along a first surgical pathway using a posterior approach such that the first device extends through the first vertebral body and into a space between the first and second vertebral bodies, the second device shown in FIG. 3M extending along a second surgical pathway using a lateral approach to position the second device in the space between the first and second vertebral bodies such that the second device engages the first device, the third device shown in FIG. 3M extending along a third surgical pathway using a posterior approach such that the third device extends through the first vertebral body and into contact with the second device, the fourth device shown in FIG. 3M extending along a fourth surgical pathway using a posterior approach such that the fourth device extends through the second vertebral body and into the second device, and the fifth device shown in FIG. 3M extending along a fifth surgical pathway using a posterior approach such that the fifth device extends through the second vertebral body and into the second device.
Figure 30:
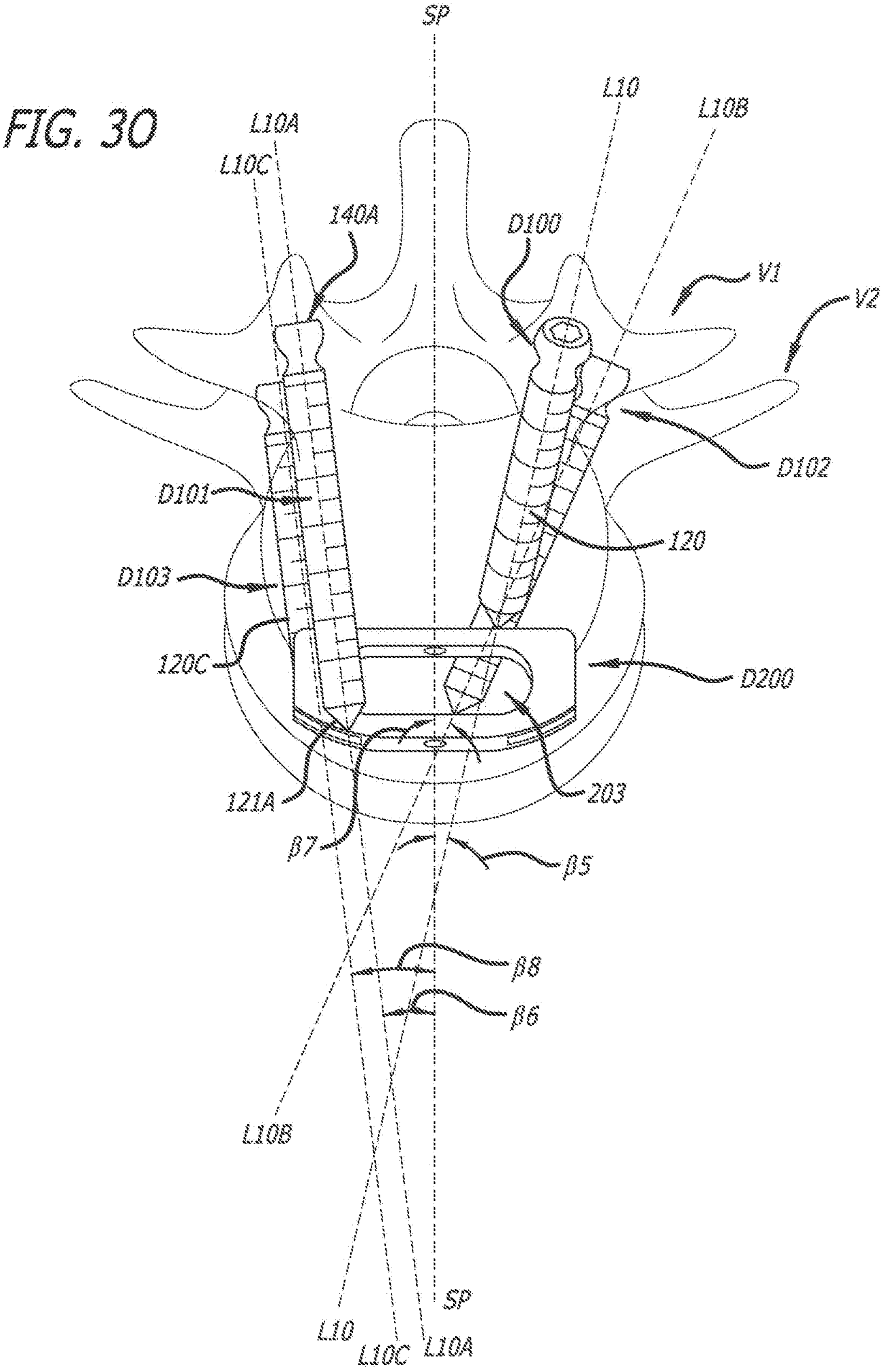
Figure 3P:
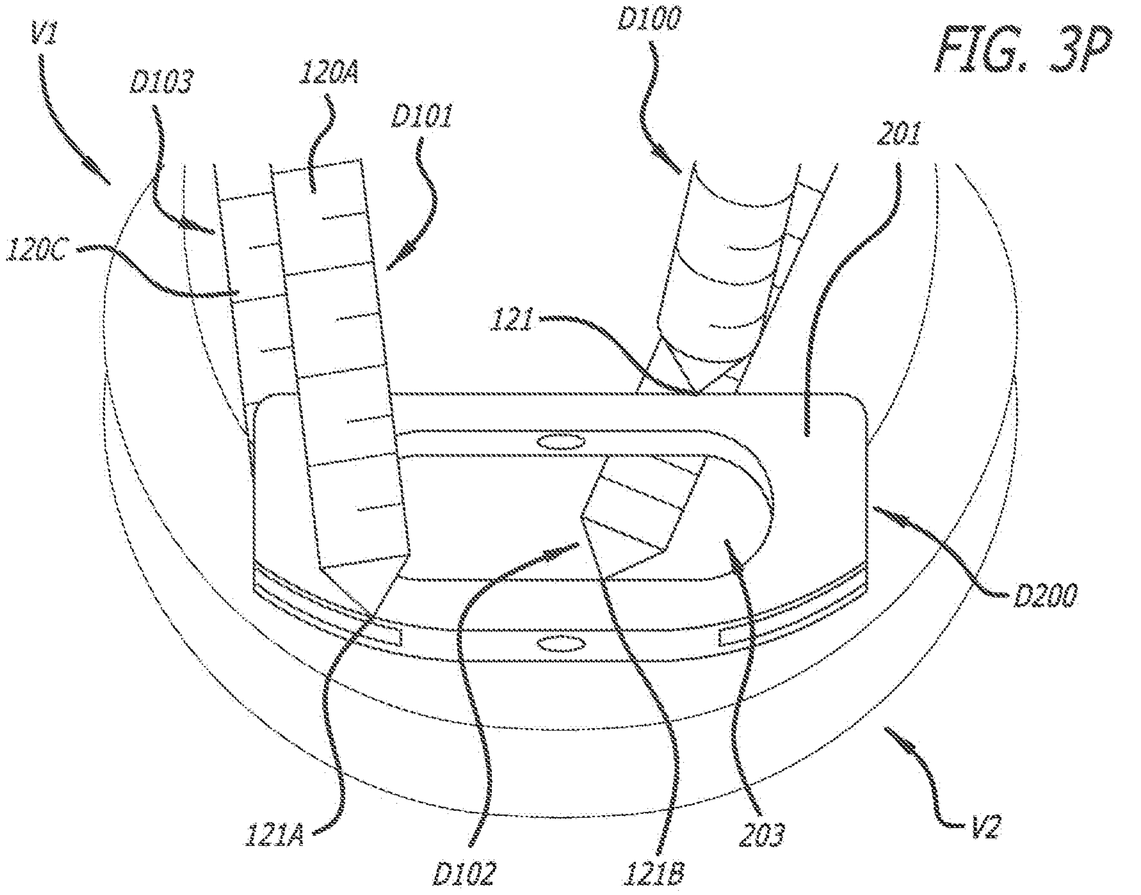
FIG. 3P is an enlarged top view, in part phantom, of the first and second vertebral bodies shown in FIG. 3M, showing the relative orientations and position of each of the first, second, third, fourth, and fifth devices shown in FIG. 3M.
Figure 3Q:
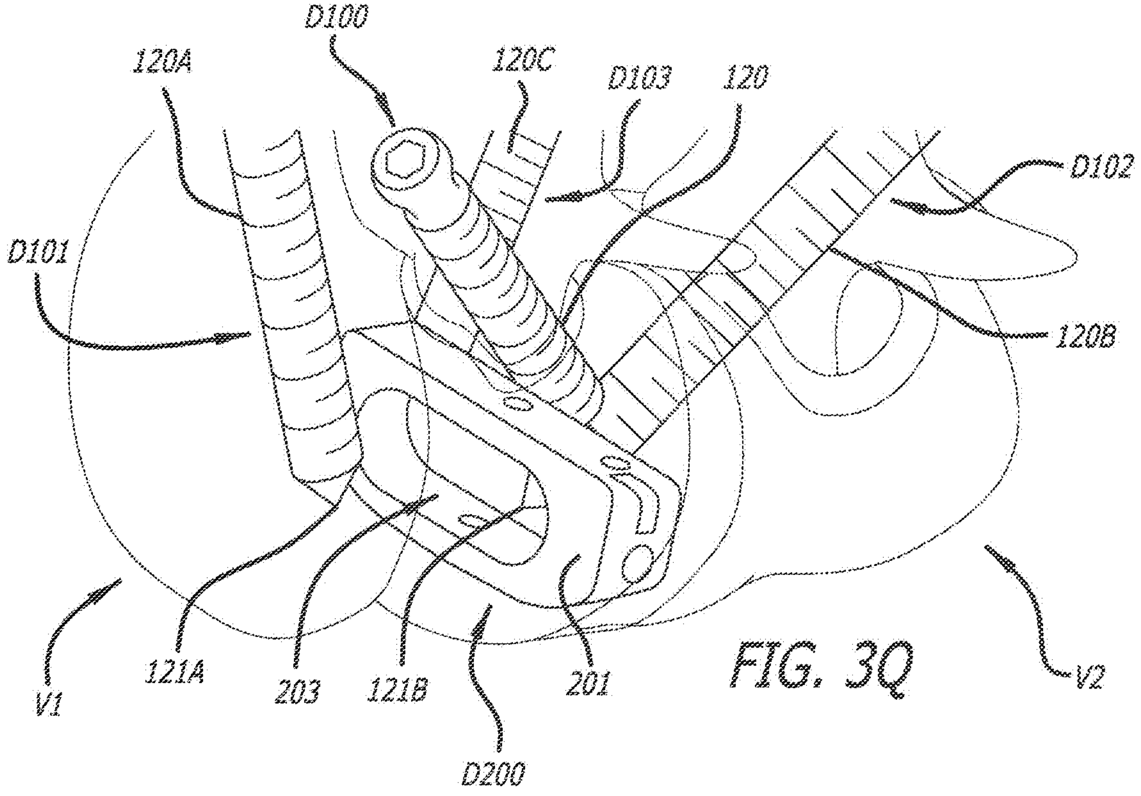
FIG. 3Q is an enlarged top, perspective view, in part phantom, of the first and second vertebral bodies shown in FIG. 3M, showing the relative orientations and position of each of the first, second, third, fourth, and fifth devices shown in FIG. 3M.

In one embodiment, shown in FIGS. 3J-3L, first device D100 is positioned through a first surgical pathway using a posterior approach to engage first vertebral body V1 to the left of sagittal plane SP percutaneously. In some embodiments, first device D100 engages a portion of first vertebral body V1 between the articular process of vertebral body V1 and the transverse process of first vertebral body V1. In some embodiments, first device D100 is inserted into first vertebral body V1 such that tip 121 is positioned in the space between first vertebral body V1 and second vertebral body V2. In some embodiments, first device D100 is inserted into first vertebral body V1 such that tip 121 is positioned in first vertebral body V1 without extending into the space between first vertebral body V1 and second vertebral body V2. In some embodiments, first device D100 is inserted into first vertebral body V1 such that longitudinal axis L10 extends at an angle β4 relative to sagittal plane SP. In some embodiments, angle β4 is an acute angle. In some embodiments, angle β4 is an angle between about 1 and 45 degrees. In some embodiments, first device D100 is inserted into first vertebral body V1 such that longitudinal axis L10 extends at an angle X4 relative to coronal plane CP. In some embodiments, angle X4 is an acute angle. In some embodiments, angle X4 is an angle between about 1 and 45 degrees.

In some embodiments, first device D100 is positioned through the first surgical pathway using a posterior approach to engage first vertebral body V1 to the right of sagittal plane SP percutaneously and first device D100 is inserted into first vertebral body V1 such that longitudinal axis L10 extends at an angle γ4 relative to sagittal plane SP. In some embodiments, angle γ4 is an acute angle. In some embodiments, angle γ4 is an angle between about 1 and 45 degrees.

Second device D200 is positioned through a second surgical pathway using a lateral approach and is positioned in the space between first vertebral body V1 and second vertebral body V2 of vertebrae V percutaneously such that tip 121 is anterior to second device D200. Second device D200 is positioned in the space between first vertebral body V1 and second vertebral body V2 such that second device D200 is spaced apart from first device D100. In some embodiments, second device D200 is inserted in the space between first vertebral body V1 and second vertebral body V2 before first device D100 is inserted into first vertebral body V1. In some embodiments, first vertebral body V1 and second vertebral body V2 are distracted relative to one another to increase the space between first vertebral body V1 and second vertebral body V2 for insertion of second device D200.

In some embodiments, second device D200 is inserted through the second surgical pathway for positioning in the space between first vertebral body V1 and second vertebral body V2 without moving the patient from a position in which first device D100 is inserted through the first surgical pathway to engage first vertebral body V1. That is, the patient is not moved or repositioned to insert second device D200 within body B for positioning in the space between first vertebral body V1 and second vertebral body V2 after inserting first device D100 into body B to engage first vertebral body V1. Likewise, in embodiments, where second device D200 is inserted before first device D100, the patient is not moved or repositioned to insert first device D100 into body B to engage first vertebral body V1 after inserting second device D200 within body B for positioning in the space between first vertebral body V1 and second vertebral body V2. In some embodiments, the patient's position is maintained between the insertion of first device D100 through the first surgical pathway to engage first vertebral body V1 and the insertion of second device D200 through the second surgical pathway for positioning in the space between first vertebral body V1 and second vertebral body V2, at least in part, by a device, such as, for example, a surgical table, a surgical bed, cushions, wedges, etc. In some embodiments, the device is a dynamic surgical table system, such as, for example, that disclosed in U.S. Pat. No. 7,234,180, which is incorporated herein by reference, in its entirety. In some embodiments, the patient is maintained in a position such that coronal plane CP of body B is disposed at an angle α, such as, for example an acute angle relative to a floor F of the operating room, as shown in FIG. 1L, for example.

In one embodiment, shown in FIGS. 3M-3S, first device D100 is positioned through a first surgical pathway using a posterior approach to engage a first vertebral body V1 of vertebrae V to the left of sagittal plane SP percutaneously. In some embodiments, first device D100 engages a portion of first vertebral body V1 between the articular process of vertebral body V1 and the transverse process of first vertebral body V1. In some embodiments, first device D100 is inserted into first vertebral body V1 such that tip 121 is positioned in the space between first vertebral body V1 and second vertebral body V2. In some embodiments, first device D100 is inserted into first vertebral body V1 such that tip 121 is oriented in a caudal direction. In some embodiments, first device D100 is inserted into first vertebral body V1 such that longitudinal axis L10 extends at an angle β5 relative to sagittal plane SP. In some embodiments, angle β5 is an acute angle. In some embodiments, angle β5 is an angle between about 1 and 45 degrees. In some embodiments, first device D100 is inserted into first vertebral body V1 such that longitudinal axis L10 extends at an angle X5 relative to coronal plane CP. In some embodiments, angle X5 is an acute angle. In some embodiments, angle X5 is an angle between about 1 and 45 degrees.

Second device D200 is positioned through a second surgical pathway using a lateral approach and is positioned in the space between first vertebral body V1 and second vertebral body V2 of vertebrae V percutaneously such that surface 201 engages first vertebral body V1, surface 202 engages second vertebral body V2 and tip 121 is posterior to second device D200. In some embodiments, second device D200 is positioned in the space between first vertebral body V1 and second vertebral body V2 such that tip 121 engages second device D200. In some embodiments, second device D200 is positioned in the space between first vertebral body V1 and second vertebral body V2 such that second device D200 is spaced apart from first device D100. In some embodiments, second device D200 is inserted in the space between first vertebral body V1 and second vertebral body V2 before first device D100 is inserted into first vertebral body V1. In some embodiments, first vertebral body V1 and second vertebral body V2 are distracted relative to one another to increase the space between first vertebral body V1 and second vertebral body V2 for insertion of second device D200.

In some embodiments, second device D200 is inserted through the second surgical pathway for positioning in the space between first vertebral body V1 and second vertebral body V2 without moving the patient from a position in which first device D100 is inserted through the first surgical pathway to engage first vertebral body V1. That is, the patient is not moved or repositioned to insert second device D200 within body B for positioning in the space between first vertebral body V1 and second vertebral body V2 after inserting first device D100 into body B to engage first vertebral body V1. Likewise, in embodiments, where second device D200 is inserted before first device D100, the patient is not moved or repositioned to insert first device D100 into body B to engage first vertebral body V1 after inserting second device D200 within body B for positioning in the space between first vertebral body V1 and second vertebral body V2. In some embodiments, the patient's position is maintained between the insertion of first device D100 through the first surgical pathway to engage first vertebral body V1 and the insertion of second device D200 through the second surgical pathway for positioning in the space between first vertebral body V1 and second vertebral body V2, at least in part, by a device, such as, for example, a surgical table, a surgical bed, cushions, wedges, etc. In some embodiments, the device is a dynamic surgical table system, such as, for example, that disclosed in U.S. Pat. No. 7,234,180, which is incorporated herein by reference, in its entirety. In some embodiments, the patient is maintained in a position such that coronal plane CP of body B is disposed at an angle α, such as, for example an acute angle relative to a floor F of the operating room, as shown in FIG. 1L, for example.

A third device D101, such as, for example, a bone screw similar to first device D100 is positioned through a third surgical pathway using a posterior approach such that a shaft 120A of third device D101 extends through first vertebral body V1. In some embodiments, third device D101 extends through first vertebral body V1 such that a tip 121A of third device D101 extends in a caudal direction and engages surface 201. In some embodiments, third device D101 extends through first vertebral body V1 such that tip 121A is anterior to tip 121. In some embodiments, third device D101 extends through first vertebral body V1 such that tip 121A extends in a caudal direction and is positioned in opening 203. In some embodiments, a pilot hole is made in first vertebral body V1 for third device D101 and third device D101 is inserted into the pilot hole such that threads on the outer surface of a shaft 120A of third device D101 engage a portion of first vertebral body V1 that define the pilot hole and third device D101 is rotated about a longitudinal axis L1OA defined by shaft 120A until third device D101 threadingly engages first vertebral body V1. In some embodiments, third device D101 is threaded into the pilot hole and/or first vertebral body V1 using an instrument, such as, for example, a driver that engages a tool engaging portion 140A of shaft 120A. In some embodiments, third device D101 is threaded into first vertebral body V1 using a surgical drill, such as, for example, a drill and/or tap included in the POWER EASE™ System sold by Medtronic. In some embodiments, third device D101 is inserted into first vertebral body V1 such that longitudinal axis L1OA extends at an angle β6 relative to sagittal plane SP. In some embodiments, angle β6 is an acute angle. In some embodiments, angle β6 is an angle between about 1 and 45 degrees. In some embodiments, third device D101 is inserted into first vertebral body V1 such that longitudinal axis L1OA extends at an angle X6 relative to coronal plane CP. In some embodiments, angle X6 is an acute angle. In some embodiments, angle X6 is an angle between about 1 and 45 degrees.

In some embodiments, third device D101 is inserted into first vertebral body V1 before first device D100 is inserted into first vertebral body V1. In some embodiments, third device D101 is inserted into first vertebral body V1 after first device D100 is inserted into first vertebral body V1. In some embodiments, third device D101 is inserted into first vertebral body V1 without moving the patient from a position in which second device D200 is inserted into the space between first vertebral body V1 and second vertebral body V2 and/or first device D100 is inserted into first vertebral body V1. That is, the patient is not moved or repositioned to insert third device D101 into first vertebral body V1 such that tip 121A engages second device D200 and/or is positioned within opening 203 after second device D200 is inserted within body B in the space between first vertebral body V1 and second vertebral body V2 and/or first device D100 is inserted into first vertebral body V1 such that tip 121 engages second device D200. In some embodiments, the patient's position is maintained between the insertion of third device D101 into first vertebral body V1 and the insertion of second device D200 into the space between first vertebral body V1 and second vertebral body V2 and/or the insertion of first device D100 into first vertebral body V1, at least in part, by a device, such as, for example, a surgical table, a surgical bed, cushions, wedges, etc. In some embodiments, the device is a dynamic surgical table system, such as, for example, that disclosed in U.S. Pat. No. 7,234,180, which is incorporated herein by reference, in its entirety. In some embodiments, the patient is maintained in a position such that coronal plane CP of body B is disposed at an angle α, such as, for example an acute angle relative to a floor F of the operating room, as shown in FIG. 1L, for example.

A fourth device D102, such as, for example, a bone screw similar to first device D100 and third device D101 is positioned through a fourth surgical pathway using a posterior approach such that a shaft 120B of fourth device D102 extends through second vertebral body V2. In some embodiments, fourth device D102 extends through second vertebral body V2 such that a tip 121B of fourth device D102 extends in a cranial direction and is positioned in opening 203. In some embodiments, fourth device D102 extends through second vertebral body V2 such that tip 121B is anterior to tip 121 and posterior to tip 121A. In some embodiments, a pilot hole is made in second vertebral body V2 for fourth device D102 and fourth device D102 is inserted into the pilot hole such that threads on the outer surface of a shaft 120B of fourth device D102 engage a portion of second vertebral body V2 that define the pilot hole and fourth device D102 is rotated about a longitudinal axis L10B defined by shaft 120B until fourth device D102 threadingly engages second vertebral body V2. In some embodiments, fourth device D102 is threaded into the pilot hole and/or second vertebral body V2 using an instrument, such as, for example, a driver that engages a tool engaging portion 140B of shaft 120B. In some embodiments, fourth device D102 is threaded into second vertebral body V2 using a surgical drill, such as, for example, a drill and/or tap included in the POWEREASE™ System sold by Medtronic. In some embodiments, fourth device D102 is inserted into second vertebral body V2 such that longitudinal axis L10B extends at an angle β7 relative to sagittal plane SP. In some embodiments, angle β7 is an acute angle. In some embodiments, angle β7 is an angle between about 1 and 45 degrees. In some embodiments, fourth device D102 is inserted into second vertebral body V2 such that longitudinal axis L10B extends at an angle X7 relative to coronal plane CP. In some embodiments, angle X7 is an acute angle. In some embodiments, angle X7 is an angle between about 1 and 45 degrees.

In some embodiments, fourth device D102 is inserted into second vertebral body V2 before first device D100 is inserted into first vertebral body V1 and/or third device D101 is inserted into first vertebral body V1. In some embodiments, fourth device D102 is inserted into second vertebral body V2 after first device D100 is inserted into first vertebral body V1 and/or third device D101 is inserted into first vertebral body V1. In some embodiments, first device D100 is inserted into first vertebral body V1, third device D101 is inserted into first vertebral body V1 and/or fourth device D102 is inserted into second vertebral body V2 without moving the patient from a position in which second device D200 is inserted into the space between first vertebral body V1 and second vertebral body V2. That is, the patient is not moved or repositioned to insert fourth device D102 into second vertebral body V2, first device D100 in first vertebral body V1 and/or third device D101 in first vertebral body V1 after second device D200 is inserted within body B in the space between first vertebral body V1 and second vertebral body V2. In some embodiments, the patient's position is maintained between the insertion of first device D100 into first vertebral body V1, the insertion of third device D101 into first vertebral body V1, the insertion of fourth device D102 into second vertebral body V2 and/or the insertion of second device D200 into the space between first vertebral body V1 and second vertebral body V2, at least in part, by a device, such as, for example, a surgical table, a surgical bed, cushions, wedges, etc. In some embodiments, the device is a dynamic surgical table system, such as, for example, that disclosed in U.S. Pat. No. 7,234,180, which is incorporated herein by reference, in its entirety. In some embodiments, the patient is maintained in a position such that coronal plane CP of body B is disposed at an angle α, such as, for example an acute angle relative to a floor F of the operating room, as shown in FIG. 1L, for example.

A fifth device D103, such as, for example, a bone screw similar to first device D100, third device D101 and fourth device D102 is positioned through a fifth surgical pathway using a posterior approach such that a shaft 120C of fifth device D103 extends through second vertebral body V2. In some embodiments, fifth device D103 extends through second vertebral body V2 such that a tip 121C of fifth device D103 extends in a cranial direction and engages surface 202. In some embodiments, fifth device D103 extends through second vertebral body V2 such that tip 121C is anterior to tips 121, 121B and posterior to tip 121A. In some embodiments, a pilot hole is made in second vertebral body V2 for fifth device D103 and fifth device D103 is inserted into the pilot hole such that threads on the outer surface of a shaft 120C of fifth device D103 engage a portion of second vertebral body V2 that define the pilot hole and fifth device D103 is rotated about a longitudinal axis L1OC defined by shaft 120C until fifth device D103 threadingly engages second vertebral body V2. In some embodiments, fifth device D103 is threaded into the pilot hole and/or second vertebral body V2 using an instrument, such as, for example, a driver that engages a tool engaging portion 140C of shaft 120C. In some embodiments, fifth device D103 is threaded into second vertebral body V2 using a surgical drill, such as, for example, a drill and/or tap included in the POWEREASE™ System sold by Medtronic. In some embodiments, fifth device D103 is inserted into second vertebral body V2 such that longitudinal axis L1OC extends at an angle β8 relative to sagittal plane SP. In some embodiments, angle β8 is an acute angle. In some embodiments, angle β8 is an angle between about 1 and 45 degrees. In some embodiments, fifth device D103 is inserted into second vertebral body V2 such that longitudinal axis L1OC extends at an angle X8 relative to coronal plane CP. In some embodiments, angle X8 is an acute angle. In some embodiments, angle X8 is an angle between about 1 and 45 degrees.

In some embodiments, fifth device D103 is inserted into second vertebral body V2 before first device D100 is inserted into first vertebral body V1, third device D101 is inserted into first vertebral body V1 and/or fourth device D102 is inserted into second vertebral body. In some embodiments, fourth device D102 is inserted into second vertebral body V2 after first device D100 is inserted into first vertebral body V1, third device D101 is inserted into first vertebral body V1 and/or fourth device D102 is inserted into second vertebral body. In some embodiments, first device D100 is inserted into first vertebral body V1, third device D101 is inserted into first vertebral body V1, fourth device D102 is inserted into second vertebral body V2 and/or fifth device D103 is inserted into second vertebral body V2 without moving the patient from a position in which second device D200 is inserted into the space between first vertebral body V1 and second vertebral body V2. That is, the patient is not moved or repositioned to insert fifth device D103 into second vertebral body V2, first device D100 in first vertebral body V1, third device D101 in first vertebral body V1 and/or fourth device D102 in second vertebral body V2 after second device D200 is inserted within body B in the space between first vertebral body V1 and second vertebral body V2. In some embodiments, the patient's position is maintained between the insertion of first device D100 into first vertebral body V1, the insertion of third device D101 into first vertebral body V1, the insertion of fourth device D102 into second vertebral body V2, the insertion of fifth device D103 into second vertebral body V2 and/or the insertion of second device D200 into the space between first vertebral body V1 and second vertebral body V2, at least in part, by a device, such as, for example, a surgical table, a surgical bed, cushions, wedges, etc. In some embodiments, the device is a dynamic surgical table system, such as, for example, that disclosed in U.S. Pat. No. 7,234,180, which is incorporated herein by reference, in its entirety. In some embodiments, the patient is maintained in a position such that coronal plane CP of body B is disposed at an angle α, such as, for example an acute angle relative to a floor F of the operating room, as shown in FIG. 1L, for example.

In any of the embodiments shown in FIGS. 3A-3S, at least one of first, second, third, fourth and fifth devices D100, D200, D101, D102, D103 may be inserted into body B using an instrument, such as, for example, an instrument having integrated neuromonitoring and/or navigation capabilities. In some embodiments, the instrument having integrated neuromonitoring and/or navigation capabilities is used to establish and/or monitor the trajectories of at least one of first, second, third, fourth and fifth devices D100, D200, D101, D102, D103. That is, the instrument having integrated neuromonitoring and/or navigation capabilities may be used to determine and/or select a safe trajectory in relation to the patient's anatomy for at least one first, second, third, fourth and fifth devices D100, D200, D101, D102, D103, even as that anatomy shifts in real-time and/or ensure that at least one of first, second, third, fourth and fifth devices D100, D200, D101, D102, D103 is being inserted and/or implanted using the selected trajectory. In some embodiments, the instrument having integrated neuromonitoring and/or navigation capabilities is part of a navigation system sold by Medtronic, such as, for example, StealthStation® S7®, StealthStation i7™, StealthStation iNav®, AxiEM Electromagnetic Navigation System, Fusion™ ENT and/or StealthViz™ Planning Station. In some embodiments, the instrument having integrated neuromonitoring and/or navigation capabilities aids a medical practitioner to perform safer, more precise procedure, reduce procedure invasiveness and risk and/or improve patient outcomes and recovery.

In any of the embodiments shown in FIGS. 3A-3S, imaging may be used to establish and/or monitor the trajectories of at least one of first, second, third, fourth and fifth devices D100, D200, D101, D102, D103 through incisions using the approaches discussed above. In one embodiment, an imaging system, such as, for example, the O-arm Surgical Imaging System available from Medtronic is used to establish and/or monitor the trajectories of at least one of first, second, third, fourth and fifth devices D100, D200, D101, D102, D103 using intra-operative imaging. The O-arm Surgical Imaging System, among other things, provides fast access to real-time, multi-plane 3D images (and 2D images), provides full support of the unique workflow of procedures, such as, for example, spinal procedures, minimizes radiation dose for surgical staff (by reducing X-ray exposure, for example) and provides visualization to confirm hardware therapy placement, potentially eliminating revision surgeries.

In any of the embodiments shown in FIGS. 3A-3S, at least one of first, third, fourth and fifth devices D100, D101, D10, D103 may be cannulated. In some embodiments, a guide wire is inserted to guide at least one of first, third, fourth and fifth devices D100, D101, D10, D103 into position relative to vertebrae V in the manner discussed above. That is, at least one guide wire is inserted into first vertebral body V1 and/or second vertebral body V2. One of the guidewires is inserted into the cannula of one of first, third, fourth and fifth devices D100, D101, D10, D103. First, third, fourth and fifth devices D100, D101, D10, D103 are then slid along the guidewires to engage first, second and third devices D10, D20, D30 with vertebrae V in the manner described above.

In any of the embodiments shown in FIGS. 3A-3S, at least one of first, third, fourth and fifth devices D100, D101, D10, D103 is a cannulated screw without fenestrations and/or a cannulated screw having at least one lateral fenestration that is in communication with the cannula. In some embodiments, a material is introduced through the cannulae and/or fenestrations of at least one of first, third, fourth and fifth devices D100, D101, D10, D103 to deliver the material within second device D200, such as, for example, within opening 203 or to deliver the material to first vertebral body V1 and/or second vertebral body V2. In some embodiments, the material is bone cement, a bone growth material, such as, for example, bone morphogenetic protein (BMP), an analgesic and/or an anti-inflammatory agent. In some embodiments, an instrument is introduced through the cannulae and/or fenestrations of at least one of first, third, fourth and fifth devices D100, D101, D10, D103 to provide navigational capabilities and/or stimulate bone growth. In some embodiments, the instrument is a probe and/or electrodes.

Figure 4C:
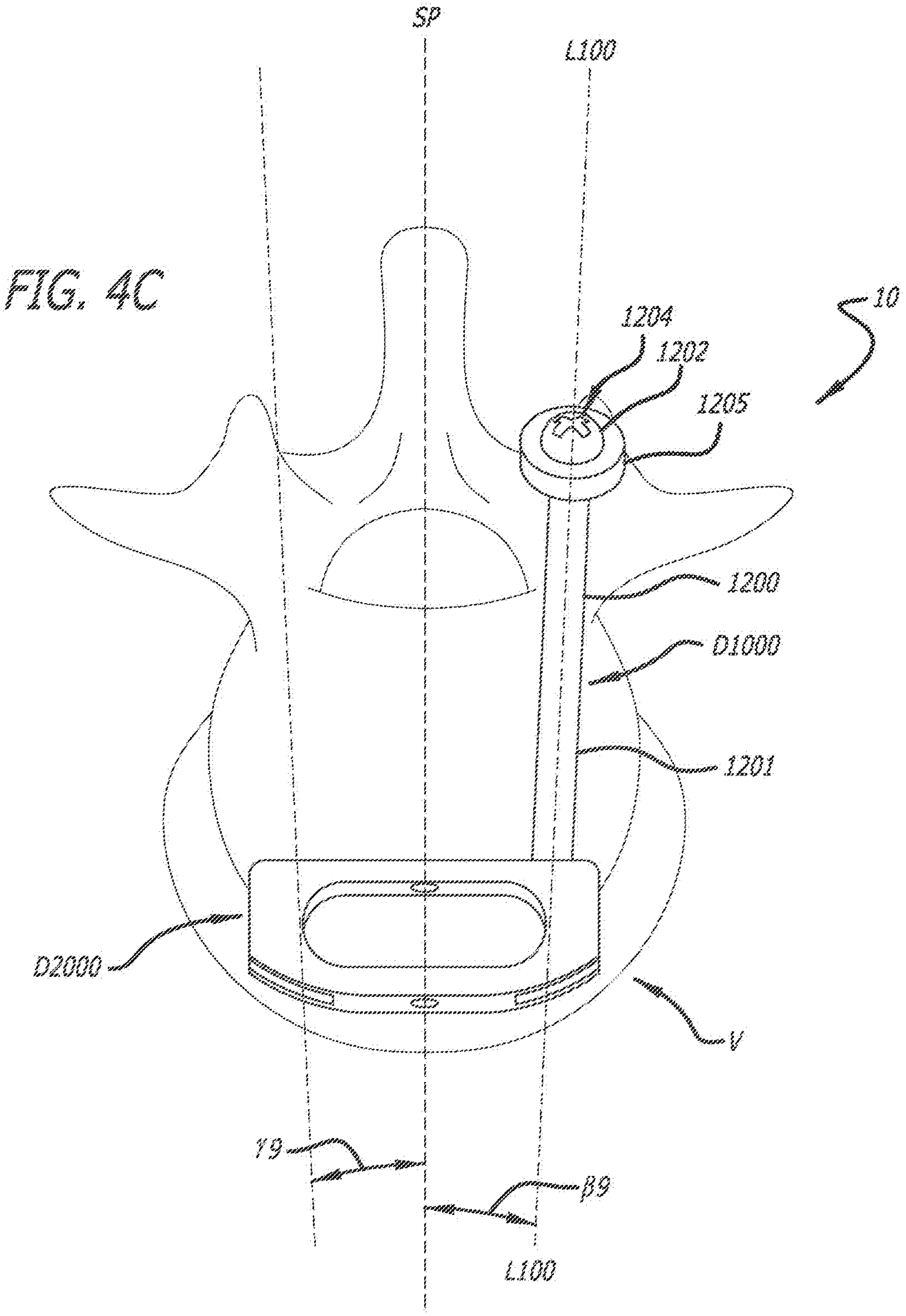
FIG. 4C is a top view, in part phantom, of the first and second vertebral bodies shown in FIG. 4A, with the first device shown in FIG. 4A extending through a first incision using a posterior approach such that the first device extends through the first vertebral body and into the second vertebral body, and the second device shown in FIG. 4A extending through a second incision using a lateral approach to position the second device in a space between the first and second vertebral bodies.

In one embodiment, shown in FIGS. 4A-4C, a first device D1000, such as, for example, a compression screw, is positioned through a first surgical pathway using a posterior approach to engage a first vertebral body V1 and a second vertebral body V2 of vertebrae V to the left of sagittal plane SP percutaneously. In some embodiments, first device D1000 engages a portion of first vertebral body V1 between the articular process of vertebral body V1 and the transverse process of first vertebral body V1 and extends into a body of second vertebral body V2. In some embodiments, a shaft 1200 of first device D1000 includes an unthreaded portion 1201 connected to a head 1202 of first device D1000 and a threaded portion 1203 is connected to unthreaded portion 1201. Threaded portion 1203 defines a tip 1210 of first device D1000. In some embodiments, unthreaded portion 1201 extends through first vertebral body V1 and across a space between first vertebral body V1 and second vertebral body V2 such that threaded portion 1203 extends into second vertebral body V2. In some embodiments, first device D1000 includes a washer 1205 that shaft 1200 extends through such that washer 1205 is slidable along shaft 1200. Washer 1205 engages first vertebral body V1 as shaft 1200 is inserted through first vertebral body V1 and into second vertebral body V2. In some embodiments, further rotation of first device D1000 about axis L100 causes washer 1205 to engage first vertebral body V1 in a manner that draws first vertebral body V1 toward second vertebral body V2. That is, the distance between first vertebral body V1 and second vertebral body V2 decreases.

In some embodiments, a pilot hole is made in first vertebral body V1 and/or second vertebral body V2 for first device D1000 and first device D1000 is inserted into the pilot hole in first vertebral body V1 such that threads on the outer surface of threaded portion 1203 engage a portion of first vertebral body V1 that defines the pilot hole in first vertebral body V1. First device D1000 is rotated about longitudinal axis L100 until unthreaded portion 1201 extends through first vertebral body V1 and space between first vertebral body V1 and second vertebral body V2 and the threads of threaded portion 1203 engage a portion of second vertebral body V2 that defines the pilot hole in second vertebral body V2. In some embodiments, first device D1000 is threaded into the pilot hole(s) and/or first vertebral body V1 and second vertebral body V2 using an instrument, such as, for example, a driver that engages a tool engaging portion 1204 of head 1202. In some embodiments, first device D1000 is threaded into first vertebral body V1 and second vertebral body V2 using a surgical drill, such as, for example, a drill included in the POWEREASE™ System sold by Medtronic.

In some embodiments, first device D1000 is inserted into first vertebral body V1 and second vertebral body V2 such that longitudinal axis L100 extends at an angle β9 relative to sagittal plane SP. In some embodiments, angle β9 is an acute angle. In some embodiments, angle β9 is an angle between about 1 and 45 degrees. In some embodiments, first device D1000 is inserted into first vertebral body V1 and second vertebral body V2 such that longitudinal axis L100 extends at an angle X9 relative to coronal plane CP. In some embodiments, angle X9 is an acute angle. In some embodiments, angle X9 is an angle between about 1 and 45 degrees. In some embodiments, shaft 1200 can be variously configured, such as, for example, smooth, ringed and/or have various cross sectional configurations, such as, for example, square, polygonal or round.

In some embodiments, first device D1000 is positioned through the first surgical pathway using a posterior approach to extend through first vertebral body V1 to the right of sagittal plane SP percutaneously and first device D1000 is inserted into first vertebral body V1 such that longitudinal axis L100 extends at an angle γ9 relative to sagittal plane SP. In some embodiments, angle γ9 is an acute angle. In some embodiments, angle γ9 is an angle between about 1 and 45 degrees.

A second device D2000, such as, for example, an interbody implant, is positioned through a second surgical pathway using a lateral approach and is positioned in the space between first vertebral body V1 and second vertebral body V2 of vertebrae V percutaneously such that second device D2000 is spaced apart from first device D1000. In some embodiments, second device D2000 is inserted in the space between first vertebral body V1 and second vertebral body V2 before first device D1000 is inserted into first vertebral body V1. In some embodiments, first vertebral body V1 and second vertebral body V2 are distracted relative to one another to increase the space between first vertebral body V1 and second vertebral body V2 for insertion of second device D2000. In some embodiments, second device D2000 is an interbody implant, a trial implant, a SCISSOR JACK® implant, an inflatable implant or one or more Fernstrom balls.

In some embodiments, second device D2000 is inserted through the second surgical pathway for positioning in the space between first vertebral body V1 and second vertebral body V2 without moving the patient from a position in which first device D1000 is inserted through the first surgical pathway to extend through first vertebral body V1 and engage second vertebral body V2. That is, the patient is not moved or repositioned to insert second device D2000 within body B for positioning in the space between first vertebral body V1 and second vertebral body V2 after inserting first device D1000 into body B to extend through first vertebral body V1 and engage second vertebral body V2. Likewise, in embodiments, where second device D2000 is inserted before first device D1000, the patient is not moved or repositioned to insert first device D1000 into body B to extend through first vertebral body V1 and engage second vertebral body V2 after inserting second device D2000 within body B for positioning in the space between first vertebral body V1 and second vertebral body V2. In some embodiments, the patient's position is maintained between the insertion of first device D1000 through the first surgical pathway to extend through first vertebral body V1 and engage second vertebral body V2 and the insertion of second device D2000 through the second surgical pathway for positioning in the space between first vertebral body V1 and second vertebral body V2, at least in part, by a device, such as, for example, a surgical table, a surgical bed, cushions, wedges, etc. In some embodiments, the device is a dynamic surgical table system, such as, for example, that disclosed in U.S. Pat. No. 7,234,180, which is incorporated herein by reference, in its entirety. In some embodiments, the patient is maintained in a position such that coronal plane CP of body B is disposed at an angle α, such as, for example an acute angle relative to a floor F of the operating room, as shown in FIG. 1L, for example.

In some embodiments, at least one of first and second devices D1000, D2000 may be inserted into body B using an instrument, such as, for example, an instrument having integrated neuromonitoring and/or navigation capabilities. In some embodiments, the instrument having integrated neuromonitoring and/or navigation capabilities is used to establish and/or monitor the trajectories of at least one of first and second devices D1000, D2000. That is, the instrument having integrated neuromonitoring and/or navigation capabilities may be used to determine and/or select a safe trajectory in relation to the patient's anatomy for at least one first and second devices D1000, D2000, even as that anatomy shifts in real-time and/or ensure that at least one of first and second devices D1000, D2000 is being inserted and/or implanted using the selected trajectory. In some embodiments, the instrument having integrated neuromonitoring and/or navigation capabilities is part of a navigation system sold by Medtronic, such as, for example, StealthStation® S7®, StealthStation i7™, StealthStation iNav®, AxiEM Electromagnetic Navigation System, Fusion™ ENT and/or StealthViz™ Planning Station. In some embodiments, the instrument having integrated neuromonitoring and/or navigation capabilities aids a medical practitioner to perform safer, more precise procedure, reduce procedure invasiveness and risk and/or improve patient outcomes and recovery.

In some embodiments, imaging may be used to establish and/or monitor the trajectories of at least one of first and second devices D1000, D2000 through incisions using the approaches discussed above. In one embodiment, an imaging system, such as, for example, the O-arm Surgical Imaging System available from Medtronic is used to establish and/or monitor the trajectories of at least one of first and second devices D1000, D2000 using intra-operative imaging. The O-arm Surgical Imaging System, among other things, provides fast access to real-time, multi-plane 3D images (and 2D images), provides full support of the unique workflow of procedures, such as, for example, spinal procedures, minimizes radiation dose for surgical staff (by reducing X-ray exposure, for example) and provides visualization to confirm hardware therapy placement, potentially eliminating revision surgeries.

In some embodiments, first device D1000 may be cannulated. In some embodiments, a guide wire is inserted to guide first device D1000 into position relative to vertebrae V in the manner discussed above. That is, a guide wire is inserted into first vertebral body V1 and/or second vertebral body V2. The guidewire is inserted into the cannula of first device D1000. First device D1000 is then slid along the guidewire to engage first device D1000 with vertebrae V in the manner described above.

In some embodiments, first device D1000 is a cannulated screw without fenestrations and/or a cannulated screw having at least one lateral fenestration that is in communication with the cannula. In some embodiments, a material is introduced through the cannula and/or fenestrations of first device D1000 to deliver the material within second device D2000, such as, for example, an opening of second device D2000 or to deliver the material to first vertebral body V1 and/or second vertebral body V2. In some embodiments, the material is bone cement, a bone growth material, such as, for example, bone morphogenetic protein (BMP), an analgesic and/or an anti-inflammatory agent. In some embodiments, an instrument is introduced through the cannula and/or fenestrations of first device D1000 to provide navigational capabilities and/or stimulate bone growth. In some embodiments, the instrument is a probe and/or electrodes.

Upon completion of a procedure, as described herein, the surgical instruments, assemblies and non-implanted components of system 10 are removed and the incision(s) are closed. One or more of the components of system 10 can be made of radiolucent materials such as polymers. Radiopaque markers may be included for identification under x-ray, fluoroscopy, CT or other imaging techniques. In some embodiments, the use of surgical navigation, microsurgical and image guided technologies, as described herein, may be employed to access, view and repair spinal deterioration or damage, with the aid of system 10. In some embodiments, system 10 may include implants and/or spinal constructs, which may include one or a plurality of plates, rods, connectors and/or bone fasteners for use with a single vertebral level or a plurality of vertebral levels.

Although the procedures described above were shown and described with the procedure occurring in or adjacent vertebrae V, it is envisioned that present disclosure may also be used in other areas of body B, such as, for example, vertebrae V, the patient's sacrum S, the patient's iliac bone IB, or any combination of the above. It is contemplated that the present disclosure may be used in any area of body B where multiple entry points are necessary.

In one embodiment, system 10 includes an agent, which may be disposed, packed, coated or layered within, on or about the components and/or surfaces of system 10. In some embodiments, the agent may include bone growth promoting material, such as, for example, bone graft allograft, xenograft, autograft, bone paste, bone chips, Skelite®, and/or BMP to enhance fixation of the components and/or surfaces of system 10 with vertebrae. In some embodiments, the agent may include one or a plurality of therapeutic agents and/or pharmacological agents for release, including sustained release, to treat, for example, pain, inflammation and degeneration. In such embodiments, titanium coatings may be applied via a variety of methods, including but not limited to plasma spray coating and/or mechanical attachment of titanium plates to form a PEEK/Titanium implant.

The various embodiments described herein may be used to enable a method for surgically treating a spine in a patient. Referring generally to FIG. 1E the method may comprise inserting a first device (D1, for example) through an opening I1 using a first approach; and inserting a second device (the interbody implant 07, for example) through another opening I3 using another approach while the first device D1 is inserted through the opening I1, and where the approaches afforded by openings 11 and 13 are different. As described herein, these approaches may comprise one or more of the following: posterior, left lateral, right lateral, anterior, oblique, and posterior midline. Oblique approaches may include, but are not limited to use of the OLIF25™, OLIF51™ and OLIF41™ approaches and instrumentation available from Medtronic Spine. Posterior midline approaches may include, but are not limited to the use of the MIDLF® approach and instrumentation available from Medtronic Spine.

Referring generally to FIGS. 1E and 1L, the various methods described herein may also further comprise positioning the patient such that the openings (I1 and I3, for example) are accessible simultaneously. For example, the patient may be positioned at an angle a relative to a floor F of the operating room such that the various instruments D1-D7 (wherein D7 comprises an interbody implant, trial or inserter as shown generally in FIG. 1E) are accessibly simultaneously to the various surgical personnel in the operating room. Thus, a surgeon or assistant may manipulate instruments (D1-D6, for example), independently or in concert to manipulate one or more vertebral bodies relative to one another while inserting the interbody implant D7. Furthermore, instruments D1-D6 may be used to distract and/or widen an interbody disc space to aid in disc space preparation, ligament release (such as cutting or partial cutting of the anterior longitudinal ligament (ALL)), or distraction while inserting an interbody implant D7 (as shown in FIG. 1E). Selective positioning of the patient as shown generally in FIGS. 1E and 1L may also allow for the creation of new surgical "working planes" along and/or near a border of the traditional posterior and anterior quadrant with the right and left lateral quadrants of the patient (see FIG. 1A) to facilitate a number of oblique approaches (including but not limited to the OLIF25™, OLIF41™ and OLIF51™ procedures developed by Medtronic Spine).

Referring generally to FIGS. 1B and 1E, in some method embodiments, the opening (see I1, FIG. 1E, for example) may extend through a coronal plane CP of a body of the patient (see FIG. 1B). That is, the surgical pathway established through opening I1 (and/or I2 as shown in FIG. 1D) may extend through and intersect the coronal plane CP. Furthermore, the opening (see I3, FIG. 1E, for example) may extend through a sagittal plane SP of a body of the patient (see FIG. 1B). That is, the surgical pathway established through opening I3 may extend through and intersect the sagittal plane SP.

In other embodiments, the opening I1 (and/or I2 as shown in FIG. 1D) may extend obliquely relative to the sagittal plane SP such that the opening I1 (and/or I2) extends through and/or intersects both the coronal plane CP and the sagittal plane SP of the body of the patient. In some such embodiments, the opening I3 (see FIG. 1E) may extend through and/or intersect the sagittal plane SP (see FIG. 1B) of the body of the patient.

According to various method embodiments described herein, the opening I1 (and/or I2 as shown in FIG. 1D) may extend at a range of angles relative to a coronal plane CP (see FIG. 1B) of a body of the patient. For example, the opening I1 (and/or I2) may extend at an angle of about 90 degrees to about −90 degrees relative to the coronal plane CP. In other embodiments, the opening I1 (and/or I2) may extend at an angle of about 45 degrees to about −45 degrees relative to the coronal plane CP. The opening (see I3, FIG. 1E, for example) may also extend at a range of angles relative to a sagittal plane SP (see FIG. 1B) of a body of the patient. For example, the opening I3 may extend at an angle of about 90 degrees to about −90 degrees relative to a sagittal plane SP (see FIG. 1B). In other embodiments, the opening I3 may extend at an angle of about 45 degrees to about-45 degrees relative to a sagittal plane SP.

Referring again generally to FIG. 1E, in some embodiments, inserting the first device D1 comprises positioning the first device D1 (which may include, but is not limited to a Steinmann pin or bone screw with extender) such that the first device D1 engages a first vertebral body V1. In some such embodiments, the method further comprises moving at least one of the first and second devices (D1 and D2, for example) relative to the first vertebral body V1 to adjust a position of the first vertebral body V1 relative to a second vertebral body V2. For example, a surgeon might manipulate vertebral body V1 to better distract the disc space between V1 and V2 while having the opportunity to simultaneously prepare the disc space via the opening I3 and/or to simultaneously insert an interbody implant (see D7, FIGS. 1E-1G, for example) via the opening I3.

In some method embodiments as shown generally in FIG. 1E, the first device may comprise a first manipulation instrument D1 and a second manipulation instrument D6. In such embodiments, inserting the first device may comprise: (1) inserting the first manipulation instrument through the opening I1 such that the first manipulation instrument D1 engages a first vertebral body V1 and (2) inserting the second manipulation instrument D6 through the opening I1 such that the second manipulation instrument D6 engages a second vertebral body V2. The method may further comprise manipulating the first and second manipulation instruments D1, D6 to move the first and second vertebral bodies V1, V2 relative to one another. For example, a surgeon may utilize instruments D1, D6 (which may comprise a variety of temporary and/or permanent implants including, but not limited to Steinmann pins and bone screws with break-off extensions) to manipulate vertebral bodies V1 and V2 to distract the disc space. In some embodiments, a surgeon could also correct deformities using the instruments D1, D6 (using a form of vertebral column manipulation VCM) to rotate and/or de-rotate vertebral bodies V1 and V2, relative to one another. Furthermore, the various compression screw embodiments (see FIGS. 4A-4C, for example) and multi-vertebral level embodiments (see FIGS. 3A-3S, for example) may be used to create single Functional Spinal Units (FSUs) by tying or linking multiple vertebral levels together for fixation and/or manipulation. Thus, the various devices D1, D6 for example, described herein may be used to manipulate an entire FSU relative to another FSU. Furthermore, the various embodiments described herein may be used for larger-scale VCM maneuvers, where a portion of the thoracic spine is manipulated about the axis extending generally along the spinal column relative to the cervical or lumbar spine (and vice-versa). The construction of large scale FSUs using the methods described herein may enable and/or facilitate such maneuvers.

Referring again to FIGS. 1E-1G, in some embodiments, the second device D7 may comprise a spinal implant (including but not limited to an interbody implant such as the CLYDESDALE® implant available from Medtronic). In such embodiments, the method may further comprise inserting the second device comprises inserting the spinal implant D7 between the first and second vertebral bodies V1, V2. In other embodiments, the second device may comprise a variety of surgical instruments that may be preferable inserted via the incision I3 while manipulation of the vertebral bodies V1, V2 is accomplished via the incision(s) (see I1, I2, FIG. 1E, for example). The second device may comprise instruments that may include, but are not limited to: discectomy devices, disc preparation instruments, shavers, curettes, rongeurs, Kerrison punches, trials, distractors, cylindrical pivots or fulcrum devices, expandable distractors (such as the Medtronic SCISSOR JACK®), inserters. Any of the various permutations of the first and second devices (D1-D7) may also be inserted with the aid of surgical navigation technology as described further herein and as shown generally with respect to navigated instrument N (see FIG. 1Q).

Now referring generally to FIG. 2D, in some embodiments, the first and second devices inserted via two openings 11, 13 (see FIG. 1E) may comprise two bone screws having shafts 12, 18. The bone screws having shafts 12, 18 may both be inserted into a single vertebral body V1 so that the screws having shafts 12, 18 interact and/or come into close proximity so as to apply stresses and/or compressive force to the interior of the vertebral body V1 to encourage bone growth in accordance with Wolff's law. In some embodiments, a threaded shaft of the first bone screw 12 engages a threaded shaft of the second bone screw having shaft 18. At least one of the bone screws having shafts 12, 18 may also be cannulated and/or fenestrated such that the screws having shafts 12, 18 may be used to convey materials, instruments, and/or electrodes to the interior of the vertebral body V1. For example cannulated bone screws (see FIG. 2D, for example) may be used to convey bone growth materials, bone cements, bone paste, and/or analgesics to the interior of the vertebral bodies V1, V2. In other embodiments, the cannulated bone screws having shafts 12, 18 may also be used to introduce a stimulation electrode through the cannulation and into the vertebral body V1 or V2 (or any other bony structure treated using the various procedures described herein). The stimulation electrode may comprise a probe for neural integrity monitoring (NIM) or a stimulation electrode used to encourage bone growth in the interior of the vertebral body.

It should also be noted that any of the first and second devices D1, D2, D3, D4, D5, D6 and/or D7 as shown generally in FIGS. 1E-1G may be inserted percutaneously via one or more "stab" incisions. For example, while devices D1 and D6 are shown being inserted through a single opening I1 in FIG. 1E, any one of the devices D1-D7 may be introduced into a discrete incision or opening along a selected surgical approach.

A method for surgically treating a spine in a patient is also disclosed, comprising performing a first surgical procedure with the patient in a surgical position (such as the insertion of devices D1, D2, D3, D6 in an angulated patient position shown in FIG. 1L); and performing a second surgical procedure (such as the insertion of lateral devices D4, D5) without moving the patient from the surgical position. The first and second surgical procedures may be selected from a group consisting of: discectomy, laminotomy, laminectomy, direct decompression, indirect decompression, cutting an anterior longitudinal ligament, implant insertion, trial insertion, distraction of vertebrae to ease implant insertion, distraction of vertebrae to facilitate disc removal, distraction of vertebrae to facilitate visualization and creation of a fulcrum. In some such embodiments, the first surgical procedure is different than the second surgical procedure. For example, the first surgical procedure may comprise distraction of the vertebral bodies V1 and V2 using devices D1 and D6, respectively, while the second surgical procedure may comprise inserting an interbody implant D7 (see FIG. 1K, for example).

It will be understood that various modifications and/or combinations may be made to the embodiments disclosed herein. Therefore, the above description should not be construed as limiting, but merely as exemplification of the various embodiments. Those skilled in the art will envision other modifications within the scope and spirit of the claims appended hereto.

We claim:

1. A method for surgically treating a spine of a patient, the method comprising:

positioning a patient on a surgical table for surgery;

accessing a first portion of the spine of the patient via a first incision on a first lateral portion of the patient located on a first side of the sagittal plane;

accessing a second portion of the spine of the patient via a second incision on a first posterior portion of the patient on the first side of the sagittal plane;

accessing a third portion of the spine of the patient via a third incision on a second posterior portion of the patient on an opposite second side of the sagittal plane;

inserting a spinal implant into a disc between an upper first vertebrae and a lower second vertebrae at the first portion of the spine via access through the first incision;

inserting a first bone screw into and through portions of the upper first vertebrae at the first posterior portion of the spine via access through the second incision so that the first bone screw follows an inferior-anterior trajectory to position a first tip of the first bone screw adjacent a first anterior portion of the spinal implant; and inserting a second bone screw into and through portions of the lower second vertebrae at the second posterior portion of the spine via access through the third incision so that the second bone screw follows a superior-anterior trajectory to position a second tip of the second bone screw adjacent a second anterior portion of the spinal implant.

2. The method of claim 1, wherein the first tip of the first bone screw is one of anteriorly positioned and posteriorly positioned relative to the second tip of the second bone screw.

3. The method of claim 1, wherein one of the first tip of the first bone screw and the second tip of the second bone screw is contacted to the spinal implant.

4. The method of claim 3, wherein the other of the first tip of the first bone screw and the second tip of the second bone screw is contacted to the spinal implant.

5. The method of claim 1, further comprising maintaining the spinal implant in position in the disc space via the positioning of the first tip adjacent the first anterior portion and the positioning of the second tip adjacent to the second anterior portion of the spinal implant.

6. The method of claim 1, further comprising assessing a fourth portion of the spine of the patient via one of the second incision and the third incision, and inserting a third bone screw through the one of the second incision and the third incision to contact at least one of the first vertebrae and the second vertebrae.

7. The method of claim 6, wherein the inserting of the third bone screw includes insertion of the third bone screw through the second incision through the upper first vertebrae, across the disc space, and into contact with the lower second vertebrae.

8. The method of claim 7, wherein, after the insertion of the third bone screw, a third tip of the third bone screw contacts a posterior portion of the spinal implant and prevents the spinal implant from moving posteriorly.

9. The method of claim 6, wherein the inserting of the third bone screw includes insertion of the third bone screw through the third incision through the lower second vertebrae, across the disc space, and into contact with the upper first vertebrae.

10. The method of claim 9, wherein, after the insertion of the third bone screw, a third tip of the third bone screw contacts a posterior portion of the spinal implant and prevents the spinal implant from moving posteriorly.

11. The method of claim 1, further comprising supporting the patient on the surgical table so that the coronal plane of the patient is oriented at an acute angle relative to horizonal.

12. A method for surgically treating a spine of a patient, the method comprising:

positioning a patient on a surgical table for surgery;

accessing a first portion of the spine of the patient via a first incision on a first lateral portion of the patient located on a first side of the sagittal plane;

accessing a second portion of the spine of the patient via a second incision on a first posterior portion of the patient on the first side of the sagittal plane;

accessing a third portion of the spine of the patient via a third incision on a second posterior portion of the patient on an opposite second side of the sagittal plane;

inserting a spinal implant into a disc between an upper first vertebrae and a lower second vertebrae at the first portion of the spine via access through the first incision;

inserting a first bone screw into and through portions of the upper first vertebrae at the first posterior portion of the spine via access through the second incision so that the first bone screw follows an inferior-anterior trajectory to contact a first tip of the first bone screw to a first anterior portion of the spinal implant; and inserting a second bone screw into and through portions of the lower second vertebrae at the second posterior portion of the spine via access through the third incision so that the second bone screw follows a superior-anterior trajectory to contact a second tip of the second bone screw to a second anterior portion of the spinal implant;

wherein the contact of the first tip and the second tip to the spinal implant serves in maintaining the spinal implant in position within the disc space.

13. The method of claim 12, wherein the first tip of the first bone screw is one of anteriorly positioned and posteriorly positioned relative to the second tip of the second bone screw.

14. The method of claim 12, further comprising assessing a fourth portion of the spine of the patient via one of the second incision and the third incision, and inserting a third bone screw through the one of the second incision and the third incision to contact at least one of the first vertebrae and the second vertebrae.

15. The method of claim 14, wherein the inserting of the third bone screw includes insertion of the third bone screw through the second incision through the upper first vertebrae, across the disc space, and into contact with the lower second vertebrae.

16. The method of claim 15, wherein, after the insertion of the third bone screw, a third tip of the third bone screw contacts a posterior portion of the spinal implant and prevents the spinal implant from moving posteriorly.

17. The method of claim 14, wherein the inserting of the third bone screw includes insertion of the third bone screw through the third incision through the lower second vertebrae, across the disc space, and into contact with the upper first vertebrae.

18. The method of claim 17, wherein, after the insertion of the third bone screw, a third tip of the third bone screw contacts a posterior portion of the spinal implant and prevents the spinal implant from moving posteriorly.

19. The method of claim 12, further comprising supporting the patient on the surgical table so that the coronal plane of the patient is oriented at an acute angle relative to horizonal.

20. A method for surgically treating a spine of a patient, the method comprising:

positioning a patient on a surgical table for surgery, and supporting the patient on the surgical table so that the coronal plane of the patient is oriented at an acute angle relative to horizonal;

accessing a first portion of the spine of the patient via a first incision on a first lateral portion of the patient located on a first side of the sagittal plane;

accessing a second portion of the spine of the patient via a second incision on a first posterior portion of the patient on the first side of the sagittal plane;

accessing a third portion of the spine of the patient via a third incision on a second posterior portion of the patient on an opposite second side of the sagittal plane;

inserting a first bone screw into a vertebral body of a vertebrae in a lateral direction at the first portion of the spine via access through the first incision;

inserting a second bone screw into and through portions of the vertebrae at the first posterior portion of the spine via access through the second incision so that the first bone screw follows an at least in part anterior trajectory to position a first tip of the second bone screw adjacent a first portion of the first bone screw; and inserting a third bone screw into and through portions of the vertebrae at the second posterior portion of the spine via access through the third incision so that the second bone screw follows an at least in part anterior trajectory to position a second tip of the third bone screw adjacent a second portion of the first bone screw.

21. The method of claim 20, wherein a first plane oriented in a cranial-caudal direction extends in a direction along a mid-longitudinal axis of the second bone screw, and a second plane oriented in a cranial-caudal direction extends in a direction along a mid-longitudinal axis of the third bone screw, the first plane and the second plane intersecting one another anteriorly of the first bone screw.

22. The method of claim 20, wherein the first tip of the second bone screw is one of positioned superiorly and inferiorly relative to the first bone screw, and the second tip of the third bone screw is the other of positioned superiorly and inferiorly relative to the first bone screw.

* * * * *